United States Patent [19]

Kojima et al.

[11] Patent Number: 5,760,025
[45] Date of Patent: Jun. 2, 1998

[54] STEROID DERIVATIVES FOR THE TREATMENT OF PROSTATIC HYPERTROPHY, THEIR PREPARATION AND USES

[75] Inventors: Koichi Kojima; Hitoshi Kurata; Koki Ishibashi; Hiroyoshi Horikoshi; Takakazu Hamada, all of Tokyo, Japan

[73] Assignee: Sankyo Company, Limited, Tokyo, Japan

[21] Appl. No.: 414,909

[22] Filed: Mar. 31, 1995

Related U.S. Application Data

[62] Division of Ser. No. 375,264, Jan. 19, 1995, Pat. No. 5,536,714, which is a continuation of Ser. No. 49,140, Apr. 19, 1993.

[30] Foreign Application Priority Data

Apr. 20, 1992 [JP] Japan ................. 4-99816
Dec. 8, 1992 [JP] Japan ................. 4-328043

[51] Int. Cl.$^6$ .................. A61K 58/00; A61K 56/00
[52] U.S. Cl. .................. 514/169; 514/172; 514/174; 514/175; 514/176; 552/610; 540/2; 540/107; 540/108; 540/110; 540/111; 540/113; 540/114; 540/115; 540/116; 540/120
[58] Field of Search ............. 552/610; 514/169, 514/172, 174, 175, 176; 540/2, 107, 108, 110, 111, 113, 114, 115, 116, 120

[56] References Cited

U.S. PATENT DOCUMENTS

| | | | |
|---|---|---|---|
| 5,032,586 | 7/1991 | Metcalf et al. | 514/177 |
| 5,091,380 | 2/1992 | Rasmusson et al. | 514/169 |
| 5,137,882 | 8/1992 | Holt et al. | 514/182 |
| 5,196,411 | 3/1993 | Rasmusson et al. | 514/169 |
| 5,302,621 | 4/1994 | Kojima et al. | |

FOREIGN PATENT DOCUMENTS

| | | |
|---|---|---|
| 0 004 949 | 10/1979 | European Pat. Off. |
| 0 155 096 | 9/1985 | European Pat. Off. |
| 0 289 327 | 11/1988 | European Pat. Off. |
| 0 465 141 | 1/1992 | European Pat. Off. |
| 0 465 141 A2 | 1/1992 | European Pat. Off. |
| WO 92/18132 | 10/1992 | WIPO |

OTHER PUBLICATIONS

Chemical and Pharmaceutical Bulletin, vol. 33, No. 5, (1985) pp. 2164–2167, "Allylic Rearrangement of Alpha, Beta–Unsaturated Ketone–Diethyl Phosphorocyanidate Adducts".

Dennis A. Holt et al, "Inhibition of Steroid 5α–Reductase by Unsaturated 3–Carboxysteroids", J. Med. Chem., 33, pp. 943–950 (1990).

Mark A. Levy et al, "Inhibition of Rat Liver Steroid 5α–Reductase by 2–Androstene–3–Carboxylic Acids: Mechanism of Enzyme–Inhibitor Interaction", Biochemistry, 29, pp. 2815–2824 (1990).

*Primary Examiner*—Kimberly J. Prior
*Attorney, Agent, or Firm*—Frishauf, Holtz, Goodman, Langer & Chick, P.C.

[57] ABSTRACT

Compounds of formula (I):

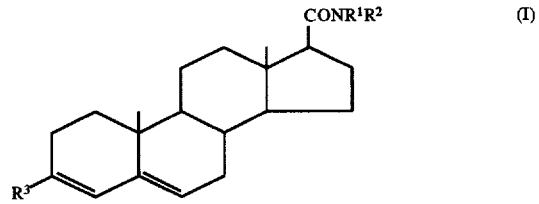

[wherein: $R^1$ is hydrogen, alkyl, aryl-substituted alkyl or aromatic heterocyclic-substituted alkyl; $R^2$ is: aryl-substituted alkyl, aromatic heterocyclic-substituted alkyl or diarylamino; and $R^3$ is carboxy or a group of formula —$CONHSO_2R^4$ wherein $R^4$ is alkyl]; and pharmaceutically acceptable salts and esters thereof have valuable 5α-reductase inhibitory activity and can thus be used for the treatment and prophylaxis of, inter alia, prostatic hypertrophy as well as other disorders arising from excess levels of 5α-dihydrotestosterone.

22 Claims, No Drawings

STEROID DERIVATIVES FOR THE TREATMENT OF PROSTATIC HYPERTROPHY, THEIR PREPARATION AND USES

This is a division of application Ser. No. 08/375,264 filed Jan. 19, 1995, now U.S. Pat. No. 5,536,714, which is a continuation of application Ser. No. 08/049,140 filed Apr. 19, 1993, now abandoned.

BACKGROUND OF THE INVENTION

The present invention relates to a series of new steroid derivatives which have the ability to inhibit the activity or effects of testosterone 5α-reductase, and can thus be used for the treatment or prophylaxis of prostatic hypertrophy. The invention also provides methods and compositions using these new compounds, as well as processes for preparing them.

Testosterone is an active hormone produced in the male by the testes. It may be reduced by 5α-reductase to 5α-dihydrotestosterone, which is active, inter alia, in the prostate.

High levels of 5α-dihydrotestosterone have been implicated in a number of disorders, including prostatic enlargement, acne, male pattern baldness and female hirsutism. Enlargement of the prostate, otherwise known as "prostatic hypertrophy", is an age-related, progressive disease, which afflicts a high proportion of men over 50 years of age. Since it can result in impaired urinary function, it is generally dealt with by surgery, which itself has undesired side effects, including sterility. In an effort to avoid this, attempts have been made to develop drugs which will prevent or treat the condition. Although success has been achieved by the administration of so-called "anti-androgens", such as the oestrogens or derivatives thereof, these have resulted in side effects, such as feminisation, which many men presently consider undesirable.

There is, therefore, a need for a drug capable of treating or preventing prostatic hypertrophy without the feminising effects of the anti-androgens.

The other effects of high levels of 5α-dihydrotestosterone, that is acne, male pattern baldness and female hirsutism, are not medically serious, but are very distressing for the sufferers, and no reliable therapy is currently available.

Since the 5α-reductase inhibitors do not inhibit the activity of testosterone, it was postulated that they might provide the required activity, and a number of such compounds have been developed which demonstrate the accuracy of this hypothesis.

For example, European Patent Publications No. 4949 and 155 096 disclose some androstane derivatives which are claimed to have 5α-reductase inhibitory activity. These, however, differ from the compounds of the present invention in that they have a heterocyclic ring for the so-called "A-ring" of the steroid moiety, in place of the carbocyclic ring of the present compounds.

The closest prior art is believed to be the compounds described in European Patent Publication No. 289 327 and in J. Med. Chem., 33, 943–950 (1990), especially at page 945, and in Biochemistry, 29, 2815–2824 (1990), all of which disclose the compounds hereinafter referred to as Compounds A and B, which are 17β-(diisopropylcarbamoyl) androsta-3,5-diene-3-carboxylic acid and 17β-t-butylcarbamoylandrosta-3,5-diene-3-carboxylic acid, respectively, which have the formulae (A) and (B), respectively:

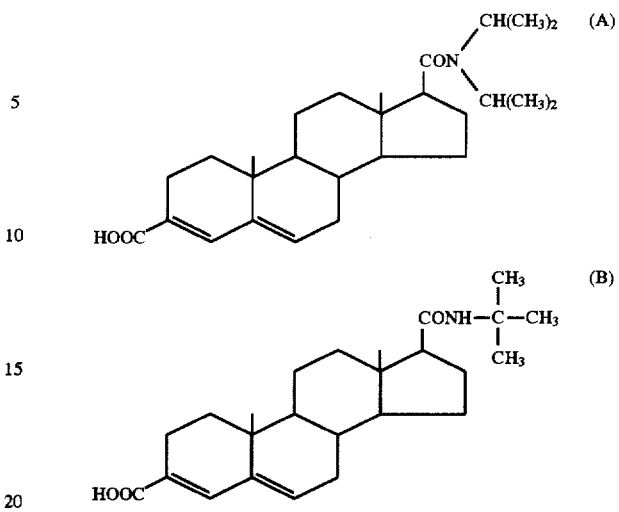

Of these, the t-butyl compound, Compound B, is thought to have the best balance of activities, toxicity and usefulness and is currently under investigation, and now in Phase III, as a potential commercial drug.

BRIEF SUMMARY OF INVENTION

We have now discovered a series of new androstane derivatives which have valuable 5α-reductase inhibitory activity, which is substantially greater (in our tests by an order of magnitude) than the best of the prior art, namely the t-butyl compound, Compound B.

It is, therefore, an object of the present invention to provide a series of new androstane derivatives.

It is a further, and more specific, object of the invention to provide such compounds having 5α-reductase inhibitory activity.

Other objects and advantages will become apparent as the description proceeds.

Accordingly, the compounds of the present invention are those compounds of formula (I):

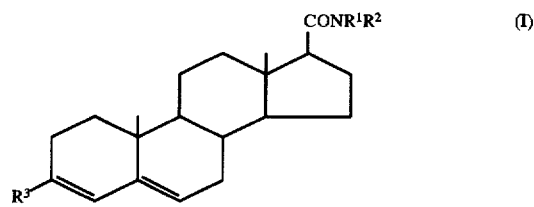

wherein:

$R^1$ represents: a hydrogen atom; an alkyl group having from 1 to 6 carbon atoms; or a substituted alkyl group having from 1 to 6 carbon atoms and having at least one substituent selected from the group consisting of aryl groups as defined below and aromatic heterocyclic groups as defined below;

$R^2$ represents:
  a substituted alkyl group having from 1 to 6 carbon atoms and having at least one substituent selected from the group consisting of aryl groups as defined below and aromatic heterocyclic groups as defined below, and said alkyl group further optionally having a single hydroxy or carboxy substituent; or
  a diarylamino group in which the two aryl parts are the same or different and each is as defined below;

$R^3$ represents a carboxy group or a group of formula —$CONHSO_2R^4$ wherein $R^4$ represents an alkyl group having from 1 to 6 carbon atoms;

said aryl groups are carbocyclic aromatic groups having from 6 to 14 ring carbon atoms and which are unsubstituted or are substituted by at least one substituent selected from the group consisting of substituents A, defined below;

said aromatic heterocyclic groups have 5 or 6 ring atoms of which from 1 to 3 are hetero-atoms selected from the group consisting of nitrogen, oxygen and sulfur hetero-atoms and the remainder are carbon atoms, said group being unsubstituted or being substituted by at least one substituent selected from the group consisting of substituents B, defined below;

said substituents A are selected from the group consisting of: alkyl groups having from 1 to 6 carbon atoms; alkoxy groups having from 1 to 6 carbon atoms; alkoxycarbonyl groups having from 2 to 7 carbon atoms; hydroxy groups; halogen atoms; amino groups; alkylamino groups having from 1 to 6 carbon atoms; dialkylamino groups in which each alkyl part has from 1 to 6 carbon atoms; aliphatic acylamino groups having from 1 to 6 carbon atoms; aromatic acylamino groups in which the aromatic part is a carbocyclic aryl group which has from 6 to 10 ring carbon atoms and which is unsubstituted or is substituted by at least one substituent selected from the group consisting of substituents C, defined below; cyano groups; nitro groups; and carboxy groups;

said substituents B are selected from the group consisting of: alkyl groups having from 1 to 6 carbon atoms; alkoxy groups having from 1 to 6 carbon atoms; hydroxy groups; halogen atoms; carbocyclic aryl groups which have from 6 to 10 ring carbon atoms and which are unsubstituted or are substituted by at least one substituent selected from the group consisting of substituents C, defined below; amino groups; alkylamino groups having from 1 to 6 carbon atoms; dialkylamino groups in which each alkyl part has from 1 to 6 carbon atoms; aliphatic acylamino groups having from 1 to 6 carbon atoms; aromatic acylamino groups in which the aromatic part is a carbocyclic aryl group which has from 6 to 10 ring carbon atoms and which is unsubstituted or is substituted by at least one substituent selected from the group consisting of substituents C, defined below; nitro groups; and carboxy groups;

said substituents C are selected from the group consisting of: alkyl groups having from 1 to 6 carbon atoms; alkoxy groups having from 1 to 6 carbon atoms; hydroxy groups; halogen atoms; amino groups; alkylamino groups having from 1 to 6 carbon atoms; dialkylamino groups in which each alkyl part has from 1 to 6 carbon atoms; aliphatic acylamino groups having from 1 to 6 carbon atoms; cyano groups; nitro groups; and carboxy groups;

and pharmaceutically acceptable salts and esters thereof and other physiologically functional derivatives of said compounds of formula (I) which are capable of conversion in the mammalian body to said compounds of formula (I)

The invention also provides a pharmaceutical composition for the treatment or prophylaxis of disorders arising from high levels of 5α-reductase, notably prostatic hypertrophy, which composition comprises an effective amount of an active compound in admixture with a pharmaceutically acceptable carrier or diluent, wherein said active compound is selected from the group consisting of compounds of formula (I), defined above, and pharmaceutically acceptable salts and esters thereof.

The invention still further provides a method for the treatment or prophylaxis of disorders arising from high levels of 5α-reductase, notably prostatic hypertrophy, in a mammal, which may be human, which method comprises administering to said mammal an effective amount of an active compound, wherein said active compound is selected from the group consisting of compounds of formula (I), defined above, and pharmaceutically acceptable salts and esters thereof.

The invention also provides processes for the preparation of the compounds of the present invention, which processes are described in more detail hereafter.

DETAILED DESCRIPTION OF INVENTION

In the compounds of the present invention, where $R^1$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups, especially the methyl, ethyl, propyl, isopropyl, butyl, isobutyl, pentyl and hexyl groups. Of these, we prefer those alkyl groups having from 1 to 4 carbon atoms, more preferably from 1 to 3 carbon atoms, the methyl, ethyl, isopropyl and isobutyl groups being more preferred, and the methyl group being most preferred.

Where $R^1$ or $R^2$ represents a substituted alkyl group, this may be a straight or branched chain group as defined and exemplified above in relation to the unsubstituted alkyl groups which may be represented by $R^1$, such as the methyl, ethyl, propyl isopropyl, t-butyl and 1-methylpentyl groups. Particularly preferred alkyl groups which may be represented by $R^1$ or $R^2$ include the alkyl groups having from 1 to 4 carbon atoms, more preferably alkyl groups having from 1 to 3 carbon atoms, and most preferably the methyl, ethyl and isopropyl groups.

In the case of the substituted alkyl groups represented by $R^1$ or $R^2$, there may be one or more substituents selected from the group consisting of aryl groups and aromatic heterocyclic groups, defined above and exemplified in more detail below. In the case of $R^2$ only, there may optionally be a further substituent selected from the group consisting of hydroxy groups and carboxy groups. There is no particular limitation on the number of such substituents except such as may be imposed by the number of substitutable positions or by steric constraints. In general, however, from 1 to 3 such substituents are preferred, 1 or 2 being more preferred and 1 being most preferred. Where there are two or more substituents, these may be the same as each other or they may be different from each other.

Where the substituent on the substituted alkyl groups represented by $R^1$ or $R^2$ is an aryl group, this is a carbocyclic aromatic group (i.e. an aromatic group containing one or more rings, in which all ring atoms are carbon atoms) having from 6 to 14 ring carbon atoms, preferably from 6 to 10 carbon atoms, and more preferably 6 or 10 carbon atoms. Examples of such groups include the phenyl, indenyl, 1-naphthyl, 2-naphthyl, biphenylenyl, acenaphthylenyl, fluorenyl, phenanthryl and anthryl groups, of which the phenyl and naphthyl groups are preferred, the phenyl group being most preferred. Such aryl groups may be unsubstituted or they may be substituted by one or more or substituents A, defined above and exemplified below. In the case of the substituted groups, there is no particular limitation on the number of such substituents A except such as may be imposed by the number of substitutable positions or possibly by steric constraints. In general, however, from 1 to 4 such substituents are preferred, from 1 to 3 being more preferred and 1 or 2 being most preferred. Where there are two or more substituents, these may be the same as each other or they may be different from each other. Examples of such substituents A include:

alkyl groups having from 1 to 6 carbon atoms, such as those exemplified above in relation to the unsubstituted groups which may be represented by $R^1$;

alkoxy groups having from 1 to 6 carbon atoms, such as the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methoxypentyloxy, 3-methoxypentyloxy, 2-methoxypentyloxy, 1-methoxypentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups, of which the methoxy and ethoxy groups are preferred;

alkoxycarbonyl groups having from 2 to 7 carbon atoms, that is the alkoxy part has from 1 to 6 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methoxypentyloxycarbonyl, 3-methoxypentyloxycarbonyl, 2-methoxypentyloxycarbonyl, 1-methoxypentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups, of which the methoxycarbonyl and ethoxycarbonyl groups are preferred;

hydroxy groups;

halogen atoms, such as the fluorine, chlorine, bromine and iodine atoms, of which the fluorine, chlorine and bromine atoms are preferred, the fluorine and chlorine atoms being most preferred;

amino groups;

alkylamino groups having from 1 to 6 carbon atoms, such as the methylamino, ethylamino, propylamino, butylamino, isobutylamino, pentylamino and hexylamino groups; of these, we prefer the groups in which the alkyl part has from 1 to 4, more preferably 1 or 2, carbon atoms;

dialkylamino groups in which each alkyl part has from 1 to 6 carbon atoms, such as the dimethylamino, diethylamino, methylethylamino, dipropylamino, diisopropylamino, dibutylamino, dipentylamino, dihexylamino, methylbutylamino and ethylpropylamino groups; of these, we prefer the groups in which each alkyl part has from 1 to 4, more preferably 1 or 2, carbon atoms;

aliphatic acylamino groups having from 1 to 6 carbon atoms, such as the formylamino, acetylamino, propionylamino, butyrylamino, valerylamino, isovalerylamino, pivaloylamino and hexanoylamino groups, of which those groups having from 1 to 5 carbon atoms are preferred, groups having 1 or 3 carbon atoms being most preferred;

aromatic acylamino groups in which the aromatic part is a carbocyclic aryl group which has from 6 to 10, preferably 6 or 10, ring carbon atoms (for example the phenyl or naphthyl groups), and which is unsubstituted or is substituted by at least one substituent selected from the group consisting of substituents C, defined above, such as the benzoyl or naphthoyl groups and substituted derivatives thereof;

cyano groups; nitro groups; and carboxy groups;

Examples of the groups and atoms included in substituents C are the same as the corresponding groups and atoms included in substituents A and given above.

Of these substituents A, we prefer alkyl groups having from 1 to 4 carbon atoms, alkoxy groups having from 1 to 4 carbon atoms, alkoxycarbonyl groups having 2 or 3 carbon atoms, hydroxy groups, halogen atoms, amino groups, alkylamino groups having from 1 to 4 carbon atoms, dialkylamino groups in which each alkyl part has from 1 to 4 carbon atoms, and aliphatic acylamino groups having from 1 to 3 carbon atoms, more preferably the methyl, ethyl, methoxy, ethoxy, methoxycarbonyl, ethoxycarbonyl, hydroxy, amino, methylamino, ethylamino, dimethylamino, diethylamino, methylethylamino, formylamino and acetylamino groups, and the fluorine, chlorine and bromine atoms, and most preferably the methyl, methoxy, ethoxy and hydroxy groups, and the fluorine and chlorine atoms.

Where the substituent on the substituted alkyl groups represented by $R^1$ or $R^2$ is an aromatic heterocyclic group, this is a heterocyclic group having 5 or 6 ring atoms in an aromatic ring. The group also has from 1 to 3 hetero-atoms selected from the group consisting of nitrogen atoms, oxygen atoms and sulfur atoms, the remaining ring atoms being carbon atoms. In general, where there are three hetero-atoms, we prefer that 1, 2 or 3, preferably 2 or 3, are nitrogen atoms and, correspondingly, 2, 1 or 0, preferably 1 or 0, are oxygen and/or sulfur atoms. Where there are 1 or 2 hetero-atoms, they may be freely selected from nitrogen, oxygen and sulfur atoms. Examples of such groups include the furyl, thienyl, pyridyl, pyrrolyl, imidazolyl, thiazolyl, isothiazolyl, oxazolyl, isoxazolyl, pyrazinyl, pyrimidinyl and pyridazinyl groups. Of these, we prefer the furyl, thienyl and pyridyl groups, more preferably the furyl and thienyl groups, and most preferably the thienyl group. Such aromatic heterocyclic groups may be unsubstituted or they may be substituted by one or more of substituents B, defined above. In the case of the substituted groups, there is no particular limitation on the number of such substituents B except such as may be imposed by the number of substitutable positions or possibly by steric constraints. In general, however, from 1 to 3 such substituents are preferred, 1 or 2 being most preferred. Where there are two or more substituents, these may be the same as each other or they may be different from each other. Examples of such substituents B include the corresponding groups and atoms exemplified above in relation to substituents A and aryl groups having from 6 to 10 ring carbon atoms such as those exemplified above and included in the aryl groups which may be represented by $R^1$. In particular, preferred substituents include alkyl groups having from 1 to 6 carbon atoms (such as those exemplified above in relation to $R^1$) and halogen atom (such as the fluorine, chlorine, bromine and iodine atoms). More preferred substituents are alkyl groups having from 1 to 4 carbon atoms, fluorine atoms and chlorine atoms, still more preferably a methyl or ethyl group, and most preferably a methyl group.

$R^3$ and possibly substituents A, B or C may represent carboxy groups, and the group represented by $R^2$ may include a carboxy group, and the compounds of the present invention may therefore form salts and esters as well as other derivatives, which are well known in the art, such as amides. There is no restriction on the nature of such salts, esters and other derivatives, provided that, where they are to be used for therapeutic purposes, they are pharmaceutically acceptable, that is they are not less active (or unacceptably less active) or more toxic (or unacceptably more toxic) than the parent compound. However, where the compounds are to be used for other purposes, for example as intermediates in the preparation of other compounds, even this restriction may not apply.

Preferred ester groups are those that can be converted to a carboxy group in vivo. Examples of such ester groups include:

alkyl groups having from 1 to 6, preferably from 1 to 4, carbon atoms, such as those exemplified above in relation to $R^1$;

haloalkyl groups having from 1 to 6, preferably from 1 to 4, carbon atoms, such as the trifluoromethyl, 2,2,2-trifluoroethyl, 2,2,2-trichloroethyl, 2-fluoroethyl, 2-chloroethyl, 2-iodoethyl, 3-chloropropyl, 4-fluorobutyl and 6-iodohexyl groups, preferably the 2,2,2-trichloroethyl and 2-chloroethyl groups;

hydroxyalkyl groups having from 1 to 6, preferably from 1 to 4, carbon atoms, such as the 2-hydroxyethyl, 2,3-dihydroxypropyl, 3-hydroxypropyl, 3,4-dihydroxybutyl and 4-hydroxybutyl groups, preferably the 2-hydroxyethyl group;

alkoxyalkyl and alkoxyalkoxyalkyl groups in which the alkyl and alkoxy groups each have from 1 to 6, preferably from 1 to 4, carbon atoms, such as the methoxymethyl, 2-methoxyethyl, 2-ethoxyethyl and 2-methoxyethoxymethyl groups, preferably the methoxymethyl group;

the phenacyl group;

alkoxycarbonylalkyl groups in which the alkyl and alkoxy groups each have from 1 to 6, preferably from 1 to 4, carbon atoms, such as the methoxycarbonylmethyl group;

cyanoalkyl groups in which the alkyl part has from 1 to 6, preferably from 1 to 4, carbon atoms, such as the cyanomethyl and 2-cyanoethyl groups;

alkylthiomethyl groups in which the alkyl part has from 1 to 6, preferably from 1 to 4, carbon atoms, such as the methylthiomethyl and ethylthiomethyl groups;

arylthiomethyl groups in which the aryl part has from 6 to 10 ring carbon atoms and may be unsubstituted or may be substituted by at least one substituent selected from the group consisting of substituents C, defined and exemplified above, such as the phenylthiomethyl and naphthylthiomethyl groups;

alkylsulfonylalkyl groups in which each alkyl part has from 1 to 6, preferably from 1 to 4, carbon atoms, and in which the alkylsulfonyl part may be unsubstituted or may be substituted by at least one halogen atom, such as the 2-methanesulfonylethyl and 2-trifluoromethanesulfonylethyl groups;

arylsulfonylalkyl groups in which the aryl part has from 6 to 10 ring carbon atoms and may be unsubstituted or may be substituted by at least one substituent selected from the group consisting of substituents C, defined and exemplified above, and the alkyl part has from 1 to 6, preferably from 1 to 4, carbon atoms, such as the 2-benzenesulfonylethyl and 2-toluenesulfonylethyl groups;

aralkyl groups in which the aryl part has from 6 to 10 ring carbon atoms and may be unsubstituted or may be substituted by at least one substituent selected from the group consisting of substituents C, defined and exemplified above, and the alkyl part has from 1 to 6, preferably from 1 to 3, carbon atoms, such as the benzyl, naphthylmethyl, diphenylmethyl, trityl, 6-phenylhexyl, 4-methylbenzyl, 2,4,6-trimethylbenzyl, 3,4,5-trimethylbenzyl, 4-methoxybenzyl, 4-chlorobenzyl and 4-bromobenzyl groups, preferably those aralkyl groups in which the aryl part is a phenyl group and the alkyl part has from 1 to 6, preferably from 1 to 3, carbon atoms, more preferably the benzyl, 4-methylbenzyl, 4-chlorobenzyl and 4-bromobenzyl groups;

aryl groups, such as those defined and exemplified above in relation to the aryl groups which may be substituents on the substituted alkyl groups represented by $R^1$ and $R^2$;

silyl groups of formula $-SiR^aR^bR^c$, wherein 1, 2 or 3 of $R^a$, $R^b$ and $R^c$, which may be the same or different from each other, each represents an alkyl group having from 1 to 6 carbon atoms (such as those exemplified above in relation to $R^1$), and correspondingly 2, 1 or 0 of $R^a$, $R^b$ and $R^c$ represents an aryl group, such as those defined and exemplified above in relation to the aryl groups which may be substituents on the substituted alkyl groups represented by $R^1$ and $R^2$; examples of such silyl groups include the trimethylsilyl, triethylsilyl, isopropyldimethylsilyl, t-butyldimethylsilyl, methyldiisopropylsilyl, methyldi-t-butylsilyl, triisopropylsilyl, methyldiphenylsilyl, isopropyldiphenylsilyl, butyldiphenylsilyl and phenyldiisopropylsilyl groups, preferably the trimethylsilyl, t-butyldimethylsilyl and methyldiphenylsilyl groups;

alkanoyloxyalkyl groups in which the alkanoyl and alkyl groups each have from 1 to 6 carbon atoms, preferably from 1 to 4 carbon atoms in the case of alkyl groups or from 1 to 5 carbon atoms in the case of alkanoyl groups, such as the formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups, preferably the formyloxymethyl, acetoxymethyl, propionyloxymethyl, butyryloxymethyl, pivaloyloxymethyl, 1-formyloxyethyl, 1-acetoxyethyl, 1-propionyloxyethyl, 1-butyryloxyethyl and 1-pivaloyloxyethyl groups, more preferably the acetoxymethyl, propionyloxymethyl, butyryloxymethyl, pivaloyloxymethyl, 1-acetoxyethyl, 1-propionyloxyethyl, 1-butyryloxyethyl and 1-pivaloyloxyethyl groups, most preferably the pivaloyloxymethyl and 1-pivaloyloxyethyl groups;

cycloalkanecarbonyloxyalkyl groups in which the cycloalkane part has from 5 to 7, preferably 5 or 6, carbon atoms and the alkyl part has from 1 to 6, preferably from 1 to 4, carbon atoms (such as those exemplified above in relation to $R^1$), such as the cyclopentanecarbonyloxymethyl, cyclohexanecarbonyloxymethyl, 1-(cyclopentanecarbonyloxy)ethyl, 1-(cyclohexanecarbonyloxy)ethyl, 1-(cyclopentanecarbonyloxy)propyl, 1-(cyclohexanecarbonyloxy)propyl, 1-(cyclopentanecarbonyloxy) butyl, 1-(cyclohexanecarbonyloxy)butyl, cycloheptanecarbonyloxymethyl, 1-(cycloheptanecarbonyloxy)ethyl, 1-(cycloheptanecarbonyloxy)propyl and 1-(cycloheptanecarbonyloxy)butyl groups, preferably the cyclopentanecarbonyloxymethyl, cyclohexanecarbonyloxymethyl, 1-(cyclopentanecarbonyloxy)ethyl and 1-(cyclohexanecarbonyloxy)ethyl groups;

alkoxycarbonyloxyalkyl groups in which the alkyl and alkoxy groups each have from 1 to 6, preferably from 1 to 4, carbon atoms, such as the methoxycarbonyloxymethyl, ethoxycarbonyloxymethyl, propoxycarbonyloxymethyl, isopropaxycarbonyloxymethyl, butoxycarbonyloxymethyl, isobutoxycarbonyloxymethyl, pentyloxycarbonyloxymethyl, hexyloxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-pentyloxycarbonyloxyethyl, 1-hexyoxycarbonyloxyethyl, 2-methoxycarbonyloxyethyl, 2-ethoxycarbonyloxyethyl, 2-propoxycarbonyloxyethyl, 2-isopropoxycarbonyloxyethyl, 2-butoxycarbonyloxyethyl, 2-isobutoxycarbonyloxyethyl, 2-pentyloxycarbonyloxyethyl, 2-hexyloxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-pentyloxycarbonyloxypropyl, 1-hexyloxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl, 1-isobutoxycarbonyloxybutyl, 1-methoxycarbonyloxypentyl, 1-ethoxycarbonyloxypentyl, 1-methoxycarbonyloxyhexyl and 1-ethoxycarbonyloxyhexyl groups, preferably the methoxycarbonyloxypropyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl and 1-isobutoxycarbonyloxybutyl groups, more preferably the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-pronoxycarbonyloxyethyl, 1-isopropoxycarbonyloxyethyl, 1-butoxycarbonyloxyethyl and 1-isobutoxycarbonyloxyethyl groups, and most preferably the methoxycarbonyloxymethyl, ethoxycarbonyloxymethyl, isopropoxycarbonyloxymethyl, 1-methoxycarbonyloxyethyl, 1-ethoxycarbonyloxyethyl and 1-isopropoxycarbonyloxyethyl groups;

cycloalkyloxycarbonyloxyalkyl groups in which the cycloalkyl part has from 5 to 7, preferably 5 or 6, carbon atoms and the alkyl part has from 1 to 6, preferably from 1 to 4, carbon atoms (such as those exemplified above in relation to $R^1$), such as the cyclopentyloxycarbonyloxymethyl, cyclohexyloxycarbonyloxymethyl, 1-(cyclopentyloxycarbonyloxy)ethyl, 1-(cyclohexyloxycarbonyloxy)ethyl, 1-(cyclopentyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, cycloheptyloxycarbonyloxymethyl, 1-(cycloheptyloxycarbonyloxy)ethyl, 1-(cycloheptyloxycarbonyloxy)propyl and 1-(cycloheptyloxycarbonyloxy)butyl groups, preferably the cyclopentyloxycarbonyloxymethyl, cyclohexyloxycarbonyloxynethyl, 1-(cyclopentyloxycarbonyloxy)ethyl and 1-(cyclohexyloxycarbonyloxy)ethyl groups;

(5-aryl- or 5-alkyl-2-oxo-1,3-dioxolen-4-yl)methyl groups in which the aryl part has from 6 to 10 ring carbon atoms and may be unsubstituted or may be substituted by at least one substituent selected from the group consisting of substituents C, defined and exemplified above, and the alkyl part has from 1 to 6, preferably from 1 to 4, carbon atoms (such as those exemplified above in relation to $R^1$), such as the (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)- 2-oxo-1,3-dioxolen-4-yl]methyl, [5-(4-chlorophenyl)-2-oxo-1,3-dioxolen-4-yl]methyl, (5-methyl-2-oxo1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups, preferably the (5-phenyl-2-oxo-1,3-dioxolen-4-yl)methyl, (5-methyl-2-oxo-1,3-dioxolen-4-yl)methyl and (5-ethyl-2-oxo-1,3-dioxolen-4-yl)methyl groups, and most preferably the (5-methyl-2-oxo-1,3-dioxolen-4-yl)methyl group; and the phthalidyl group.

Of these, we especially prefer: alkyl groups having from 1 to 4 carbon atoms; benzyl groups; substituted benzyl groups having from 1 to 3 substituents selected from the group consisting of methyl, ethyl, methoxy and ethoxy groups and fluorine and chlorine atoms; the diphenylmethyl group; the naphthylmethyl groups; alkanoyloxyalkyl groups in which the alkanoyl part has from 1 to 5 carbon atoms and the alkyl part has from 1 to 4 carbon atoms; cycloalkanecarbonyloxyalkyl groups in which the cycloalkyl part has from 5 to 7 ring carbon atoms and the alkyl part has from 1 to 4 carbon atoms; alkoxycarbonyloxyalkyl groups in which the alkoxy and alkyl parts each have from 1 to 4 carbon atoms; cycloalkyloxycarbonyloxyalkyl groups in which the cycloalkyl part has from 5 to 7 ring carbon atoms and the alkyl part has from 1 to 4 carbon atoms; (5-phenyl- or 5-alkyl-2-oxo-1,3-dioxolen-4-yl)methyl groups in which the alkyl part has from 1 to 4 carbon atoms; and the phthalidyl group.

More preferred ester groups include: alkyl groups having from 1 to 4 carbon atoms; benzyl groups; alkanoyloxyalkyl groups in which the alkanoyl part has from 1 to 5 carbon atoms and the alkyl part has 1 or 2 carbon atoms; cycloalkanecarbonyloxyalkyl groups in which the cycloalkyl part has from 5 to 7 ring carbon atoms and the alkyl part has 1 or 2 carbon atoms; alkoxycarbonyloxyalkyl groups in which the alkoxy part has from 1 to 4 carbon atoms and the alkyl part has 1 or 2 carbon atoms; cycloalkoxycarbonyloxyalkyl groups in which the cycloalkyl part has from 5 to 7 ring carbon atoms and the alkyl part has 1 or 2 carbon atoms; [5-phenyl-, 5-methyl- or 5-ethyl-2-oxo-1,3-dioxolen-4-yl) methyl groups; and the phthalidyl group.

The most preferred ester groups include: methyl groups, ethyl groups, pivaloyloxymethyl groups, ethoxycarbonyloxymethyl groups, 1-(ethoxycarbonyloxy)ethyl groups, isopropoxycarbonyloxymethyl groups, 1-(isopropoxycarbonyloxy)ethyl groups, (5-methyl-2-oxo-1,3-dioxolen-4-yl)methyl group and phthalidyl groups.

Those compounds of the present invention which contain a carboxy group can also form salts. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with triethylamine, diisopropylamine, cyclohexylamine, dicyclohexylamine and guanidine; and salts with a basic amino acid, such as lysine or arginine. Also, where the compound of the present invention contains a basic group, such as an amino group, in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

Examples of alkyl groups which may be represented by $R^4$ include the alkyl groups exemplified above in relation to $R^1$, especially the methyl and ethyl groups.

In general, in the compounds of the present invention, we prefer that $R^1$ represents a hydrogen atom and $R^2$ is as defined above.

Preferred groups of formula —$NR^1R^2$ include: the benzylamino, (2-, 3- or 4-methylbenzyl)amino, (2-, 3- or 4-methoxybenzyl)amino, (2-, 3- or 4-fluorobenzyl)amino, (2-, 3- or 4-chlorobenzyl)amino, phenethylamino, (2-, 3- or 4-methylphenethyl)amino, (2-, 3- or 4-methoxyphenethyl) amino, (2-, 3- or 4-fluorophenethyl)amino, (2-, 3- or 4-chlorophenethyl)amino, (3-phenylpropyl)amino, (1-methyl-1-phenylethyl)amino, [1-methyl-1-(2-, 3- or 4-methylphenyl)ethyl]amino, [1-methyl-1-(2-, 3- or 4-methoxyphenyl)ethyl]amino, [1-methyl-1-(2-, 3- or 4-fluorophenyl)ethyl]amino, [1-methyl-1-(2-, 3- or 4-chlorophenyl)ethyl]amino, [1-methyl-1-(2-, 3- or 4-hydroxyphenyl)ethyl]amino, [1-methyl-1-(2-, 3- or 4-aminophenyl)ethyl]amino, [1-methyl-1-(2-, 3- or 4-methylaminophenyl)ethyl]amino, [1-methyl-1-(2-, 3- or 4-ethylaminophenyl)ethyl]amino, [1-methyl-1-(2-, 3- or 4-dimethylaminophenyl)ethyl]amino, [1-methyl-1-(2-, 3- or 4-acetamidophenyl)ethyl]amino, [1-methyl-1-(2,3-, 2,4-, 2,5-, 2,6-, 3,4-, 3,5- or 3,6-dimethoxyphenyl)ethyl]amino, (1,1-dimethyl-2-phenylethyl)amino, [1,1-dimethyl-2-(2-, 3- or 4-methylphenyl)ethyl]amino, [1,1-dimethyl-2-(2-, 3- or 4-methoxyphenyl)ethyl]amino, [1,1-dimethyl-2-(2-, 3- or 4-fluorophenyl)ethyl]amino, [1,1-dimethyl-2-(2-, 3- or 4-chlorophenyl)ethyl]amino, benzhydrylamino, [(2-, 3- or 4-), (2'-, 3'- or 4'-)dimethylbenzhydryl]amino, [(2-, 3- or 4-), (2'-, 3'- or 4'-)-dimethoxybenzhydryl]amino, [(2-, 3- or 4-), (2'-, 3'- or 4'-)-difluorobenzhydryl]amino, [(2-, 3- or 4-), (2'-, 3'- or 4'-)-dihydroxybenzhydryl]amino, [(2-, 3- or 4-), (2'-, 3'- or 4'-)-diaminobenzhydryl]amino, [(2-, 3- or 4-), (2'-, 3'- or 4'-)-di(dimethylamino)benzhydryl]amino, (2-, 3- or 4-methylbenzhydryl)amino, (2-, 3- or 4-methoxybenzhydryl)amino, (2-, 3- or 4-fluorobenzhydryl) amino, (2-, 3- or 4-chlorobenzhydryl)amino, (2-, 3- or 4-hydroxybenzhydryl)amino, (2-, 3- or 4-aminobenzhydryl) amino, (2-, 3- or 4-dimethylaminobenzhydryl)amino, (1,1-diphenylethyl)amino, (1,2-diphenylethyl)amino, [2-(2-, 3- or 4-methylphenyl)-1-phenylethyl]amino, [2-(2-, 3- or 4-methoxyphenyl)-1-phenylethyl]amino, [2-(2-, 3- or 4-fluorophenyl)-1-phenylethyl]amino, [2-(2-, 3- or 4-chlorophenyl)-1-phenylethyl]amino, [1-(2-, 3- or 4-fluorophenyl)-2-(2-, 3- or 4-fluorophenyl)ethyl]amino, [1-(2-, 3- or 4-chlorophenyl)-2-(2-, 3- or 4-chlorophenyl)ethyl] amino, [1-(2-, 3- or 4-chlorophenyl)-2-(2-, 3- or 4-methoxyphenyl)ethyl]amino, [1-(2-, 3- or 4-methylphenyl)-2-(2-, 3- or 4-methylphenyl)ethyl]amino, [1-(2-, 3- or 4-hydroxyphenyl)-2-(2-, 3- or 4-hydroxyphenyl)ethyl]amino, [1-(2-, 3- or 4-aminophenyl)-2-(2-, 3- or 4-aminophenyl)ethyl]amino, [1-(2-, 3- or 4-dimethylaminophenyl)-2-(2-, 3- or 4-dimethylaminophenyl)ethyl]amino, [2-(2-, 3- or 4-fluorophenyl)-1-(2-, 3- or 4-methylphenyl)ethyl]amino, [2-(2-, 3- or 4-fluorophenyl)-1-(2-, 3- or 4-methoxyphenyl) ethyl]amino, [2-(2-, 3- or 4-hydroxyphenyl)-1-phenylethyl] amino, [2-(2-, 3- or 4-aminophenyl)-1-phenylethyl]amino, [2-(2-, 3- or 4-dimethylaminophenyl)-1-phenylethyl]amino, [1-(2-, 3- or 4-methoxyphenyl)-2-phenylethyl]amino, (1-methyl-1,2-diphenylethyl)amino, (2,2-diphenylethyl) amino, [2-(2-, 3- or 4-methylphenyl)-2-(2-, 3- or 4-methylphenyl)ethyl]amino, [2-(2-, 3- or 4-methoxyphenyl)-2-(2-, 3- or 4-methoxyphenyl)ethyl] amino, (1-benzyl-4-phenylbutyl)amino, (1,1-diphenylethyl) amino, [1-(2-, 3- or 4-fluorophenyl)-1-(2-, 3- or 4-fluorophenyl)ethyl]amino, [1-(2-, 3- or 4-methylphenyl)-1-(2-, 3- or 4-methylphenyl)ethyl]amino, [1-(2-, 3- or 4-methoxyphenyl)-1-(2-, 3- or 4-methoxyphenyl)ethyl] amino, [1-(2-, 3- or 4-hydroxyphenyl)-1-phenylethyl]amino, [1-(2-, 3- or 4-aminophenyl)-1-phenylethyl]amino, [1-(2-, 3- or 4-dimethylaminophenyl)-1-phenylethyl]amino, tritylamino, [(2-, 3- or 4-), (2'-, 3'- or 4'-), (2"-, 3"- or 4"-)trimethyltrityl]amino, [(2-, 3- or 4-), (2'-, 3'- or 4'-), (2"-, 3"- or 4"-)trifluorotrityl]amino, (1-benzyl-2-phenylethyl) amino, [1-(2-, 3- or 4-fluorobenzyl)-2-(2-, 3- or 4-fluorophenyl)ethyl]amino, (1-benzyl-1-methyl-2-phenylethyl)amino, [1-(2-, 3- or 4-chlorobenzyl)-2-(2-, 3- or 4-chlorophenyl)ethyl]amino, [1-(2-, 3- or 4-fluorobenzyl)-2-(2-, 3- or 4-fluorophenyl)-1-methylethyl]amino, [1-methyl-2-(2-, 3- or 4-methylphenyl)-3-(2-, 3- or 4-methylphenyl)propyl]amino, [2-(2-, 3- or 4-fluoroyphenyl)-3-(2-, 3- or 4-fluoroyphenyl)-1-methylpropyl]amino, (1,3-diphenylpropyl)amino, [1-(2-, 3- or 4-methylphenyl)-3-(2-, 3- or 4-methylphenyl)propyl] amino, [1-(2-, 3- or 4-methoxyphenyl)-3-(2-, 3- or 4-methoxyphenyl)propyl]amino, (1,4-diphenylbutyl)amino, [1-(2-, 3- or 4-chlorophenyl)4-(2-, 3- or 4-chlorophenyl) butyl]amino, [1-(2-, 3- or 4-methoxyphenyl)-4-(2-, 3- or 4-methoxyphenyl)butyl]amino, (1-methyl-3,3-diphenylpropyl)amino, [3-(2-, 3- or 4-fluorophenyl)-3-(2-, 3- or 4-fluorophenyl)-1-methylpropyl]amino, [1-methyl-3-(2-, 3- or 4-methylphenyl)-3-(2-, 3- or 4-methylphenyl) propyl]amino, N-benzyl-N-methylamino, N-benzyl-N-ethylamino, N-benzyl-N-isopropylamino, N-benzyl-N-isobutylamino, N-benzyl-N-t-butylamino, N-(2-, 3- or 4-fluorobenzyl)-N-isopropyl-amino, N-(2-, 3- or 4-chlorobenzyl)-N-isopropylamino, N-(2-, 3- or 4-methylbenzyl)-N-isopropylamino, N-(2-, 3- or 4-methoxybenzyl)-N-isopropylamino, N-(2-, 3- or 4-hydroxybenzyl)-N-isopropylamino, N,N-dibenzylamino, N-benzyl-N-(2-, 3- or 4-methoxybenzyl)amino, N-(2-, 3- or 4-fluorobenzyl)-N-(2-, 3- or 4-fluorobenzyl)amino, N-(2-, 3- or 4-methylbenzyl)-N-(2-, 3- or 4-methylbenzyl)amino, N-(2-, 3- or 4-methoxybenzyl)-N-(2-, 3- or 4-methoxybenzyl)amino, N-(2-, 3- or 4-hydroxybenzyl)-N-(2-, 3- or 4-hydroxybenzyl)amino, N-(2-, 3- or 4-aminobenzyl)-N-(2-, 3- or 4-aminobenzyl)amino, N-(2-, 3- or 4-dimethylaminobenzyl)-N-(2-, 3- or 4-dimethylaminobenzyl)amino, N-benzyl-N-phenylethylamino, N-benzyl-N-(1-phenylethyl)amino, N-benzyl-N-(1-methyl-1-phenylethyl)amino, N,N-diphenylethylamino, N,N-bis(1-phenylethyl)amino, N-benzyl-N-(3-phenylpropyl)amino, (2- or 3-furylmethyl) amino, (2- or 3-thienylmethyl)amino, (2-, 3- or 4-pyridylmethyl)amino, (2- or 5-methyl-2- or 3-furylmethyl)amino, (2- or 5-methyl-2- or 3-thienylmethyl) amino, [2-(2- or 3-furyl)ethyl]amino, [2-(2- or 3-thienyl) ethyl]amino, (3-(2- or 3-furyl)propyl]amino, [3-(2- or 3-thienyl)propyl]amino, [bis(2- or 3-furyl)methyl]amino, [bis(2- or 3-thienyl)methyl]amino, [1,1-bis(2- or 3-furyl) ethyl]amino, [1,1-bis(2- or 3-thienyl)ethyl]amino, [(2- or 5-methyl-2- or 3-furylmethyl), (2- or 5-methyl-2- or 3-furylmethyl]amino, [(2- or 5-methyl-2- or 3-thienylmethyl), (2- or 5-methyl-2- or 3-thienylmethyl] amino, [1-(2- or 3-furyl)-1-methylethyl]amino, [1-(2- or 3-thienyl)-1- methylethyl]amino, [1-(2- or 5-methyl-2- or 3-thienyl)-1-methylethyl]amino, [1-(2- or 3-furyl)-2-(2- or 3-furyl)ethyl]amino, [1-(2- or 5-methyl-2- or 3-furyl)-1-methylethyl]amino, [1-(2- or 3-thienyl)-2-(2- or 3-thienyl) ethyl]amino, [1-(2- or 3-furyl)-2-phenylethyl]amino, [1-(2- or 3-furyl)-2-(2-, 3- or 4-methylphenyl)ethyl]amino, [2-phenyl-1-(2- or 3-thienyl)ethyl]amino, [1-phenyl-2-(2- or 3-thienyl)ethyl]amino, [2-(2-, 3- or 4-methylphenyl)-1-(2- or 3-thienyl)ethyl]amino, [2-(2-, 3- or 4-chlorophenyl)-1-(2- or 3-thienyl)ethyl]amino, [2-(2-, 3- or 4-fluorophenyl)-1-(2- or 3-thienyl)ethyl]amino, [2-(2-, 3- or 4-methoxyphenyl)-1-(2- or 3-thienyl)ethyl]amino, N-(2- or 3-furylmethyl)-N-(2- or 3-furylmethyl)amino, N-(2- or 3-thienylmethyl)-N-(2- or 3-thienylmethyl)amino, [1-(2-, 3- or 4-fluorophenyl)-2-(2- or 3-thienyl)ethyl]amino, N-benzyl-N-(2- or 3-furylmethyl) amino, N-benzyl-N-(2- or 3-thienylmethyl)amino, (2-hydroxy-1,2-diphenylethyl)amino, N',N'-diphenylhydrazino, N'-(2-, 3- or 4-methylphenyl)-N'-phenylhydrazino, N'-(2-, 3- or 4-methoxyphenyl)-N'-phenylhydrazino, N'-(2-, 3- or 4-chlorophenyl)-N'-phenylhydrazino, N'-(2-, 3- or 4-fluorophenyl)-N'-phenylhydrazino, N'-(2-, 3- or 4-hydroxyphenyl)-N'-phenylhydrazino, N'-(2-, 3- or 4-aminophenyl)-N'-phenylhydrazino, N'-(2-, 3- or 4-dimethylaminophenyl)-N'-phenylhydrazino, N'-(2-, 3- or 4-acetamidophenyl)-N'-phenylhydrazino, N'-(2-, 3- or 4-methylphenyl)-N'-(2-, 3- or 4-methylphenyl)hydrazino and N'-(2-, 3- or 4-methoxyphenyl)-N'-(2-, 3- or 4-methoxyphenyl) hydrazino groups.

More preferred groups of formula —NR$^1$R$^2$ include: the (1-methyl-1-phenylethyl)amino, [1-methyl-1-(2-, 3- or 4-methylphenyl)ethyl]amino, [1-methyl-1-(2-, 3- or 4-methoxyphenyl)ethyl]amino, [1-methyl-1-(2-, 3- or 4-fluorophenyl)ethyl]amino, [1-methyl-1-(2-, 3- or 4-chlorophenyl)ethyl]amino, [1-methyl-1-(2-, 3- or 4-hydroxyphenyl)ethyl]amino, [1-methyl-1-(2-, 3- or 4-aminophenyl)ethyl]amino, [1-methyl-1-(2-, 3- or 4-dimethylaminophenyl)ethyl]amino, [1-methyl-1-(2-, 3- or 4-acetamidophenyl)ethyl]amino, [1-methyl-1-(2,3-, 2,4-, 2,5-, 2,6-, 3,4-, 3,5- or 3,6-dimethoxyphenyl)ethyl]amino, (1,1-dimethyl-2-phenylethyl)amino, benzhydrylamino, [(2-, 3- or 4-), (2'-, 3'- or 4'-)-dimethylbenzhydryl]amino, [(2-, 3- or 4-), (2'-, 3'- or 4'-)-dimethoxybenzhydryl]amino, [(2-, 3- or 4-), (2'-, 3'- or 4'-)-difluorobenzhydryl]amino, [(2-, 3- or 4-), (2'-, 3'- or 4'-)-dihydroxybenzhydryl]amino, [(2-, 3- or 4-), (2'-, 3'- or 4'-)-diaminobenzhydryl]amino, [(2-, 3- or 4-), (2'-, 3'- or 4'-)-di(dimethylamino)benzhydryl]amino, (2-, 3- or 4-methylbenzhydryl)amino, (2-, 3- or 4-methoxybenzhydryl)amino, (2-, 3- or 4-fluorobenzhydryl) amino, (2-, 3- or 4-chlorobenzhydryl)amino, (2-, 3- or 4-hydroxybenzhydryl)amino, (2-, 3- or 4-aminobenzhydryl) amino, (2-, 3- or 4-dimethylaminobenzhydryl)amino, (1,1- diphenylethyl)amino, (1,2-diphenylethyl)amino, [2-(2-, 3- or 4-chlorophenyl)-1-phenylethyl]amino, [2-(2-, 3- or 4-fluorophenyl)-1-phenylethyl]amino, [2-(2-, 3- or 4-methylphenyl)-1-phenylethyl]amino, [2-(2-, 3- or 4-methoxyphenyl)-1-phenylethyl]amino, [1-(2-, 3- or 4-fluorophenyl)-2-(2-, 3- or 4-fluorophenyl)ethyl]amino, [1-(2-, 3- or 4-chlorophenyl)-2-(2-, 3- or 4-chlorophenyl)ethyl] amino, [1-(2-, 3- or 4-chlorophenyl)-2-(2-, 3- or 4-methoxyphenyl)ethyl]amino, [1-(2-, 3- or 4-methylphenyl)-2-(2-, 3- or 4-methylphenyl)ethyl]amino, [1-(2-, 3- or 4-hydroxyphenyl)-2-(2-, 3- or 4-hydroxyphenyl)ethyl]amino, [1-(2-, 3- or 4-aminophenyl)-2-(2-, 3- or 4-aminophenyl)ethyl]amino, [1-(2-, 3- or 4-dimethylaminophenyl)-2-(2-, 3- or 4-dimethylaminophenyl)ethyl]amino, [2-(2-, 3- or 4-fluorophenyl)-1-(2-, 3- or 4-methylphenyl)ethyl]amino, [2-(2-, 3- or 4-fluorophenyl)-1-(2-, 3- or 4-methoxyphenyl) ethyl]amino, [2-(2-, 3- or 4-hydroxyphenyl)-1-phenylethyl] amino, [2-(2-, 3- or 4-aminophenyl)-1-phenylethyl]amino, [2-(2-, 3- or 4-dimethylaminophenyl)-1-phenylethyl]amino, [1-(2-, 3- or 4-methoxyphenyl)-2-phenylethyl]amino, (1-methyl-1,2-diphenylethyl)amino, (2,2-diphenylethyl) amino, (1,1-diphenylethyl)amino, [1-(2-, 3- or 4-fluorophenyl)-1-(2-, 3- or 4-fluorophenyl)ethyl]amino, [1-(2-, 3- or 4-methylphenyl)-1-(2-, 3- or 4-methylphenyl) ethyl]amino, [1-(2-, 3- or 4-methoxyphenyl)-1-(2-, 3- or 4-methoxyphenyl)ethyl]amino, [1-(2-, 3- or 4-hydroxyphenyl)-1-phenylethyl]amino, [1-(2-, 3- or 4-aminophenyl)-1-phenylethyl]amino, [1-(2-, 3- or 4-dimethylaminophenyl)-1-phenylethyl]amino, tritylamino, (1-benzyl-2-phenylethyl)amino, (1-benzyl-1-methyl-2-phenylethyl)amino, N-benzyl-N-methylamino, N-benzyl-N-ethylamino, N-benzyl-N-isopropylamino, N-benzyl-N-isobutylamino, N-benzyl-N-t-butylamino, N-(2-, 3- or 4-fluorobenzyl)-N-isopropylamino, N-(2-, 3- or 4-chlorobenzyl)-N-isopropylamino, N-(2-, 3- or 4-methylbenzyl)-N-isopropylamino, N-(2-, 3- or 4-methoxybenzyl)-N-isopropylamino, N-(2-, 3- or 4-hydroxybenzyl)-N-isopropylamino, N,N-dibenzylamino, N-benzyl-N-(2-, 3- or 4-methoxybenzyl)amino, N-(2-, 3- or 4-fluorobenzyl)-N-(2-, 3- or 4-fluorobenzyl)amino, N-(2-, 3- or 4-methylbenzyl)-N-(2-, 3- or 4-methylbenzyl)amino, N-(2-, 3- or 4-methoxybenzyl)-N-(2-, 3- or 4-methoxybenzyl)amino, N-(2-, 3- or 4-hydroxybenzyl)-N-(2-, 3- or 4-hydroxybenzyl)amino, N-(2-, 3- or 4-aminobenzyl)-N-(2-, 3- or 4-aminobenzyl)amino, N-(2-, 3- or 4-dimethylaminobenzyl)-N-(2-, 3- or 4-dimethylaminobenzyl)amino, [bis(2- or 3-furyl)methyl] amino, [bis(2- or 3-thienyl)methyl]amino, [1,1-bis(2- or 3-thienyl)ethyl]amino, [(2- or 5-methyl-2- or 3-thienyl), (2- or 5-methyl-2- or 3-thienyl)methyl]amino, [1-(2- or 3-thienyl)-1-methylethyl]amino, [1-(2- or 5-methyl-2- or 3-thienyl)-1-methylethyl]amino, [1-(2- or 3-furyl)-1-methylethyl]amino, [1-(2- or 5-methyl-2- or 3-furyl)-1-methylethyl]amino, [1-(2- or 3-furyl)-2-(2- or 3-furyl)ethyl] amino, [1-(2- or 3-furyl)-1-methylethyl]amino, [1-(2- or 3-thienyl)-2-(2- or 3-thienyl)ethyl]amino, [1-(2- or 3-furyl)-2-phenylethyl]amino, [2-phenyl-1-(2- or 3-thienyl)ethyl] amino, [1-phenyl-2-(2- or 3-thienyl)ethyl]amino, [2-(2-, 3- or 4-methylphenyl)-1-(2- or 3-thienyl)ethyl]amino, [2-(2-, 3- or 4-chlorophenyl)-1-( 2- or 3-thienyl)ethyl]amino, [2-(2-, 3- or 4-fluorophenyl)-1-(2- or 3-thienyl)ethyl]amino, [2-(2-, 3- or 4-methoxyphenyl)-1-(2- or 3-thienyl)ethyl] amino, N-(2- or 3-thienylmethyl)-N-(2- or 3-thienylmethyl) amino, [1-(2-, 3- or 4-fluorophenyl)-2-(2- or 3-thienyl)ethyl] amino, N',N'-diphenylhydrazino, N'-(2-, 3- or 4-methylphenyl)-N'-phenylhydrazino, N'-(2-, 3- or 4-methoxyphenyl)-N'-phenylhydrazino, N'-(2-, 3- or 4-chlorophenyl)-N'-phenylhydrazino, N'-(2-, 3- or 4-fluorophenyl)-N'-phenylhydrazino, N'-(2-, 3- or 4-hydroxyphenyl)-N'-phenylhydrazino, N'-(2-, 3- or 4-aminophenyl)-N'-phenylhydrazino, N'-(2-, 3- or 4-dimethylaminophenyl)-N'-phenylhydrazino, N'-(2-, 3- or 4-acetamidophenyl)-N'-phenylhydrazino, N'-(2-, 3- or 4-methylphenyl)-N'-(2-, 3- or 4-methylphenyl)hydrazino and N'-(2-, 3- or 4-methoxyphenyl)-N'-(2-, 3- or 4-methoxyphenyl)hydrazino groups.

Still more preferred groups of formula —NR$^1$R$^2$ include: the (1-methyl-1-phenylethyl)amino, [1-methyl-1-(2-, 3- or 4-methylphenyl)ethyl]amino, [1-methyl-1-(2-, 3- or 4-methoxyphenyl)ethylamino, [1-methyl-1-(3,4- or 3,5-dimethoxyphenyl)ethyl]amino, [1-methyl-1-(2-, 3- or 4-fluorophenyl)ethyl]amino, [1-methyl-1-(2-, 3- or 4-chlorophenyl)ethyl]amino, [1-methyl-1-(2-, 3- or 4-hydroxyphenyl)ethylamino, [1-methyl-1-(2-, 3- or 4-dimethylaminophenyl)ethyl]amino, (1,1-dimethyl-2-phenylethyl)amino, benzhydrylamino, [(2-, 3- or 4-), (2'-, 3'- or 4'-)-dimethylbenzhydryl]amino, [(2-, 3- or 4-), (2'-, 3'- or 4'-)-dimethoxybenzhydryl]amino, [(2-, 3- or 4-), (2'-, 3'- or 4'-)-difluorobenzhydryl]amino, [(2-, 3- or 4-), (2'-, 3'- or 4'-)-dichlorobenzhydryl]amino, (2-, 3- or 4-methylbenzhydryl)amino, (2-, 3- or 4-methoxybenzhydryl)amino, (2-, 3- or 4-fluorobenzhydryl) amino, (2-, 3- or 4-chlorobenzhydryl)amino, (2-, 3- or 4-hydroxybenzhydryl)amino, (2-, 3- or 4-dimethylaminobenzhydryl)amino, (1,1-diphenylethyl) amino, (1,2-diphenylethyl)amino, [2-(2-, 3- or 4-chlorophenyl)-1-phenylethyl]amino, [2-(2-, 3- or 4-fluorophenyl)-1-phenylethyl]amino, [2-(2-, 3- or 4-methylphenyl)-1-phenylethyl]amino, [2-(2-, 3- or 4-methoxyphenyl)-1-phenylethyl]amino, N,N-dibenzylamino, N-(2-, 3- or 4-fluorobenzyl)-N-(2-, 3- or 4-fluorobenzyl)amino, N-(2-, 3- or 4-methylbenzyl)-N-(2-, 3- or 4-methylbenzyl)amino, N-(2-, 3- or 4-methoxybenzyl)-N-(2-, 3- or 4-methoxybenzyl)amino, [1-(2- or 3-thienyl)-1-(2- or 3-thienyl)methyl]amino, [2-phenyl-1-(2- or 3-thienyl)ethyl]amino, [1-methyl-1-(2- or 3-thienyl)ethyl] amino, [1-methyl-1-(2- or 5-methyl-2- or 3-thienyl)ethyl] amino, [1-methyl-1-(2- or 3-furylethyl]amino, [1-methyl-1-(2- or 5-methyl-2-furyl)ethyl]amino, N',N'-diphenylhydrazino, N'-(2-, 3- or 4-methoxyphenyl)-N'-phenylhydrazino, N'-(2-, 3- or 4-fluorophenyl)-N'-phenylhydrazino and N'-(2-, 3- or 4-methoxyphenyl)-N'-(2-, 3- or 4-methoxyphenyl)hydrazino.

The most preferred groups of formula —NR$^1$R$^2$ include: the (1-methyl-1-phenylethyl)amino, 1-methyl-1-(2-, 3- or 4-methylphenyl)ethyl]amino, [1-methyl-1-(2-, 3- or 4-methoxyphenyl)ethyl]amino, [1-methyl-1-(3,4- or 3,5-dimethoxyphenyl)ethyl]amino, [1-methyl-1-(2-, 3- or 4-fluorophenyl)ethyl]amino, [1-methyl-1-(2-, 3- or 4-chlorophenyl)ethyl]amino, [1-methyl-1-(2-, 3- or 4-hydroxyphenyl)ethyl]amino, [1-methyl-1-(2-, 3- or 4-dimethylaminophenyl)ethyl]amino, (1,1-dimethyl-2-phenylethyl)amino, benzhydrylamino, [(2-, 3- or 4-), (2'-, 3'- or 4'-)-dimethylbenzhydryl]amino, [(2-, 3- or 4-), (2'-, 3'- or 4'-)-dimethoxybenzhydryl]amino, [(2-, 3- or 4-), (2'-, 3'- or 4'-)-difluorobenzhydryl]amino, [(2-, 3- or 4-), (2'-, 3'- or 4'-)-dichlorobenzhydryl]amino, (2-, 3- or 4-methylbenzhydryl)amino, (2-, 3- or 4-methoxybenzhydryl)amino, (2-, 3- or 4-hydroxybenzhydryl)amino, (1,1-diphenylethyl)amino, [1-methyl-1-(2- or 3-thienyl)ethyl]amino, [1-methyl-1-(2- or 5-methyl-2- or 3-thienyl)ethyl]amino, [1-methyl-1-(2- or 3-furylethyl]amino and [1-methyl-1-(2- or 5-methyl-2- or 3-furyl)ethyl]amino groups.

The compounds of the present invention may, depending upon the nature of the substituent groups, contain one or more asymmetric carbon atoms in their molecules, and in this case can form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formula (I) and salts, esters and other functional derivatives thereof, in which:

(A) $R^1$ represents:
- a hydrogen atom;
- an alkyl group having 3 carbon atoms;
- a benzyl group;
- a substituted benzyl group having at least one substituent selected from the group consisting of alkyl groups having from 1 to 4 carbon atoms, alkoxy groups having from 1 to 4 carbon atoms, halogen atoms, amino groups, alkylamino groups having from 1 to 4 carbon atoms, dialkylamino groups in which each alkyl part has from 1 to 4 carbon atoms, hydroxy groups, alkoxycarbonyl groups having from 2 to 5 carbon atoms and aliphatic acylamino groups having from 1 to 5 carbon atoms;
- a furylmethyl group; or
- a thienylmethyl group;

(B) $R^2$ represents:
- a substituted alkyl group having from 1 to 4 carbon atoms and substituted by 1 or 2 substituents selected from the group consisting of phenyl groups, substituted phenyl groups, thienyl groups, furyl groups, substituted thienyl groups and substituted furyl groups, wherein the substituent or substituents on the phenyl group are selected from the group consisting of:
  alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups in which each alkyl part has from 1 to 4 carbon atoms, alkoxycarbonyl groups having from 2 to 5 carbon atoms and aliphatic acylamino groups having from 1 to 5 carbon atoms;
  and the substituent or substituents on the thienyl and furyl groups are selected from the group consisting of alkyl groups having from 1 to 4 carbon atoms;
- or a diarylamino group, in which each aryl part is a carbocyclic aromatic group which has from 6 to 10 ring carbon atoms and which is unsubstituted or is substituted by at least one substituent selected from the group consisting of
  alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups in which each alkyl part has from 1 to 4 carbon atoms, alkoxycarbonyl groups having from 2 to 5 carbon atoms and aliphatic acylamino groups having from 1 to 5 carbon atoms;

(C) $R^3$ represents: a carboxy group;
- an alkoxycarbonyl group having from 2 to 5 carbon atoms;
- a benzyloxycarbonyl group;
- a substituted benzyloxycarbonyl group at least one substituent selected from the group consisting of methyl, ethyl, methoxy and ethoxy groups and fluorine and chlorine atoms;
- a naphthylmethoxycarbonyl group;
- a diphenylmethoxycarbonyl group;
- an alkanoyloxyalkoxycarbonyl group in which the alkanoyl part has from 1 to 5 carbon atoms and the alkoxy part has from 1 to 4 carbon atoms;
- a cycloalkanecarbonyloxyalkoxycarbonyl group in which the cycloalkane part has from 5 to 7 carbon atoms and the alkoxy part has from 1 to 4 carbon atoms;
- an alkoxycarbonyloxyalkoxycarbonyl group in which each alkoxy part has from 1 to 4 carbon atoms,
- a cycloalkyloxycarbonyloxyalkoxycarbonyl group in which the cycloalkyl part has from 5 to 7 carbon atoms and the alkoxy part has from 1 to 4 carbon atoms;
- a (5-phenyl- or 5-alkyl-2-oxo-1,3-dioxolen-4-yl) methoxycarbonyl group in which the alkyl part has from 1 to 4 carbon atoms;
- a phthalidyloxycarbonyl group; or
- a group of formula —$CONHSO_2R^4$, wherein $R^4$ represents an alkyl group having from 1 to 4 carbon atoms.

More preferred compounds of the present invention are those compounds of formula (I) and salts, esters and other functional derivatives thereof, in which:

(D) $R^1$ represents:
- a hydrogen atom;
- an isopropyl group;
- a benzyl group;
- a substituted benzyl group having at least one substituent selected from the group consisting of methyl, ethyl, methoxy, ethoxy, hydroxy, ethoxycarbonyl, methoxycarbonyl, amino, methylamino, ethylamino, dimethylamino, diethylamino, formamido and acetamido groups and fluorine, chlorine and bromine atoms; or
- a thienylmethyl group;

(E) $R^2$ represents:
- a substituted alkyl group having from 1 to 4 carbon atoms and having 1 or 2 substituents selected from the group consisting of:
  phenyl groups;
  substituted phenyl groups having at least one substituent selected from the group consisting of methyl, ethyl, methoxy, ethoxy, hydroxy, methoxycarbonyl, ethoxycarbonyl, amino, methylamino, ethylamino, dimethylamino, diethylamino, formamido and acetamido groups and fluorine, chlorine and bromine atoms;
  furyl groups;
  methyl-substituted furyl groups
  thienyl groups; and
  methyl-substituted thienyl groups;
- a diphenylamino group; or
- a substituted diphenylamino group having at least one substituent selected from the group consisting of methyl, ethyl, methoxy, ethoxy, hydroxy, methoxycarbonyl, ethoxycarbonyl, amino, methylamino, ethylamino, dimethylamino, diethylamino, formamido and acetamido groups and fluorine, chlorine and bromine atoms;

(F) $R^3$ represents:

a carboxy group;

an alkoxycarbonyl group having from 2 to 5 carbon atoms;

a benzyloxycarbonyl group;

an alkanoyloxyalkoxycarbonyl group in which the alkanoyl part has from 1 to 5 carbon atoms and the alkoxy part has 1 or 2 carbon atoms;

a cycloalkanecarbonyloxyalkoxycarbonyl group in which the cycloalkane part has from 5 to 7 carbon atoms and the alkoxy part has 1 or 2 carbon atoms;

a methoxycarbonyl or ethoxycarbonyl group which is substituted by an alkoxycarbonyloxy group having from 2 to 5 carbon atoms;

a cycloalkyloxycarbonyloxyalkoxycarbonyl group in which the cycloalkyl part has from 5 to 7 carbon atoms and the alkoxy part has 1 or 2 carbon atoms;

a (5-phenyl-, 5-methyl- or 5-ethyl-2-oxo-1,3-dioxolen-4-yl)methoxycarbonyl group;

a phthalidyloxycarbonyl group; or a group of formula —$CONHSO_2R^4$, wherein $R^4$ represents a methyl group or an ethyl group.

Still more preferred compounds of the present invention are those compounds of formula (I) and salts, esters and other functional derivatives thereof, in which:

(G) $R^1$ and $R^2$ are independently selected from the group consisting of benzyl groups and substituted benzyl groups having at least one substituent selected from the group consisting of methyl, methoxy, hydroxy and acetamido groups and fluorine and chlorine atoms; or (H) $R^1$ represents a hydrogen atom, and $R^2$ represents:

a substituted alkyl group having from 1 to 4 carbon atoms and having 1 or 2 substituents selected from the group consisting of:

phenyl groups;

substituted phenyl groups having at least one substituent selected from the group consisting of methyl, methoxy, hydroxy, dimethylamino and acetamido groups and fluorine and chlorine atoms;

furyl groups and thienyl groups;

a diphenylamino group; or a substituted diphenylamino group having at least one substituent selected from the group consisting of methyl, methoxy, hydroxy, dimethylamino and acetamido and fluorine and chlorine atoms.

(I) $R^3$ represents a carboxy group, a methoxycarbonyl group, an ethoxycarbonyl group, a pivaloyloxymethoxycarbonyl group, an ethoxycarbonyloxymethoxycarbonyl group, a 1-(ethoxycarbonyloxy)ethoxycarbonyl group, an isopropoxycarbonyloxymethoxycarbonyl group, a 1-(isopropoxycarbonyloxy)ethoxycarbonyl group, a (5-methyl-2-oxo-1,3-dioxolen-4-yl)methoxycarbonyl group, a phthalidyloxycarbonyl group or a group of formula —$CONHSO_2R^4$ wherein $R^4$ represents a methyl group.

The most preferred compounds of the present invention are those compounds of formula (I) and salts, esters and other functional derivatives thereof, in which:

(J) $R^1$ represents a hydrogen atom, $R^2$ represents an alkyl group having from 1 to 3 carbon atoms and substituted with 1 or 2 substituents selected from the group consisting of:

substituted phenyl groups having at least one substituent selected from the group consisting of methyl, methoxy and hydroxy groups and fluorine and chlorine atoms;

furyl groups and thienyl groups;

(K) $R^3$ represents a carboxy group, a methoxycarbonyl group or an ethoxycarbonyl group;

(L) $R^2$ represents a 2-hydroxyisopropyl group or a 1-carboxyethyl group having at least one substituent selected from the group consisting of aryl groups as defined above and aromatic heterocyclic groups as defined above.

Specific examples of the compounds of the present invention include those of formula (I) in which $R^1$, $R^2$ and $R^3$ are as shown in the following Table 1. In the Table, the following abbreviations are used:

| | |
|---|---|
| Ac | acetyl |
| Bu | butyl |
| Bz | benzyl |
| Bzhy | benzhydryl |
| Et | ethyl |
| Fur | furyl |
| Me | methyl |
| Mod | (5-methyl-2-oxo-1,3-dioxolen-4-yl) methyl |
| Ph | phenyl |
| Phtn | phthalidyl |
| Piv | pivaloyl |
| Pr | propyl |
| iPr | isopropyl |
| Thi | thienyl |

TABLE 1

| Cpd No | $R^1$ | $R^2$ | $R^3$ |
|---|---|---|---|
| 1 | H | 1,2-diPhEt | COOH |
| 2 | H | Bzhy | COOH |
| 3 | H | 1,1-diPhEt | COOH |
| 4 | Bz | Bz | COOH |
| 5 | H | 1,2-di(2-Thi)Et | COOH |
| 6 | H | 1,2-bis(4-FPh)Et | COOH |
| 7 | H | 1,2-bis(4-MePh)Et | COOH |
| 8 | H | 1,2-bis(4-MeOPh)Et | COOH |
| 9 | H | 1,2-bis(4-ClPh)Et | COOH |
| 10 | H | di(2-Thi)CH— | COOH |
| 11 | H | 1,2-di(2-Thi)Et | COOMe |
| 12 | H | bis(4-FPh)CH— | COOH |
| 13 | H | bis(4-MePh)CH— | COOH |
| 14 | H | bis(4-MeOPh)CH— | COOH |
| 15 | H | 2-(4-MeOPh)-1-(2-Thi)Et | COOH |
| 16 | H | 2-(4-FPh)-1-(2-Thi)Et | COOH |
| 17 | H | 2-(4-MePh)-1-(2-Thi)Et | COOH |
| 18 | H | 2-(4-ClPh)-1-(2-Thi)Et | COOH |
| 19 | H | 1-(2-Fur)-2-PhEt | COOH |
| 20 | H | 2-Ph-1-(2-Thi)Et | COOH |
| 21 | H | di(3-Thi)CH— | COOH |
| 22 | H | 2-(4-MePh)-1-PhEt | COOH |
| 23 | H | 2-(4-FPh)-1-(4-MePh)Et | COOH |
| 24 | H | 2-(4-MeOPh)-1-PhEt | COOH |
| 25 | H | 2-(4-FPh)-1-(4-MeOPh)Et | COOH |
| 26 | H | 1-Bz-4-PhBu | COOH |
| 27 | H | 4-ClBzhy | COOH |
| 28 | H | 4-MeOBzhy | COOH |
| 29 | H | 4-FBzhy | COOH |
| 30 | H | 4-F-4'-MeOBzhy | COOH |
| 31 | H | 4-MeBzhy | COOH |
| 32 | H | 2-Ph-1-(2-Thi)Et | COOMe |
| 33 | H | 2-Ph-1-(2-Thi)Et | COOCH$_2$OPiv |
| 34 | H | 2-Ph-1-(2-Thi)Et | COOCH(Me)OCOOEt |
| 35 | H | 2-Ph-1-(2-Thi)Et | COOMod |
| 36 | H | 2-Ph-1-(2-Thi)Et | COONa |
| 37 | H | 1,1-diBzEt | COOH |
| 38 | H | 1,1-di(2-Thi)Et | COOH |
| 39 | H | 1,1-di(2-Thi)Et | COOMe |
| 40 | H | 1,1-di(2-Thi)Et | COOCH$_2$OPiv |
| 41 | H | 1,1-di(2-Thi)Et | COOCH(Me)OCOOEt |
| 42 | H | 1,1-di(2-Thi)Et | COOMod |
| 43 | H | 1,1-di(2-Thi)Et | COONa |
| 44 | H | Bzhy | COOMe |

TABLE 1-continued

| Cpd No | R¹ | R² | R³ |
|---|---|---|---|
| 45 | H | Bzhy | COOCH₂OPiv |
| 46 | H | Bzhy | COOCH(Me)OCOOEt |
| 47 | H | Bzhy | COOMod |
| 48 | H | Bzhy | COONa |
| 49 | H | 1,2-diPhEt | COOEt |
| 50 | H | 1,2-diPhEt | COOCH₂OPiv |
| 51 | H | 1,2-diPhEt | COOCH(Me)OCOOEt |
| 52 | H | 1,2-diPhEt | COOMod |
| 53 | H | 1,2-diPhEt | COONa |
| 54 | H | 1,2-diPhEt | COOPhth |
| 55 | H | 1,1-diPhEt | COOMe |
| 56 | H | 1,1-diPhEt | COOEt |
| 57 | H | 1,1-diPhEt | COOCH₂OPiv |
| 58 | H | 1,1-diPhEt | COOCH(Me)OCOOEt |
| 59 | H | 1,1-diPhEt | COOMod |
| 60 | H | 1,1-diPhEt | COOPhth |
| 61 | H | 1,1-diPhEt | COONa |
| 62 | H | 1-Bz-1-PhEt | COOH |
| 63 | H | 1,2-diPhPr | COOH |
| 64 | 4-HOBz | 4-HOBz | COOH |
| 65 | 4-FBz | 4-FBz | COOH |
| 66 | H | 1-Me-1-PhEt | COOH |
| 67 | H | 1-Me-1-(2-Thi)Et | COOH |
| 68 | H | 1-Me-1-(2-Thi)Et | COOMe |
| 69 | H | 1-Me-1-(2-Thi)Et | COOCH₂OPiv |
| 70 | H | 1-Me-1-(2-Thi)Et | COOCH(Me)OCOOEt |
| 71 | H | 1-Me-1-(2-Thi)Et | COOMod |
| 72 | H | 1-Me-1-PhEt | COOMe |
| 73 | H | 1-Me-1-PhEt | COOCH₂OPiv |
| 74 | H | 1-Me-1-PhEt | COOCH(Me)OCOOEt |
| 75 | H | 1-Me-1-PhEt | COOMod |
| 76 | H | 1,1-diMe-2-PhEt | COOH |
| 77 | H | 1-Me-1-(4-HOPh)Et | COOH |
| 78 | H | 1-Me-1-(4-FPh)Et | COOH |
| 79 | H | 1-Me-1-(4-NMe₂Ph)Et | COONa |
| 80 | H | di(2-Fur)CH— | COOH |
| 81 | H | 4,4'-diHOBzhy | COOH |
| 82 | H | 1,2-bis(4-HOPh)Et | COOH |
| 83 | H | 1,2-bis(4-HOPh)-1-MeEt | COOH |
| 84 | iPr | Bz | COOH |
| 85 | Et | Bz | COOH |
| 86 | Me | Bz | COOH |
| 87 | iBu | Bz | COOH |
| 88 | ipr | 4-FBz | COOH |
| 89 | ipr | 4-ClBz | COOH |
| 90 | iPr | 4-MeBz | COOH |
| 91 | iPr | 4-MeOBz | COOH |
| 92 | iPr | 4-HOBz | COOH |
| 93 | 2-ThiMe | 2-ThiMe | COOH |
| 94 | 2-ThiMe | Bz | COOH |
| 95 | H | Bzhy | COOEt |
| 96 | H | Bzhy | COOCH₂OPiv |
| 97 | H | Bzhy | COOCH(Me)OCOOEt |
| 98 | H | Bzhy | COOMod |
| 99 | H | Bzhy | COONa |
| 100 | Bz | Bz | COOMe |
| 101 | Bz | Bz | COOEt |
| 102 | H | di(2-Thi)CH— | COOMe |
| 103 | H | di(2-Thi)CH— | COOEt |
| 104 | H | di(2-Thi)CH— | COOCH₂OPiv |
| 105 | H | di(2-Thi)CH— | COOCH(Me)OCOOEt |
| 106 | H | di(2-Thi)CH— | COOMod |
| 107 | H | di(2-Thi)CH— | COONa |
| 108 | H | 2-(4-MePh)-1-PhEt | COOMe |
| 109 | H | 2-(4-MePh)-1-PhEt | COOEt |
| 110 | H | 2-(4-NePh)-1-PhEt | COOCH₂OPiv |
| 111 | H | 2-(4-MePh)-1-PhEt | COOCH(Me)OC |
| 112 | H | 2-(4-MePh)-1-PhEt | COOMod |
| 113 | H | 2-(4-MePh)-1-PhEt | COONa |
| 114 | H | 1,1-diPhEt | COOMe |
| 115 | H | 1-Me-1-PhEt | COOEt |
| 116 | H | 1-Me-1-PhEt | COOCH₂OPiv |
| 117 | H | 1-Me-1-PhEt | COOCH(Me)OCOOEt |
| 118 | H | 1-Me-1-PhEt | COOMod |
| 119 | H | 1-Me-1-PhEt | COONa |
| 120 | H | 1-Me-1-(2-Thi)Et | COOEt |
| 121 | H | 1-Me-1-(2-Thi)Et | COOCH₂OPiv |
| 122 | H | 1-Me-1-(2-Thi)Et | COOCH(Me)OCOOEt |
| 123 | H | 1-Me-1-(2-Thi)Et | COOMod |
| 124 | H | 1-Me-1-(2-Thi)Et | COONa |
| 125 | H | 1,1-diMe-2-PhEt | COOMe |
| 126 | H | 4,4'-diMeOBzhy | COOMe |
| 127 | H | 4-HOBzhy | COOH |
| 128 | H | 4-HOBzhy | COOMe |
| 129 | H | 4-HOBzhy | COOEt |
| 130 | H | 4-HOBzhy | COOCH₂OPiv |
| 131 | H | 4-HOBzhy | COOCH(Me)OCOOEt |
| 132 | H | 4-HCBzhy | COOMod |
| 133 | H | 4-HOBzhy | COONa |
| 134 | H | 4-MeOBzhy | COOEt |
| 135 | H | 4-MeOBzhy | COONa |
| 136 | H | 4-MeOBzhy | COOMe |
| 137 | H | 4-MeOBzhy | COOCH₂OPiv |
| 138 | H | 4-MeOBzhy | COOCH(Me)OCOOEt |
| 139 | H | 4-MeOBzhy | COOMod |
| 140 | H | 4-ClBzhy | COOH |
| 141 | H | 4-ClBzhy | COOMe |
| 142 | H | 1-(4-MeOPh)-1-MeEt | COOH |
| 143 | H | 1-(4-MeOPh)-1-MeEt | COOMe |
| 144 | H | 1-(4-MeOPh)-1-MeEt | COOEt |
| 145 | H | 1-(4-MeOPh)-1-MeEt | COOCH₂OPiv |
| 146 | H | 1-(4-MeOPh)-1-MeEt | COOCH(Me)CCOOEt |
| 147 | H | 1-(4-MeOPh)-1-MeEt | COOMod |
| 148 | H | 1-(4-MeOPh)-1-MeEt | COONa |
| 149 | H | 1-(3,5-diMeOph)-1-MeEt | COOH |
| 150 | H | 1-(3,5-diMeOph)-1-MeEt | COOMe |
| 151 | H | 1-(4-FPh)-1-MeEt | COOEt |
| 152 | H | 1-(4-FPh)-1-MeEt | COOCH₂OPiv |
| 153 | H | 1-(4-FPh)-1-MeEt | COOCH(Me)OCOOEt |
| 154 | H | 1-(4-FPh)-1-MeEt | COOMod |
| 155 | H | 1-(4-FPh)-1-MeEt | COONa |
| 156 | H | 1-(4-FPh)-1-MeEt | COOMe |
| 157 | H | 1-(4-AcNHPh)-1-MeEt | COOH |
| 158 | H | 1-(4-AcNHPh)-1-MeEt | COOMe |
| 159 | H | Ph₂N— | COOH |
| 160 | H | Ph₂N— | COOMe |
| 161 | H | Ph₂N— | COOEt |
| 162 | H | Ph₂N— | COOCH₂OPiv |
| 163 | H | Ph₂N— | COOCH(Me)OCOOEt |
| 164 | H | Ph₂N— | COOMod |
| 165 | H | Ph₂N— | COONa |
| 166 | H | 1-Me-1-(3-MeOPh)Et | COOH |
| 167 | H | 1-Me-1-(3-MeOPh)Et | COOMe |
| 168 | H | 1-Me-1-(2-MeOPh)Et | COOH |
| 169 | H | 1-Me-1-(2-MeOPh)Et | COOMe |
| 170 | H | 2,2-diPhEt | COOH |
| 171 | H | 3,3-diPhPr | COOH |
| 172 | H | Bzhy | COOEt |
| 173 | H | Bzhy | COOMe |
| 174 | H | Bzhy | COOCH₂OPiv |
| 175 | H | Bzhy | COOCH(Me)OCOOEt |
| 176 | H | Bzhy | COOMod |
| 177 | H | Bzhy | COONa |
| 178 | H | 1-Me-1-(2-Fur)Et | COOH |
| 179 | H | 1-Me-1-(2-Fur)Et | COOMe |
| 180 | H | 1-Me-1-PhEt | CONHSO₂Me |
| 181 | H | 1-Me-1-(2-Thi)Et | CONHSO₂Me |
| 182 | H | 1-Me-1-(4-MeOPh)Et | CONHSO₂Me |
| 183 | H | 1-Me-1-(3-Thi)Et | CONHSO₂Me |
| 184 | H | 1-Me-1-(4-NMe₂Ph)Et | CONHSO₂Me |
| 185 | H | 1-Me-1-(4-FPh)Et | CONHSO₂Me |
| 186 | H | 1-Me-1-(4-MePh)Et | CONHSO₂Me |
| 187 | H | 1-Me-1-(4-ClPh)Et | CONHSO₂Me |
| 188 | H | Bzhy | CONHSO₂Me |
| 189 | H | Bzhy | CONHSO₂Et |
| 190 | H | 1-Me-1-(4-NMe₂Ph)Et | COOH |
| 191 | H | 1-Me-1-(3-Thi)Et | COOH |
| 192 | H | 1-Me-1-(3,4-diMeOPh)Et | COOH |
| 193 | H | 1-Me-1-(4-ClPh)Et | COOH |
| 194 | H | 1-Me-1-(4-EtOPh)Et | COOH |
| 195 | H | 1-Et-1-PhPr | COOH |
| 196 | H | 1-Me-1-(4-MePh)Et | COOH |

TABLE 1-continued

| Cpd No | R¹ | R² | R³ |
|---|---|---|---|
| 197 | H | 1-Me-1-(3,4,5-triMeOPh)Et | COOMe |
| 198 | H | 1-HOMe-1-(4-MeOPh)Et | COOH |
| 199 | H | 1-HOOC-1-(4-MeOPh)Et | COOH |
| 200 | H | 1-Me-1-(3,4,5-triMeOPh)Et | COOH |
| 201 | H | 1-Me-1-(3,5-diNMe₂Ph)Et | COOH |

Of these, preferred compounds are Compounds No. 1, 2, 4, 5, 8, 9, 12, 14, 17, 19, 22, 27, 28, 29, 31, 33, 45, 48, 50, 64, 66, 67, 69, 73, 76, 78, 79, 82, 86, 88, 127, 130, 140, 142, 145, 149, 152, 157, 159, 166, 168, 178, 180, 182, 190, 191, 192, 193, 194, 195, 196, 197, 200 and 201, and more preferred compounds are Compounds No. 1, 2, 4, 5, 12, 14, 22, 27, 28, 31, 64, 66, 67, 76, 78, 127, 142, 145, 149, 159, 166, 168, 178, 190, 192, 194, 195, 197, 200 and 201.

The most preferred compounds are Compounds No.

1. 17-[N-(1,2-Diphenylethyl)carbamoyl]androsta-3,5-diene-3-carboxylic acid;
2. 17-[N-(Diphenylmethyl)carbaroyl]androsta-3,5-diene-3-carboxylic acid;
14. 17-[N-(4,4'-Dimethoxybenzhydryl)carbamoyl]androsta-3,5-diene-3-carboxylic acid;
66. 17-[N-(1-Methyl-1-phenylethyl)carbamoyl]androsta-3,5-diene-3-carboxylic acid;
67. 17-{N-[1-Methyl-1-(2-thienyl)ethyl]carbamoyl}androsta-3,5-diene-3-carboxylic acid;
78. 17-{N-[1-(4-Fluorophenyl)-1-methylethyl]carbamoyl}androsta-3,5-diene-3-carboxylic acid;
127. 17β-[N-(4-Hydroxybenzhydryl)carbamoyl]androsta-3,5-diene-3-carboxylic acid;
149. 17-{N-[1-(3,5-Dimethoxyphenyl)-1-methylethyl]carbamoyl}androsta-3,5-diene-3-carboxylic acid;
159. 17-[N-(Diphenylamino)carbamoyl]androsta-3,5-diene-3-carboxylic acid;
166. 17-{N-[1-(3-Methoxyphenyl)-1-methylethyl]carbamoyl}androsta-3,5-diene-3-carboxylic acid;
168. 17-{N-[1-(2-Methoxyphenyl)-1-methylethyl]carbamoyl}androsta-3,5-diene-3-carboxylic acid;
178. 17-[N-(α,α-Dimethylfurfuryl)carbamoyl]androsta-3,5-diene-3-carboxylic acid;
190. 17-{N-[1-(4-N,N-Dimethylaminophenyl)-1-methylethyl]carbamoyl}androsta-3,5-diene-3-carboxylic acid;
192. 17-{N-[1-(3,4-Dimethoxyphenyl)-1-methylethyl]carbamoyl}androsta-3,5-diene-3-carboxylic acid;
194. 17-{N-[1-(4-Ethoxyphenyl)-1-methylethyl]carbamoyl}androsta-3,5-diene-3-carboxylic acid; and
200. 17-{N-[1-Methyl-1-(3,4,5-trimethoxyphenyl)ethyl]carbamoyl}androsta-3,5-diene-3-carboxylic acid;
and pharmaceutically acceptable salts and esters thereof.

The compounds of the present invention may be prepared by a variety of methods well known for the preparation of known compounds of this type. For example, in general terms, they can be prepared by hydrolysing a compound of formula (VI):

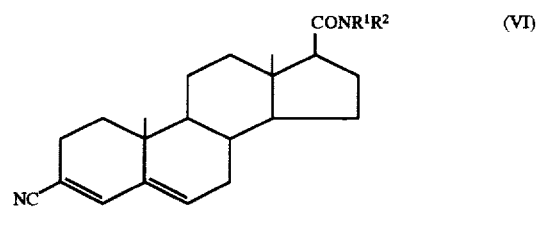

(wherein $R^1$ and $R^2$ are as defined above), to give the corresponding carboxylic acid of formula (Ia):

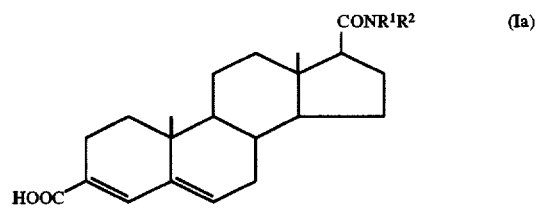

(wherein $R^1$ and $R^2$ are as defined above), and, if desired, converting the carboxy group at the 3-position to any other group represented by $R^3$ in the compound of formula (I), and, if desired, salifying or esterifying the compound of formula (Ia).

In more detail, starting from known or readily available starting materials, the compounds of the present invention may be prepared as illustrated in the following Reaction Scheme A:

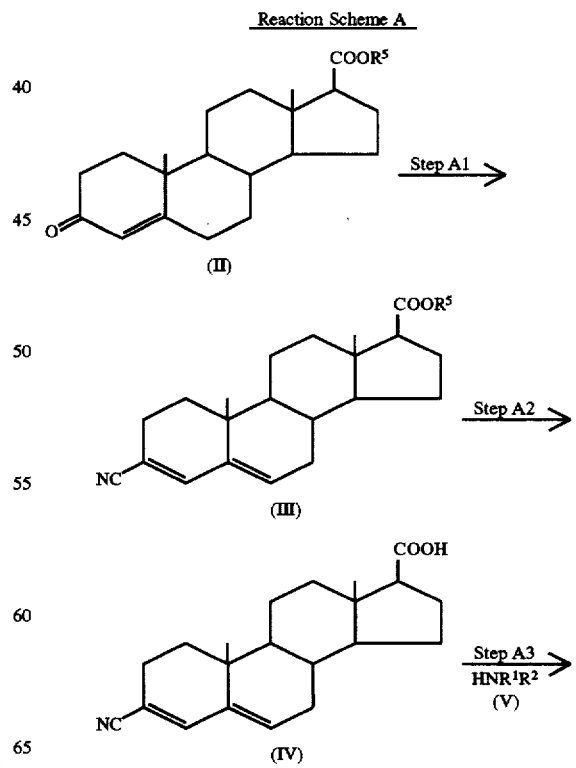

-continued
Reaction Scheme A

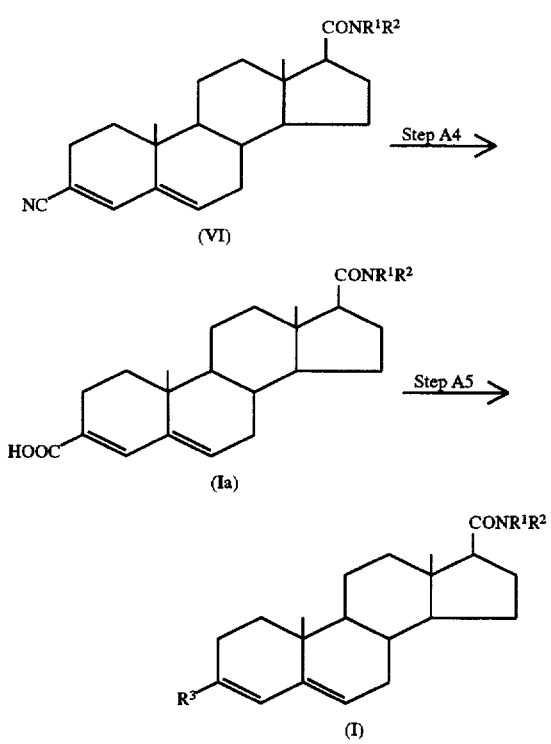

In the above formulae:

R¹, R² and R³ are as defined above; and

R⁵ represents a carboxy-protecting group, preferably an alkyl group having from 1 to 6 carbon atoms (such as those exemplified above in relation to R¹), or a group of formula —SiR$^a$R$^b$R$^c$ (wherein R$^a$, R$^b$ and R$^c$ are as defined above).

In Step A1 of this Reaction Scheme, a compound of formula (III) is prepared by reacting a compound of formula (II) with a dialkyl cyanophosphate (in which each alkyl group has from 1 to 6 carbon atoms) or a diaryl cyanophosphate (in which the aryl group may be as defined and exemplified above in relation to the substituents on R²) in an inert solvent in the presence of an alkali metal cyanide, and then reacting the resulting phosphoric acid ester with an acid.

There is no particular limitation on the alkali metal cyanide employed, and any alkali metal cyanides commonly used in reactions of this type may equally be employed here. Examples of such compounds include lithium cyanide, sodium cyanide and potassium cyanide, of which we prefer lithium cyanide.

There is no likewise particular limitation on the nature of the dialkyl or diaryl cyanophosphate employed, and examples include dimethyl cyanophosphate, diethyl cyanophosphate, diphenyl cyanophosphate and ditolyl cyanophosphate, of which we prefer diethyl cyanophosphate or diphenyl cyanophosphate.

The acid employed in the second part of this step is also not critical to the invention, and examples include Lewis acids, such as boron trifluoride, boron trifluoride-diethyl ether complexes, zinc chloride, aluminum chloride and tin tetrachloride, of which we prefer boron trifluoride or a boron trifluoride-diethyl ether complex.

The reaction is normally and preferably effected in the presence of a solvent, the nature of which is not critical, provided that it has no adverse effect upon the reaction and that it can dissolve the reagents, at least to some extent. Examples of suitable solvents include: aromatic hydrocarbons, such as benzene, toluene and xylene; ethers, such as diethyl ether, tetrahydrofursan and dioxane; and halogenated hydrocarbons, especially halogenated aliphatic hydrocarbons, such as methylene chloride and chloroform; of these, we prefer the ethers for the first reaction and aromatic hydrocarbons for the second reaction.

The reaction will take place over a wide range of temperatures, and the precise reaction temperature, chosen is not critical to the invention. In general, we find it convenient to carry out the first stage of the reaction at a temperature of from −20° to 50° C., more preferably from 0° to 30° C., and to carry out the second stage of the reaction at a temperature of from −50° to 50° C., more preferably from −20° to 30° C. The time required for the reaction may likewise vary widely, depending on many factors, notably the reaction temperature and the nature of the reagents. However, in most cases, a period of from 5 minutes to 5 hours, more preferably from 10 minutes to 1 hour, will normally suffice for the first stage of the reaction, whilst a period of from 30 minutes to 10 hours, more preferably from 1 hour to 5 hours, will normally suffice for the second stage of the reaction.

After completion of each of these reactions, the desired compounds can be collected from the reaction mixture by conventional means. For example, one suitable recovery procedure comprises: removing the solvent by distillation under reduced pressure; adding water to the residue; and extracting the mixture with a water-immiscible organic solvent, such as ethyl acetate. The extract is then dried over anhydrous magnesium sulfate, after which the solvent is removed by distillation, to give the desired compound. If necessary, the resulting compounds can be further purified by conventional means, such as recrystallization or the various chromatography techniques, notably column chromatography. However, if it also possible, in appropriate cases, to use the product of the first or second stage in the next reaction without any intermediate isolation or purification.

The compound of formula (II) and the compound of formula (II'), which are used as starting materials in Reaction Schemes A and B, respectively, are known or can be prepared according to known methods [e.g., as described in J. Med. Chem., 27, 1690 (1984); and J. Med. Chem., 29, 2298 (1986)].

In Step A2, a compound of formula (IV) is prepared by hydrolysing a compound of formula (III) with a base in an inert solvent.

There is no particular restriction on the nature of the base, provided that it has no adverse effect on other parts of the molecule. Examples of suitable bases include: alkali metal hydroxides, such as lithium hydroxide, sodium hydroxide and potassium hydroxide; and alkali metal carbonates, such as lithium carbonate, sodium carbonate and potassium carbonate; of these, we prefer the alkali metal hydroxides.

The reaction is normally and preferably effected in the presence of an inert solvent, the nature of which is not critical, provided that it has no adverse effect upon the reaction and that it can dissolve the reagents, at least to some extent. Examples of suitable solvents include: ethers, such as tetrahydrofuran and dioxane; alcohols, such as methanol, ethanol and butanol; glycols and glycol ethers, such as ethylene glycol, propylene glycol and ethylene glycol dimethyl ether; water; and mixtures of any two or more of these solvents; of these, we prefer the alcohols.

The reaction will take place over a wide range of temperatures, and the precise reaction temperature chosen is not critical to the invention. In general, we find it convenient to carry out the reaction at a temperature in the range of from 0° to 150° C., more preferably from 30° to 100° C. The time required for the reaction may likewise vary widely, depending on many factors, notably the reaction temperature and the nature of the reagents. However, in most cases, a period of from 1 hour to 50 hours, more preferably from 3 hours to 20 hours, will normally suffice.

After completion of the reaction, the desired compound can be collected from the reaction mixture by conventional means. For example, one suitable recovery procedure comprises: removing the solvent by distillation under reduced pressure; adding an aqueous acid solution, such as dilute hydrochloric acid, to the residue to make it acidic; extracting the resulting mixture with a water-immiscible organic solvent, such as methylene chloride; drying the extract over anhydrous magnesium sulfate; and removing the solvent by distillation, to give the desired compound. If necessary, the resulting compound can be further purified by conventional means, such as recrystallization or the various chromatography techniques, notably column chromatography.

Steps A1 and A2 can be carried out in the reverse order, if desired, that is, the introduction of a cyano group (Step A1) may take place before or after the hydrolysis (Step A2).

In Step A3, a compound of formula (VI) is prepared by reacting a compound of formula (IV) or a reactive derivative thereof with a compound of formula (V). This reaction may be carried out using conventional methods well known in the field of peptide synthesis, such as the acyl halide method, the azide method, the active ester method, the mixed acid anhydride method and the condensation method.

The acyl halide method may be carried out as follows: the compound of formula (IV) is reacted with halogenating agent in an inert solvent at a suitable temperature, and then the resulting compound is reacted with an amine compound of formula (V) according to the method as described in, for example, Japanese Patent Application Kokai No. Sho 54-145669 (=European Patent Publication No. 4949A), the disclosure of which is incorporated herein by reference.

Of the above methods, the azide method may be carried out as follows: the compound of formula (IV) or an ester thereof is reacted with hydrazine in an inert solvent (e.g. dimethylformamide) at a suitable temperature, preferably about room temperature, to give an amino acid hydrazide, which is then reacted with a nitrous acid compound to convert it to an azide compound. This azide compound is then reacted with an amine compound of formula (V).

There is no particular restriction on the nature or the nitrous acid compound employed, and any such compound commonly employed in this type of reaction may equally be used here. Examples of such compounds include: alkali metal nitrites, such as sodium nitrite; and alkyl nitrites, such as isoamyl nitrite.

The reaction of the hydrazide with the nitrous acid compound is preferably carried out in an inert solvent, the nature of which is not critical, provided that it has no adverse effect upon the reaction and that it can dissolve the reagents, at least to some extent. Examples of suitable solvents include: amides, such as dimethylformamide and dimethylacetamide; sulfoxides, such as dimethyl sulfoxide; and pyrrolidones, such as N-methylpyrrolidone. The subsequent step of reaction with an amine compound of formula (V) is usually carried out in one reaction mixture. The reactions will take place over a wide range of temperatures, and the precise reaction temperature chosen is not critical to the invention. In general, we find it convenient to carry out the reaction with the nitrous acid compound temperature in the range of from −50° to 0° C. and that with the amine compound of formula (V) at a temperature in the range of from −10° to 10° C. The time required for the reaction may likewise vary widely, depending on many factors, notably the reaction temperature and the nature of the reagents. However, in most cases, a period of from 5 minutes to 1 hour will normally suffice for the former step and a period of from 10 hours to 5 days will normally suffice for the latter step.

The active ester method may be carried out according to the method described in Japanese Patent Application Kokai No. Hei 2-172,999 (=European Patent Publication No. 478 066A), Japanese Patent Application Kokai No. Hei 4-288, 096 (=European Patent Publication No. 367 502A), or European Patent Publication No. 85301122, the disclosures of which are incorporated herein by reference, by reacting the compound of formula (IV) with an active esterifying agent to give an active ester, which is then reacted with the amine compound of formula (V).

These two reactions are preferably carried out in an inert solvent, the nature of which is not critical, provided that it has no adverse effect upon the reaction and that it can dissolve the reagents, at least to some extent. Examples of suitable solvents include: aromatic hydrocarbons, such as benzene, toluene and xylene; halogenated hydrocarbons, especially halogenated aliphatic hydrocarbons, such as methylene chloride and chloroform; ethers, such as diethyl ether and tetrahydrofuran; amides, such as dimethylformamide and dimethylacetamide; nitrites, such as acetonitrile; and amines, such as pyridine and triethylamine.

There is no particular restriction on the nature of the active esterifying agent employed, and examples of suitable compounds include: N-hydroxy compounds, such as N-hydroxysuccinimide, 1-hydroxybenzotriazole and N-hydroxy-5-norbornene-2,3-dicarboximide; and disulfide compounds, such as dipyridyl disulfide. The active esterification reaction is preferably carried out in the presence of a condensing agent, such as dicyclohexylcarbodiimide, carbonyldiimidazole or triphenylphosphine.

The reactions will take place over a wide range of temperatures, and the precise reaction temperature chosen is not critical to the invention. In general, we find it convenient to carry out the active esterification reaction at a temperature in the range of from −10° to 100° C. and the reaction between the active ester compound and the amine of formula (V) at about room temperature. The time required for the reactions may likewise vary widely, depending on many factors, notably the reaction temperature and the nature of the reagents. However, in most cases, a period of from 30 minutes to 80 hours will normally suffice for each reaction.

These reactions can also be carried out in the presence of dimethylaminopyridine.

The mixed acid anhydride method is carried out by preparing a mixed acid anhydride of the compound of formula (IV), and then reacting the mixed acid anhydride with the amine of formula (V).

The reaction for preparing the mixed acid anhydride can be accomplished by reacting the compound of formula (IV) with an agent capable of forming a mixed acid anhydride, for example: $C_1$–$C_6$ alkyl haloformate, such as ethyl chloroformate or isobutyl chloroformate; a $C_2$–$C_5$ alkanoyl halide, such as pivaloyl chloride; a di($C_1$–$C_6$) alkyl cyanophosphate, such as diethyl cyanophosphate; or a diaryl cyanophosphate, such as diphenyl cyanophosphate. The reaction is normally and preferably carried out in an inert solvent (e.g. one or more of the above-mentioned halogenated hydrocarbons, amides and ethers).

The reaction is also preferably carried out in the presence of an organic amine, such as triethylamine or N-methylmorpholine.

The reaction will take place over a wide range of temperatures, and the precise reaction temperature chosen is not critical to the invention. In general, we find it convenient to carry out the reaction at a temperature in the range of from −10° to 50° C. The time required for the reaction may likewise vary widely, depending on many factors, notably the reaction temperature and the nature of the reagents. However, in most cases, a period of from 30 minutes to 20 hours will normally suffice.

The reaction between the resulting mixed acid anhydride and the amine of formula (V) is preferably carried out in an inert solvent (e.g. one or more of the above-mentioned amides and ethers) in the presence of an organic amine, such as triethylamine, N,N-dimethylaminopyridine or N-methylmorpholine, at a suitable temperature, for example a temperature of from 0° to 80° C.; a period of from 1 to 30 hours will normally suffice for this reaction.

This reaction can also be carried out by reacting the compound of formula (IV), the amine compound of formula (V) and agent for forming the mixed acid anhydride simultaneously.

The condensation method may be carried out by reacting the compound of formula (IV) and the amine of formula (V) directly in the presence of a condensing agent, such as dicyclohexylcarbodiimide, carbonyldiimidizole or 1-methyl-2-chloro-pyridinium iodide/triethylamine. This reaction is carried out in the same manner as described above for preparing the active ester.

A compound of formula (VI) may also be prepared easily and in a good yield by reacting a compound of formula (IV) with an amine of formula (V) in an inert solvent in the presence of a base, and in the presence of a sulfonyl compound of formula:

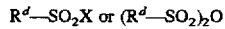

(wherein $R^d$ represents a $C_1$–$C_6$ alkyl group, a trifluoromethyl group, a camphyl group, an isocyano group or a $C_6$–$C_{10}$ aryl group which may be unsubstituted or may be substituted by a $C_1$–$C_6$ alkyl groups, $C_1$–$C_6$ alkoxy group or a halogen atom, and X represents a halogen atom.).

The reaction is normally and preferably effected in the presence of a solvent, the nature of which is not critical, provided that it has no adverse effect upon the reaction and that it can dissolve the reagents, at least to some extent. Examples of suitable solvents include: aliphatic hydrocarbons, such as hexane; aromatic hydrocarbons, such as benzene, toluene and xylene; ethers, such as diethyl ether, tetrahydrofuran, dioxane and dimethoxyethane; amides, such as dimethylformamide, dimethylacetamide and hexamethylphosphoric triamide; sulfoxides, such as dimethyl sulfoxide; and halogenated hydrocarbons, especially halogenated aliphatic hydrocarbons, such as methylene chloride, chloroform and dichloroethane; of these, we prefer the halogenated hydrocarbons.

Alternatively, a large excess of a liquid amine, such as triethylamine or pyridine, can be used also as solvent, and this may also serve as the base.

There is no particular limitation on the base employed, and any bases commonly used in reactions of this type may equally be employed here. Examples of such compounds include organic amines such as triethylamine, tripropylamine, tributylamine diisopropylethylamine, N,N-dimethylaniline, N,N-diethylaniline, pyridine, 4-(N,N-dimethylamino)pyridine, quinoline, 1,5-diazabicyclo[4.3.0] nona-5-ene (DBN) and 1,8-diazabicyclo[5.4.0]undec-7-ene (DBU), of which we prefer triethylamine, N,N-diethylaniline or pyridine. It is also possible to use two or more of the above bases simultaneously in this reaction.

Preferred compounds of formula $R^d$—$SO_2X$ include methanesulfonyl chloride, methanesulfonyl bromide, ethanesulfonyl chloride, propanesulfonyl chloride, benzenesulfonyl chloride, toluenesulfonyl chloride, 2,4,6-trimethylbenzenesulfonyl chloride, chlorobenzenesulfonyl chloride, bromobenzenesulfonyl chloride, methoxybenzenesulfonyl chloride, camphorsulfonyl chloride and chlorosulfonyl isocyanate, of which methanesulfonyl chloride, benzenesulfonyl chloride, toluenesulfonyl chloride and camphorsulfonyl chloride are more preferred.

Preferred compounds of formula $(R^d$—$SO_2)_2O$ include methanesulfonic acid anhydride, trifluoromethanesulfonic acid anhydride, ethanesulfonic acid anhydride, benzenesulfonic acid anhydride, toluenesulfonic acid anhydride, chlorobenzenesulfonic acid anhydride and camphorsulfonic acid anhydride, of which methanesulfonic acid anhydride, trifluoromethanesulfonic acid anhydride, benzenesulfonic acid anhydride and toluenesulfonic acid anhydride are more preferred.

The reaction will take place over a wide range of temperatures, and the precise reaction temperature chosen is not critical to the invention. In general, we find it convenient to carry out the reaction at a temperature of from −70° to 50° C., more preferably from −50° to 30° C. The time required for the reaction may likewise vary widely, depending on many factors, notably the reaction temperature and the nature of the reagents. However, in most cases, a period of from 15 minutes to 20 hours, more preferably from 30 minutes to 10 hours, will normally suffice for the reaction.

This reaction may more preferably be carried out by dissolving the compound of formula (IV) and from 1 to 10 equivalents of a base in an inert solvent, and then adding from 1 to 5 equivalents of the sulfonyl compound and from 1 to 5 equivalents of the amine of formula (V) either in that order or in the reverse order to this mixture.

The corresponding amide compounds of formula (VI) may also be obtained by the above reaction, but using dimethylformamide-phosphoryl oxychloride or a Vilsmeier reagent, such as chloromethylenedimethyliminium chloride, instead of the sulfonyl compound.

This reaction may more preferably be carried out by dissolving the compound of formula (IV) and from 1 to 5 equivalents of a Vilsmeier reagent in an inert solvent, and then adding from 1 to 10 equivalents of base and from 1 to 5 equivalents of the amine of formula (V) to this mixture.

In Step A4, the compound of formula (Ia), which is a compound of (I) in which $R^3$ represents a carboxy group, is prepared by hydrolizing the compound of formula (VI). If desired, this may be converted in Step A5 to any other group included in the definition of $R^3$ by protecting the carboxy group of the resulting carboxylic acid or by sulfonylamidating the resulting carboxylic acid.

The hydrolysis in Step A4 may be carried out by reacting the compound of formula (VI) with a base in an inert solvent. Examples of the base and inert solvent which may be employed are substantially the same as those used in Step A2 above; however, the preferred inert solvent is a glycol.

The reaction will take place over a wide range of temperatures, and the precise reaction temperature chosen is not critical to the invention. In general, we find it convenient to carry out the reaction at a temperature in the range of from 50° to 250° C., more preferably from 100° to 200° C. The time required for the reaction may likewise vary widely, depending on many factors, notably the reaction temperature and the nature of the reagents. However, in most cases, a period of from 3 hours to 50 hours, more preferably from 6 hours to 20 hours, will normally suffice.

After completion of the reaction, the desired compound can be collected from the reaction mixture by conventional means. For example, one suitable recovery procedure comprises: removing the solvent by distillation under reduced pressure; and adding an aqueous acid, such as dilute hydrochloric acid, to the residue to make it acidic. The resulting mixture may then be extracted with a water-immiscible organic solvent, such as methylene chloride. After the extract has been dried over anhydrous magnesium sulfate, the solvent is distilled off to give the desired compound. If necessary, the resulting compounds can be further purified by conventional means, such as recrystallization or the various chromatography techniques, notably column chromatography.

If $R^1$ or $R^2$ includes an alkanoylamino group, these may both be hydrolyzed in the course of this hydrolysis reaction. In this case, the corresponding amino compound can be converted to an alkanoyl amido compound, if desired, by conventional means. This reaction may be carried out by reacting the corresponding amino compound with an alkanoyl halide (such as acetyl chloride, acetyl bromide, propionyl chloride, butyryl chloride or isobutyryl chloride) or with a mixed acid anhydride with formic acid or acetic acid, or with an acid anhydride (such as acetic anhydride, propionic anhydride, butyric anhydride or isobutyric anhydride). The reaction may be carried out in the same manner as described for the reaction of the mixed acid anhydride with the amine in Step A3.

Also, if $R^1$ or $R^2$ includes an alkoxycarbonyl group, these may both be hydrolyzed to give a corresponding carboxylic acid. If desired, this can be converted to an alkyl ester by a conventional esterification reaction, which may be carried out in the same manner as the carboxy-protecting reaction described below, wherein about one equivalent of an esterification agent is used, and the resulting mixture is separated to obtain the desired compound.

The carboxy-protecting reaction may be carried out in the presence of an organic or inorganic base by methods well known in the art of synthetic organic chemistry. For example, it is normally and preferably carried out in an inert solvent, the nature of which is not critical, provided that it has no adverse effect upon the reaction and that it can dissolve the reagents, at least to some extent. Examples of suitable solvents include: amides, such as N,N-dimethylformamide or N,N-dimethylacetamide; halogenated hydrocarbons, especially halogenated aliphatic hydrocarbons, such as methylene chloride; and ethers, such as tetrahydrofuran or dioxane. Most preferably, it is carried out by reacting an alkali metal salt, such as the sodium salt or the potassium salt, of the corresponding carboxylic acid of formula (Ia) with a compound of formula (VIII):

$$R^6\text{---}Y \qquad (VIII)$$

wherein:

$R^6$ represents a $C_1$–$C_6$ alkyl group, a $C_1$–$C_6$ haloalkyl group, a $C_1$–$C_6$ hydroxyalkyl group, an alkoxyalkyl group in which the alkoxy and alkyl parts both have from 1 to 6 carbon atoms, an alkoxyalkoxyalkyl group in which the alkoxy and alkyl parts all have from 1 to 6 carbon atoms, a phenacyl group, an alkoxycarbonylalkyl group in which the alkoxy and alkyl parts both have from 1 to 6 carbon atoms, a $C_1$–$C_6$ cyanoalkyl group, a $C_1$–$C_6$ alkylthiomethyl group, a $C_6$–$C_{10}$ arylthiomethyl group, in which the aryl group may be as defined and exemplified above in relation to the aryl groups which may be substituents on the substituted alkyl groups represented by $R^1$, an alkylsulfonylalkyl group in which the alkyl parts both have from 1 to 6 carbon atoms and which is optionally substituted with a halogen atom, an arylsulfonylalkyl group, in which the aryl group may be as defined and exemplified above in relation to the aryl groups which may be substituents on the substituted alkyl groups represented by $R^1$, and is preferably unsubstituted or is an alkyl-substituted aryl group, and the alkyl part has from 1 to 6 carbon atoms, a $C_7$–$C_{13}$ aralkyl group, a $C_6$–$C_{10}$ aryl group, e.g. as defined and exemplified above in relation to aryl groups which may be substituents on the substituted alkyl groups represented by $R^1$, a group of formula —$SiR^aR^bR^c$ (wherein $R^a$, $R^b$ and $R^c$ are as defined and exemplified above), an alkanoyloxyalkyl group, in which the alkanoyl and alkyl parts both have from 1 to 6 carbon atoms, a cycloalkanecarbonyloxyalkyl group, in which the cycloalkane part has from 5 to 7 ring carbon atoms and the alkyl part has from 1 to 6 carbon atoms, an alkoxycarbonyloxyalkyl group, in which the alkoxy and alkyl parts all have from 1 to 6 carbon atoms, a cycloalkyloxycarbonyloxyalkyl group, in which the cycloalkyl part has from 5 to 7 ring carbon atoms and the alkyl part has from 1 to 6 carbon atoms, a [5-aryl- or 5-alkyl-2-oxo-1,3-dioxolen-4-yl]methyl group in which the aryl part may be as defined and exemplified above in relation to the aryl groups which may be substituents on the substituted alkyl groups represented by $R^1$, and is preferably unsubstituted or is an alkyl-substituted aryl group, and the alkyl part has from 1 to 6 carbon atoms, or a phthalidyl group; and Y represents a halogen atom (such as a chlorine, bromine or iodine atom) or a sulfonyloxy group (such as a methanesulfonyloxy, ethanesulfonyloxy, p-toluenesulfonyloxy or trifluoromethanesulfonyloxy group)

Alternatively, if the carboxy-protecting group is an alkyl group, the protecting reaction may be carried out by reacting the corresponding carboxylic acid with a di-$C_1$–$C_6$ alkyl sulfate, such as dimethyl sulfate or diethyl sulfate, or with a diazo $C_1$–$C_6$ alkane, such as diazomethane, diazoethane or diazopropane.

Examples of suitable bases include: alkali metal hydroxides, such as lithium hydroxide, sodium hydroxide and potassium hydroxide; alkali metal carbonates, such as lithium carbonate, sodium carbonate and potassium carbonate; and organic amines, such as triethylamine, N,N-dimethylaminopyridine or N-methylmorpholine.

The reaction will take place over a wide range of temperatures, and the precise reaction temperature chosen is not critical to the invention. In general, we find it convenient to carry out the reaction at a temperature in the range of from −20° to 50° C., more preferably from 0° to 30° 0C. The time required for the reaction may likewise vary widely, depending on many factors, notably the reaction temperature and the nature of the reagents. However, in most cases, a period of from 30 minutes to 5 hours, more preferably from 1 hour to 3 hours, will normally suffice.

After completion of the reaction, the desired compound can be collected from the reaction mixture by conventional means. For example, one suitable recovery procedure comprises: removing the solvent by distillation under reduced pressure; adding water to the residue; and extracting the resulting mixture with a water-immiscible organic solvent, such as ethyl acetate. The extract may then be dried over anhydrous magnesium sulfate, after which the solvent is distilled off to give the desired compound. If necessary, the resulting compounds can be further purified by conventional means, such as recrystallization or the various chromatography techniques, notably column chromatography.

The sulfonylamidation reaction may be carried out by reacting the corresponding carboxylic acid with an active esterifying agent to prepare an active ester, and then reacting this active ester with a compound of formula (IX):

$$MHNSO_2R^4 \qquad (IX)$$

wherein $R^4$ is as defined above; and M represents an alkali metal, such as sodium or potassium.

The reaction for preparing the active ester may be carried out in the same manner as described for the corresponding reaction in the Step A3 above. The compound of formula (IX) may be prepared by conventional procedures, for example by reacting the corresponding sulfonamide with an alkali metal alkoxide, such as sodium methoxide, sodium ethoxide or potassium t-butoxide, at a suitable temperature, e.g. at about room temperature, for an appropriate period, e.g. from 10 minutes to 3 hours, normally in an inert solvent, such as one of those suggested hereafter for the reaction between the active ester and the compound of formula (IX).

The reaction between the active ester and the compound of formula (IX) may be carried out by reacting these compounds in an inert solvent, the nature of which is not critical, provided that it has no adverse effect upon the reaction and that it can dissolve the reagents, at least to some extent. Examples of suitable solvents include: amides, such as N,N-dimethylformamide, N,N-dimethylacetamide or hexamethylphosphoric triamide; sulfoxides, such as dimethyl sulfoxide; and ethers, such as tetrahydrofuran and dioxane.

The reaction will take place over a wide range of temperatures, and the precise reaction temperature chosen is not critical to the invention. In general, we find it convenient to carry out the reaction at a temperature in the range of from −20° to 100° C., more preferably from 0° to 50° C. The time required for the reaction may likewise vary widely, depending on many factors, notably the reaction temperature and the nature of the reagents. However, in most cases, a period of from 5 minutes to 10 hours, more preferably from 10 minutes to 3 hours, will normally suffice.

After completion of the reaction, the desired compound can be collected from the reaction mixture by conventional means. For example, one suitable recovery procedure comprises: removing the solvent by distillation under reduced pressure; adding water to the residue; and extracting the resulting mixture with a water-immiscible organic solvent, such as ethyl acetate. After the extract has been dried over anhydrous magnesium sulfate, the solvent may be distilled off, to give the desired compound. If necessary, the resulting compounds can be further purified by conventional means, such as recrystallization or the various chromatography techniques, notably column chromatography.

Compounds in which $R^2$ represents an alkyl group having a hydroxy or carboxy substituent in addition to an aryl or aromatic substituent can be prepared by the same procedures as described in the above steps, but using the corresponding amine compound of formula (V) in Step A3; such compounds may also be prepared by oxidation in vivo as a result of the normal mammalian metabolism.

An alternative method of preparing the compound of formula (VI), prepared as described above in Step A3, is shown in the following Reaction Scheme B:

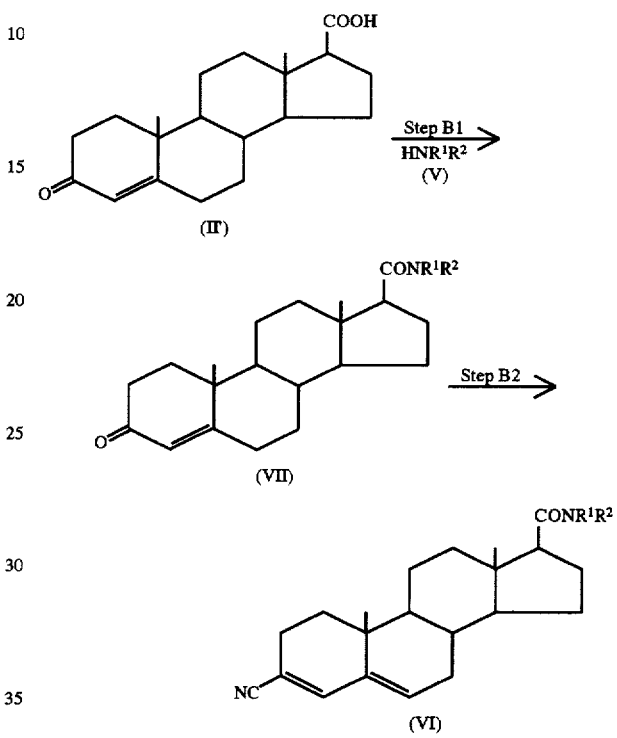

In the above formulae, $R^1$ and $R^2$ are as defined above.

In Step B1, a compound of formula (VII) is prepared by reacting a compound of formula (II') with an amine compound of formula (V). This reaction is essentially the same as, and may be carried out using the same reagents and reaction conditions as in, Step A3 of Reaction Scheme A.

In Step B2, a compound of formula (VI) is prepared by cyanizing the compound of formula (VII). This reaction is essentially the same as, and may be carried out using the same reagents and reaction conditions as in, Step A1 of Reaction Scheme A.

A compound (VI') of the formula:

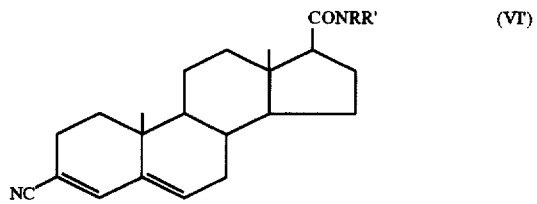

(wherein R and R' may be the same or different from each other and each represents a hydrogen atom or a $C_1$–$C_6$ alkyl group, such as those described and exemplified above in relation to $R^1$) can be prepared by reacting a compound (II') with a compound of formula (V')

$$HNRR' \qquad (V')$$

(wherein R and R' are as defined above) as described in Step B1 and Step B2 of Reaction Scheme B. This compound of formula (VI') can be converted by hydrolysis to a compound of formula (X):

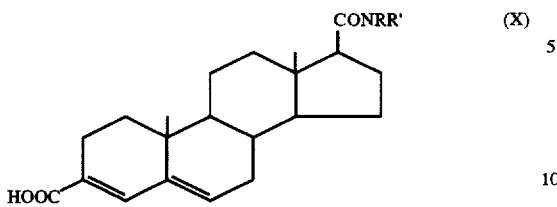

(wherein R and R' are as defined above). Accordingly, the compound of formula (VI') is a good intermediate for preparing the compound of formula (X). This reaction is essentially the same as that of Step A4 in Reaction Scheme A and may be carried out using the same reagents and reaction conditions.

Preferred compounds of formula (VI') are those in which R represents a hydrogen atom and R' represents a $C_1$–$C_4$ alkyl group, or in which R and R' are the same or different from each other and each represents a $C_1$–$C_4$ alkyl group, and more preferred compounds are those wherein R represents a hydrogen atom, and R' represents a t-butyl group, or R and R' are the same and each represents an ethyl or isopropyl group.

The compounds (VI) and (VI') are novel compounds useful as intermediates in the preparation of the compounds (I) and other active compounds of this type and thus also form part of the present invention.

The amine compound of formula (V), used as a starting material in various of the above reactions, is known or may be prepared by known methods [e.g. Synthesis, 593 (1976); J. Org. Chem., 36, 305 (1971); Angew. Chem., 82, 138 (1970); Synthesis, 24 (1978); Synthetic Commun., 18, 777 (1988); Synthetic Commun., 18, 783 (1988); Organic Reaction, 3, 337 (1946); Org. Synthesis, 51, 48 (1971); Tetrahedron, 30, 2151 (1974); J. Org. Chem., 37, 188 (1972)].

The amine compound of formula (V) wherein $R^2$ represents an alkyl group having a hydroxy or carboxy substituent in addition to an aryl or aromatic heterocyclic substituent can be prepared by conventional means well known in the art.

For example, certain of the amine compounds of formula (V) may be prepared as shown in the following Schemes C, D and E:

Reaction Scheme C

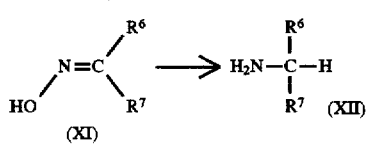

Reaction Scheme D

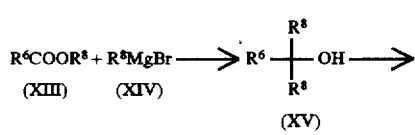

-continued
Reaction Scheme D

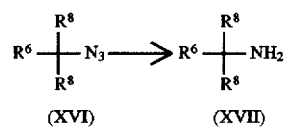

Reaction Scheme E

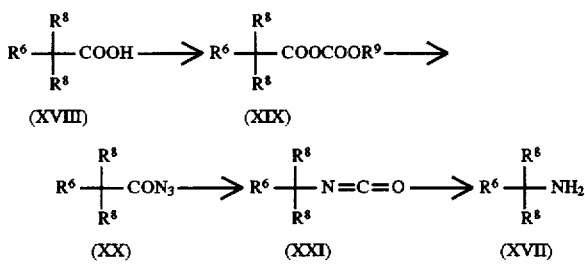

In these formulae:

$R^6$ and $R^7$ are the same or different and may be any of the aryl groups defined and exemplified above in relation to $R^2$;

$R^8$ represents an alkyl group having from 1 to 6 carbon atoms, as defined and exemplified above in relation to $R^1$; and $R^9$ represents an ester residue, for example as described above in relation to protecting groups for $R^3$, but preferably an alkyl group.

The reaction in Reaction Scheme C may be carried out using titanium trichloride, following the method described in Synthetic Communications, 18, page 777 (1988).

The reactions in Reaction Scheme D comprise a Grignard reaction, the azidation of the hydroxy group in the resulting compound (XV), and reduction, in that order, according to the method described in Synthesis page 24 (1978).

The reactions in Reaction Scheme E comprise an active carbonate generation reaction, an acid azide formation reaction, an isocyanate formation reaction, and hydrolysis of the isocyanate, in that order according to the method described in Journal of Organic Chemistry, 45, page 415 (1980).

A further alternative method of preparing the compounds of formula (I) from the compounds of formula (VI) is shown in the following Reaction Scheme F:

Reaction Scheme F

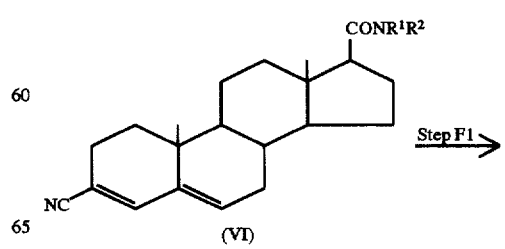

-continued
Reaction Scheme F

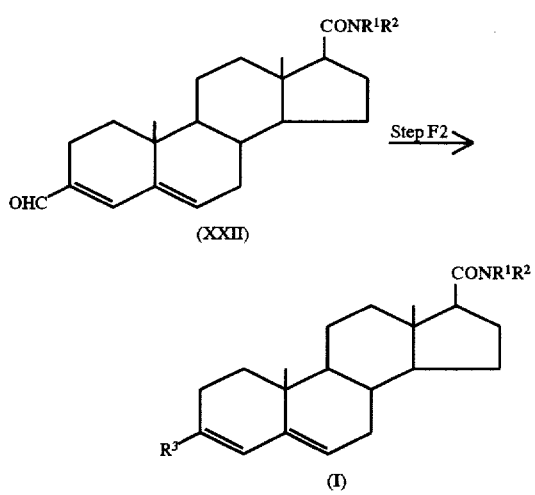

In the above formulae, $R^1$, $R^2$ and $R^3$ are as defined above.

In Step F1, a compound of formula (XXII) is prepared by reducing the cyano group of the compound of formula (VI) to yield an aldehyde group.

There is no particular limitation on the nature of the reducing agent employed, and any reducing agent commonly used in reactions of this type may equally be employed here. Examples of such reducing agents include reducing agents of the organic aluminum hydride type, such as di(isobutyl)aluminum hydride and di(methoxyethoxy) aluminum sodium dihydride.

The reaction is normally and preferably effected in the presence of a solvent, the nature of which is not critical, provided that it has no adverse effect upon the reaction and that it can dissolve the reagents, at least to some extent. Examples of suitable solvents include: aliphatic hydrocarbons, such as hexane and heptane; aromatic hydrocarbons, such as benzene, toluene and xylene; ethers, such as diethyl ether, diisopropyl ether, tetrahydrofuran, dimethoxyethane, diethylene glycol dimethyl ether and dioxane; halogenated hydrocarbons, especially halogenated aliphatic hydrocarbons, such as methylene chloride, tetrachloromethane, dichloroethane and chloroform; and amides, such as formamide, dimethylformamide, dimethylacetamide, hexamethylphosphoric triamide.

The reaction will take place over a wide range of temperatures, and the precise reaction temperature chosen is not critical to the invention. In general, we find it convenient to carry out the reaction at a temperature of from −100° to 30° C., more preferably from −10° to 20° C. The time required for the reaction may likewise vary widely, depending on many factors, notably the reaction temperature, the starting materials, the solvent employed and the nature of the reagents. However, in most cases, a period of from 30 minutes to 10 hours, more preferably from 1 hour to 5 hours, will normally suffice for the reaction.

After completion of the reaction, the desired compound (XXII) can be collected from the reaction mixture by conventional means. For example, one suitable recovery procedure comprises: adding water for hydrolysis; if appropriate, adjusting the pH of the mixture to a value in the range of from acidity or neutrality; if there is a precipitate, removing the precipitate by filtration; adding water to the residue; and extracting the mixture with a water-immiscible organic solvent, such as ethyl acetate. The extract is then dried over anhydrous magnesium sulfate, after which the solvent is removed by distillation, to give the desired compound. If necessary, the resulting compounds can be further purified by conventional means, such as recrystallization or the various chromatography techniques, notably column chromatography.

In Step F2, a compound of formula (I), which is a compound of the present invention, is prepared by oxidizing the aldehyde group of the compound of formula (XXII) to a carboxy group, and then protecting or sulfonylamidating the carboxy group obtained, in the same manner as described in Step A4 of Reaction Scheme A.

There is no particular limitation on the nature of the oxidizing agent employed, and any oxidizing agent commonly used in oxidizing reactions for converting an aldehyde group to a carboxy group may equally be employed here. Examples of such compounds include:

inorganic metal oxidizing agents, for example manganese oxides (such as potassium permanganate or manganese dioxide), ruthenium oxides (such as ruthenium tetraoxide), selenium compounds (such as selenium dioxide), iron compounds (such as iron chloride), osmium compounds (such as osmium tetraoxide), silver compounds (such as silver oxide), chromic acid compounds (such as potassium chromate, chromic anhydride-sulfuric acid complex or chromic anhydride-pyridine complex), and cerium compounds [such as cerium ammonium nitrate (CAN)]; and inorganic oxidizing agents, for example halogen molecules (such as chlorine molecules, bromine molecules and iodine molecules), periodic acids (such as sodium periodate), ozone, aqueous hydrogen peroxide, nitrous acid compounds (such as nitrous acid), chlorite compounds (such as potassium chlorite and sodium chlorite), and persulfuric acid compounds (such as potassium persulfate and sodium persulfate). Of these, the chromic acid compounds (such as potassium chromate, chromic anhydride-sulfuric acid complex and chromic anhydride-pyridine complex), cerium compounds [such as cerium ammonium nitrate (CAN)], chlorite compounds (such as potassium chlorite and sodium chlorite), and silver compounds (such as silver oxide) are more preferred.

The reaction is normally and preferably effected in the presence of a solvent, the nature of which is not critical, provided that it has no adverse effect upon the reaction and that it can dissolve the reagents, at least to some extent. Examples of suitable solvents include: aromatic hydrocarbons, such as benzene, toluene and xylene; ethers, such as diethyl ether, diisopropyl ether, tetrahydrofuran, dimethoxyethane, diethylene glycol dimethyl ether and dioxane; halogenated hydrocarbons, especially halogenated aliphatic hydrocarbons, such as methylene chloride, tetrachloromethane, dichloroethane and chloroform; amides, such as formamide, dimethylformamide, dimethylacetamide and hexamethylphosphoric triamide; sulfoxides, such as dimethylsulfoxide; alcohols, such as methanol, ethanol, propanol, isopropanol, butanol, isobutanol and isoamyl alcohol; dilute aqueous acids, such as aqueous sulfuric acid; aqueous bases, such as aqueous sodium hydroxide; water; ketones, such as acetone and methyl ethyl ketone; organic bases, such as pyridine; and nitriles, such as acetonitrile.

The reaction will take place over a wide range of temperatures, and the precise reaction temperature chosen is not critical to the invention. In general, we find it convenient to carry out the reaction at a temperature of from −10° to 30° C., more preferably from 0 to about room temperature. The time required for the reaction may likewise vary widely, depending on many factors, notably the reaction temperature, the starting materials, the solvent employed and the nature of the reagents. However, in most cases, a period of from 10 minutes to 10 hours, more preferably from 30 minutes to 5 hours, will normally suffice for the reaction.

In the oxidation reaction mentioned above, the reaction may be accelerated by adding a phase transfer catalyst, such as triethylbenzyl ammonium chloride or tributylbenzyl ammonium bromide, to the reaction mixture.

After completion of the reaction, the desired compound of formula (I) can be collected from the reaction mixture by conventional means. For example, one suitable recovery procedure comprises: if appropriate, adjusting the pH of the mixture to a value in the range of from acidity or neutrality; if there is precipitate, removing the precipitate by filtration; adding water to the residue; and extracting the mixture with a water-immiscible organic solvent, such as ethyl acetate. The extract is then dried over anhydrous magnesium sulfate, after which the solvent is removed by distillation, to give the desired compound. If necessary, the resulting compounds can be further purified by conventional means, such as recrystallization or the various chromatography techniques, notably column chromatography.

A still further alternative method of preparing the compound of this invention (I) from the compound (VII) is shown in the following Reaction Scheme G:

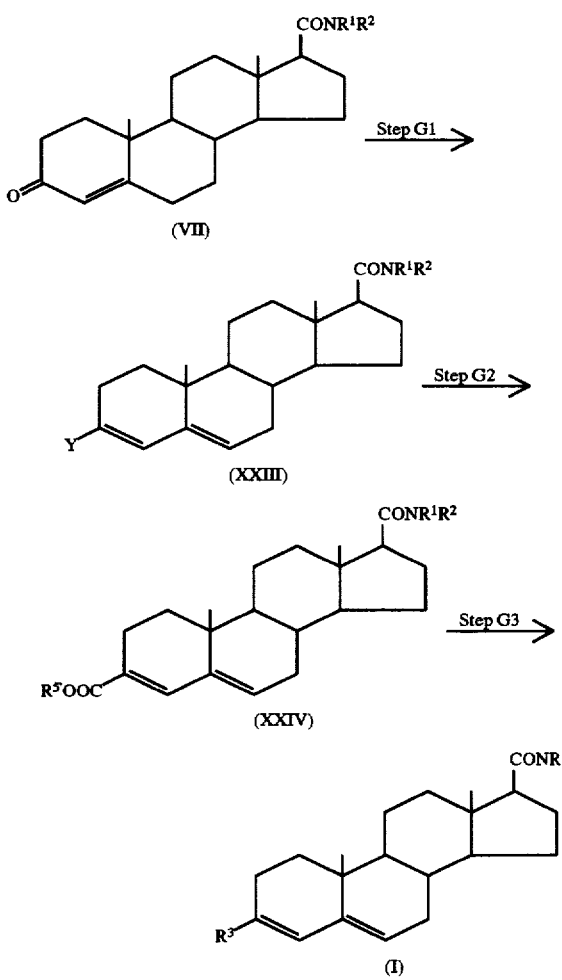

In the above formulae, $R^1$, $R^2$, $R^3$ and Y are as defined above, and $R^{5'}$ represents an alkyl group having from 1 to 10, preferably from 1 to 8, and more preferably from 1 to 6, carbon atoms, which may be the same as defined above in relation to $R^5$, or a cycloalkyl group having from 5 to 7 carbon atoms.

In Step G1, a compound of formula (XXIII) is prepared by replacing the carbonyl group of a compound of formula (VII) with the leaving group Y in the presence of base.

There is no particular limitation on the nature of the reagent used for the introduction of the group Y, and any reagent commonly used in reactions of this type may equally be employed here. Examples of such compounds include: trifluoromethanesulfonylating agents, such as trifluoromethanesulfonic anhydride and N,N-di(trifluoromethanesulfonyl)anilide; phosphorus trihalides, such as phophorus trichloride, phosphorus tribromide and phosphorus triiodide; phosphorus pentahalides, such as phosphorus pentachloride, phosphorus pentabromide and phosphorus pentaiodide; organic acyl halides, such as oxalyl chloride; and phosphorus oxyhalides, such as phosphorus oxychloride, phosphorus oxybromide and phosphorus oxyiodide. Of these, we prefer the trifluoromethanesulfonylating agents.

There is no particular limitation on the nature of the base employed, and any bases commonly used in reactions of this type may equally be employed here. Examples of such compounds include: organic amines such as triethylamine, tripropylamine, tributylamine, diisopropylethylamine, N,N-dimethylaniline, N,N-diethylaniline, pyridine, N-methylmorpholine, 2,6-di(t-butyl)-4-methylpyridine, 4-(N,N-dimethylamino)pyridine, quinoline, 1,5-diazabicyclo[4.3.0]nona-5-ene (DEN) and 1,8-diazabicyclo[5.4.0]undec-7-ene (DBU); and organic-metal bases, such as butyllithium, lithium diisopropylamide and lithium bis(trimethylsilyl)amide.

The reaction is normally and preferably effected in the presence of a solvent, the nature of which is not critical, provided that it has no adverse effect upon the reaction and that it can dissolve the reagents, at least to some extent. Examples of suitable solvents include: aromatic hydrocarbons, such as benzene, toluene and xylene; ethers, such as diethyl ether, diisopropyl ether, tetrahydrofuran, dimethoxyethane, diethylene glycol dimethyl ether and dioxane; halogenated hydrocarbons, especially halogenated aliphatic hydrocarbons, such as methylene chloride, tetrachloromethane, dichloroethane and chloroform; and amides, such as formamide, dimethylformamide, dimethylacetamide and hexamethylphosphoric triamide.

The reaction will take place over a wide range of temperatures, and the precise reaction temperature chosen is not critical to the invention. In general, we find it convenient to carry out the reaction at a temperature of from −50° to 30° C., more preferably from 0 to about room temperature. The time required for the reaction may likewise vary widely, depending on many factors, notably the reaction temperature, the starting materials, the solvent employed and the nature of the reagents. However, in most cases, a period of from 10 minutes to 8 hours, more preferably from 30 minutes to 5 hours, will normally suffice for the reaction.

After completion of this reaction, the desired compound of formula (XXIII) can be collected from the reaction mixture by conventional means. For example, one suitable recovery procedure comprises: if appropriate, neutralizing the pH; if there is a precipitate, removing the precipitate by filtration; adding water to the residue; and extracting the mixture with a water-immiscible organic solvent, such as ethyl acetate. The extract is then dried over anhydrous magnesium sulfate, after which the solvent is removed by distillation, to give the desired compound. If necessary, the resulting compounds can be further purified by conventional means, such as recrystallization or the various chromatography techniques, notably column chromatography.

In Step G2, a compound of formula (XXIV) is prepared by replacing the leaving group Y of the compound of formula (XXIII) with a protected carboxy group of formula —COOR$^{5'}$. This reaction may be carried out by reacting the compound of formula (XXIII) with carbon monoxide and an alcohol to provide the group R$^{5'}$, in the presence of a base and a palladium catalyst (and, if necessary, a phosphine) optionally in the presence of an additional solvent, following the procedure described in, for example, EP-0465123A, EP-0465141A or Journal of Medicinal Chemistry, 33, 943 (1990).

There is no particular limitation on the palladium catalyst employed, and any palladium catalyst commonly used in reactions of this type may equally be employed here. Examples of such catalysts include tetrakistriphenylphosphine palladium, bistriphenylphosphine palladium (II) diacetate and palladium chloride; of these we prefer bistriphenylphosphine palladium (II) diacetate.

There is no particular limitation on the phosphine employed, and any phosphine commonly used in reactions of this type may equally be employed here. Examples of such phosphines include triphenylphosphine and tributylphosphine; of these we prefer triphenylphosphine.

When the palladium catalyst and the phosphine are used simultaneously, they form a complex and participate in the reaction. For example, when palladium (II) diacetate is used as the palladium catalyst and triphenylphosphine is used as the phosphine, they form bis(triphenylphosphine) palladium (II) diacetate and participate in the reaction.

There is no particular limitation on the nature of the base employed, and any bases commonly used in reactions of this type may equally be employed here. Examples of such compounds include: organic amines such as triethylamine, tripropylamine, tributylamine, diisopropylethylamine, N,N-dimethylaniline, N,N-diethylaniline, pyridine, N-methylmorpholine, 2,6-di(t-butyl)-4-methylpyridine, 4-(N,N-dimethylamino)pyridine, quinoline, 1,5-diazabicyclo[4.3.0]nona-5-ene (DBN), 1,4-diazabicyclo[2.2.2]octane (DABCO) and 1,8-diazabicyclo[5.4.0]undec-7-ene (DBU); and organic metal bases, such as butyllithium, lithium diisopropylamide and lithium bis(trimethylsilyl) amide.

In this reaction, a quarternary ammonium salt (such as benzyltriethylammonium chloride or tetrabutylammonium chloride) or a crown ether (such as dibenzo-18-crown-6) can be added to the reaction mixture in order to allow the reaction to proceed more effectively.

The reaction is normally and preferably effected in the presence of a solvent, the nature of which is not critical, provided that it has no adverse effect upon the reaction and that it can dissolve the reagents, at least to some extent. However, an alcohol, such as methanol, ethanol, propanol, isopropanol, butanol, isobutanol, t-butanol, isoamyl alcohol, octanol or cyclohexanol, which will be the origin of the R$^{5'}$ group is essential. Accordingly, examples of suitable solvents include: the alcohol itself and mixtures of the alcohol and one or more of the solvents recommended for use in Step G1.

The reaction will take place over a wide range or temperatures, and the precise reaction temperature chosen is not critical to the invention. In general, we find it convenient to carry out the reaction at a temperature of from −10° to 50° C., more preferably from 0 to about room temperature. The time required for the reaction may likewise vary widely, depending on many factors, notably the reaction temperature, the starting materials, the solvent employed and the nature of the reagents. However, in most cases, a period of from 2 to 50 hours, more preferably from 3 to 30 hours, will normally suffice for the reaction.

After completion of this reaction, the desired compound of formula (XXIV) can be collected from the reaction mixture by conventional means. For example, one suitable recovery procedure comprises: if appropriate, neutralizing the pH; if there is a precipitate, removing the precipitate by filtration; adding water to the residue; and extracting the mixture with a water-immiscible organic solvent, such as ethyl acetate. The extract is then dried over anhydrous magnesium sulfate, after which the solvent is removed by distillation, to give the desired compound. If necessary, the resulting compounds can be further purified by conventional means, such as recrystallization or the various chromatography techniques, notably column chromatography.

In Step G3, the compound of formula (I) is prepared by hydrolizing the protected carboxy group of the compound of formula (XXIV) according to the method described in Step A2, and then optionally protecting or sulfonylamidating the carboxy group thus obtained according to the procedure described in Step A4.

Alternatively, treating the compound of formula (XXIII), obtained as described in Step G1, with a base and an alkanoic acid (such as formic acid or acetic acid), and then treating it with carbon dioxide, followed by hydrolysis of the product, can yield a compound corresponding to the compound of formula (XXIV) but which has a free carboxy group. If desired, the compound of formula (I) can be prepared by protecting or sulfonylamidating the carboxy group thus obtained according to the procedure described in Step A4.

There is no particular limitation on the nature of the base employed, and any bases commonly used in reactions for generating an anion may equally be employed here. Examples of such bases include: organic metal bases, such as butyllithium, sec-butyllithium, t-butyllithium, lithium diisopropylamide and lithium bis(trimethylsilyl)amide; and organic bases, such as triethylamine, tributylamine or diisopropylamine.

The reaction is normally and preferably effected in the presence of a solvent, the nature of which is not critical, provided that it has no adverse effect upon the reaction and that it can dissolve the reagents, at least to some extent. Examples of suitable solvents include: aromatic hydrocarbons, such as benzene, toluene and xylene; ethers, such as diethyl ether, diisopropyl ether, tetrahydrofuran, dimethoxyethane, diethylene glycol dimethyl ether and dioxane; halogenated hydrocarbons, especially halogenated aliphatic hydrocarbons, such as methylene chloride, tetrachloromethane, dichloroethane and chloroform; amides, such as formamide, dimethylformamide, dimethylacetamide and hexamethylphosphoric triamide; and sulfoxides, such as dimethyl sulfoxide.

The reaction will take place over a wide range of temperatures, and the precise reaction temperature chosen is not critical to the invention. In general, we find it convenient to carry out the reaction at a temperature of from −100° to 30° C., more preferably from −78° to 0° C. The time required for the reaction may likewise vary widely, depending on many factors, notably the reaction temperature, the starting materials, the solvent employed and the nature of the reagents. However, in most cases, a period of from 1 to 10 hours, more preferably from 2 to 8 hours, will normally suffice for the reaction.

After completion of this reaction, the desired compound of formula (I) can be collected from the reaction mixture by conventional means. For example, one suitable recovery procedure comprises: adding water for hydrolysis; if appropriate, neutralizing the pH; if there is a precipitate, removing the precipitate by filtration; adding water to the residue; and extracting the mixture with a water-immiscible organic solvent, such as ethyl acetate. The extract is then dried over anhydrous magnesium sulfate, after which the solvent is removed by distillation, to give the desired compound. If necessary, the resulting compounds can be further purified by conventional means, such as recrystallization or the various chromatography techniques, notably column chromatography.

BIOLOGICAL ACTIVITY

The novel steroid derivatives of the present invention have shown an excellent ability to inhibit testosterone 5α-reductase, combined with a low toxicity, and are thus useful for the prevention and therapy of prostatic hypertrophy as well as other disorders arising from excess levels of 5α-dihydrotestosterone.

This activity is demonstrated by the following Tests, in which the compounds of the present invention are identified by the one of the subsequent Examples in which its preparation is illustrated. Prior art Compound B is 17β-t-butylcarbamoylandrosta-3,5-diene-3-carboxylic acid, as previously discussed.

(1) Preparation of 5α-Reductase from Rat Prostate

The ventral prostate glands of adult male rats (body weight 300 to 350 g: Sprague-Dawley strain) were cut up with scissors, and about a 5-fold amount relative to the tissue of a buffer was added to the tissue. The buffer used was a 20 mM potassium phosphate buffer containing 0.33M sucrose, 1 mM dithiothreitol, 50 μM reduced nicotine amidoadenine dinucleotide phosphate (NADPH) and 0.001% by weight phenylmethylsulfonyl fluoride (PMSF)]. The tissue was then homogenized, first with a Polytron (trade mark) homogenizer (manufactured by Kinematica, GmbH) and then with a Teflon-glass homogenizer (Teflon is a trade mark). The suspension of homogenized prostate tissue was then centrifuged (140000×g, 60 minutes), and the sediment was suspended by adding approximately a 5-fold amount of the above buffer. The suspension was again centrifuged (140000×g, 60 minutes). The resulting sediment was used as the rat 5α-reductase. This was adjusted to a protein concentration of 30 to 40 mg/ml by the addition of the buffer described above, and the preparation was then stored frozen at −80° C. Measurement of the amount of protein was performed using the Bio-Rad Protein Assay method, and bovine γ-globulin (Cohn Fraction II, manufactured by Sigma) was used for the protein reference standard.

(2) Rat 5α-Reductase Inhibition Test

5 μl of a test compound was dissolved in dimethyl sulfoxide or ethanol (final concentration of test compound: $10^{-8}$M), and the resulting solution, 0.5 ml of a 40 mM potassium phosphate buffer (pH 6.5) containing rat 5α-reductase prepared as described above (amount of protein: 1 mg), 1 μM [$^{14}$C]-testosterone, 1 mM dithiothreitol and 500 μM NADPH were placed in a test tube. The mixture was then incubated at 37° C. for 15 to 30 minutes. Testing was also performed on a control group by adding solvent only. Following incubation, 2 ml of ethyl acetate, containing 10 μg each of testosterone, 5α-dihydrotestosterone and androstenedione, were added to stop the reaction. The reaction mixture was centrifuged (1400×g, 5 minutes), and then the ethyl acetate fraction was transferred to a separate test tube and evaporated to dryness in the presence of circulating nitrogen gas. The steroid was dissolved in 40 μl of ethyl acetate and spotted onto a thin layer chromatographic plate (LK5DF silica plate, manufactured by Whatman). The plate was then developed twice at room temperature with a mixture of ethyl acetate and cyclohexane (1:1 by volume). The steroid fraction was identified with ultraviolet light and stained using an aqueous solution of 1% w/v cesium sulfate and 10% w/v sulfuric acid. The radioactivity profiles of the thin layer chromatographic plate were measured using a bio-image analyzer (manufactured by Fuji Photo Film). Enzyme activity was expressed as the proportion of [$^{14}$C]-5α-dihydrotestosterone that was converted from the [$^{14}$C]-testosterone (conversion rate (%)) added. In on, the rat 5α-reductase inhibitory activity of the specimen was determined using the following formula.

Rat 5α-Reductase Inhibitory Activity=(conversion rate of test group)/(conversion rate of control group)×100 (%)

The results are shown in the following Table 2.

TABLE 2

| Compound of Ex. No. | Inhibitory Activity | ID$_{50}$ |
|---|---|---|
| 1 | 70.6 | — |
| 2 | 70.6 | $3.6 \times 10^{-9}$ |
| 6 | 89.4 | — |
| 7 | 70.3 | $4.2 \times 10^{-9}$ |
| 9 | 77.9 | $4.3 \times 10^{-9}$ |
| 11 | 73.5 | — |
| 12 | 74.0 | — |
| 13 | 84.3 | — |
| 15 | 73.3 | $4.96 \times 10^{-9}$ |
| 16 | 81.7 | — |
| 21 | 84.9 | — |
| 25 | 79.3 | — |
| Compound B | 28.1 | $3.37 \times 10^{-8}$ |

As can be seen from the above results, the compounds of the present invention have excellent inhibitory activity against the action of 5α-reductase, which is an order of magnitude higher than the closest prior art compound, which itself is under investigation for human therapeutic use.

The compounds of the present invention may be administered by any suitable route and may be formulated, as is well known in the art, in pharmaceutical compositions with conventional adjuvants, carriers, diluents or other active compounds, depending upon the nature of the disorder to be treated and the route of administration. For example, for oral administration the compounds may be formulated as tablets, capsules, granules, powders and syrups; and for parenteral administration they may be formulated as injections and suppositories. These pharmaceutical preparations can be prepared by conventional means using such additives as vehicles, binders, disintegrators, lubricants, stabilizers and corrigents. Although the dosage may be vary depending upon symptoms, body weight and age of the patients, as well as the nature and severity of the disorder to be treated or prevented, the usual daily dosage for an adult is from 0.01 to 1000 mg, preferably from 0.1 to 100 mg, which may be administered as a single dose or in divided doses, several times a day.

The invention is further illustrated by the following Examples, which illustrate the preparation of certain of the compounds of the present invention, and by the subsequent Preparations, which illustrate the preparation of certain of the starting materials used in these Examples.

EXAMPLE 1

17β-[N-(Diphenylmethyl)carbamoyl]androsta-3,5-diene-3-carboxylic acid (Compound No. 2)

1(a) Methyl 3-cyanoandrosta-3,5-diene-17β-carboxylate 3.0 g of lithium cyanide and 16 ml of diethyl cyanophosphate were dissolved in 200 ml of dry tetrahydrofuran, and 10 g of methyl 3-oxo-4-androstene-17β-carboxylate were added little by little at room temperature to the resulting solution. The reaction mixture was stirred at room temperature for 15 minutes, after which the tetrahydrofuran was removed by distillation under reduced pressure. The residue was dissolved in 300 ml of a 1:1 by volume mixture of ethyl acetate and benzene, and the resulting solution was washed four times with water and then once with a saturated aqueous solution of sodium chloride. It was then dried over anhydrous magnesium sulfate, and concentrated by evaporation under reduced pressure. The resulting residue was dissolved in 100 ml of dry benzene, and 2 ml of a boron trifluoride-diethyl ether complex was added to the resulting solution, which was then stirred at room temperature for 3 hours. At the end of this time, the reaction mixture was diluted with 300 ml of diethyl ether. The diluted mixture was washed with water, with an aqueous solution of sodium hydrogencarbonate and with a saturated aqueous solution of sodium chloride, in that order, after which it was dried over anhydrous magnesium sulfate, and then concentrated by evaporation under reduced pressure. The resulting residue was subjected to column chromatography through 100 g of silica gel using a gradient elution method, with mixtures of ethyl acetate and hexane in ratios ranging from 4:96 to 12:88 by volume as the eluent, to give 9.5 g of the title compound.

Nuclear Magnetic Resonance Spectrum (CDCl$_3$), δ ppm:
0.70 (3H, singlet);
0.93 (3H, singlet);
0.90–2.50 (18H, multiplet);
3.67 (3H, singlet);
5.77 (1H, triplet, J=3 Hz);
6.65 (1H, singlet).

Infrared Absorption Spectrum (KBr), $v_{max}$ cm$^{-1}$: 2940, 2885, 2205, 1729, 1635, 1603, 1436, 1200, 1161, 1058, 935, 652, 541.

1(b) 3-Cyanoandrosta-3,5-diene-17β-carboxylic acid 8.8 g of methyl 3-cyanoandrosta-3,5-diene-17β-carboxylate [prepared as described in step (a) above] and 4.3 g of potassium hydroxide were dissolved in a mixture of 20 ml of water and 200 ml of methanol, and the resulting solution was heated under reflux for 10 hours. At the end of this time, the methanol in the reaction mixture was removed by distillation under reduced pressure, the mixture was made acidic by the addition of dilute aqueous hydrochloric acid and extracted three times with methylene chloride. The organic extract was washed with water and then with a saturated aqueous solution of sodium chloride and dried over anhydrous magnesium sulfate. It was then concentrated by evaporation under reduced pressure. The resulting residue was subjected to column chromatography through 150 g of silica gel using a gradient elution method, with mixtures of acetone and methylene chloride in ratios ranging from 2:98 to 16:84 by volume as the eluent, to give 7.1 g of the title compound.

Nuclear Magnetic Resonance Spectrum (CDCl$_3$), δ ppm:
0.78 (3H, singlet);
0.94 (3H, singlet);
0.90–2.50 (18H, multiplet);
5.77 (1H, triplet, J=3 Hz);
6.65 (1H, singlet).

Infrared Absorption Spectrum (KBr), $v_{max}$ cm$^{-1}$: 2968, 2944, 2855, 2205, 1698, 1634, 1603, 1421, 1296, 1238, 932, 730, 650.

1(c) N-(Diphenylmethyl)-3-cyanoandrosta-3,5-diene-17β-carboxamide 1.0 g of 3-cyanoandrosta-3,5-diene-17β-carboxylic acid [prepared as described in step (b) above], 1.0 ml of diphenylmethylamine and 1.0 ml of triethylamine were dissolved in 10 ml of dry methylene chloride, and 0.75 ml of diethyl cyanophosphate was added to the resulting solution at room temperature. The reaction mixture was stirred at room temperature overnight, after which it was diluted with 100 ml of methylene chloride, and then washed with 1N aqueous hydrochloric acid, with water, with an aqueous solution of sodium hydrogencarbonate and with a saturated aqueous solution of sodium chloride, in that order. The solution was then dried over anhydrous magnesium sulfate, after which it was concentrated by evaporation under reduced pressure. The resulting residue was subjected to column chromatography through 40 g of silica gel using a gradient elution method, with mixtures of acetone and methylene chloride in ratios ranging from 1:99 to 4:96 by volume as the eluent, to give 0.85 g of the title compound.

Nuclear Magnetic Resonance Spectrum (CDCl$_3$), δ ppm:
0.70 (3H, singlet);
0.92 (3H, singlet);
0.90–2.00 (13H, multiplet);
2.18–2.36 (5H, multiplet);
5.76 (1H, triplet, J=2 Hz);
5.88 (1H, doublet, J=8 Hz);
6.29 (1H, doublet, J=8 Hz);
6.64 (1H, singlet);
7.21–7.36 (10H, multiplet).

Infrared Absorption Spectrum (KBr), $v_{max}$ cm$^{-1}$: 2967, 2950, 2912, 2205, 1664, 1636, 1603, 1485, 1449, 1199, 757, 697.

1(d) 17β-[N-(Diphenylmethyl)carbamoyl]androsta-3,5-diene-3-carboxylic acid 0.8 g of N-diphenylmethyl-3-cyanoandrosta-3,5-diene-17β-carboxamide [prepared as described in step (c) above] and 6.0 g of potassium hydroxide were dissolved in a mixture of 14 ml of water and 20 ml of ethylene glycol, and then the mixture was heated under reflux for 16 hours. At the end of this time, the reaction mixture was cooled to room temperature and made acidic by the addition of dilute aqueous hydrochloric acid. The mixture was then extracted three times with methylene chloride. The combined organic extracts were washed with water and with a saturated aqueous solution of sodium chloride, in that order and dried over anhydrous magnesium sulfate. The mixture was then concentrated by evaporation under reduced pressure. The resulting residue was subjected to column chromatography through 35 g of silica gel using a gradient elution method, with mixtures of acetone and methylene chloride in ratios ranging from 2:98 to 12:88 by volume as the eluent, to give 650 mg of the title compound.

Nuclear Magnetic Resonance Spectrum (CDCl$_3$), δ ppm:
0.71 (3H, singlet);
0.91 (3H, singlet);
0.90–2.60 (18H, multiplet);
5.86 (1H, triplet, J=3 Hz);
5.89 (1H, doublet, J=8 Hz);
6.30 (1H, doublet, J=8 Hz);

7.13 (1H, singlet);

7.20–7.40 (10H, multiplet).

Infrared Absorption Spectrum (KBr), $v_{max}$ cm$^{-1}$: 3337, 2942, 1710, 1698, 1674, 1634, 1530, 1496, 1367, 12.0, 1203, 1170, 755, 700, 641.

EXAMPLE 2

17β-{N-[1-(4-Methoxyphenyl)-1-methylethyl]carbamoyl}androsta-3,5-diene-3-carboxylic acid
(Compound No. 142)

2(a) S-2-Pyridyl 3-oxo-4-androstene-17β-thiocarboxylate 10.0 g of 3-oxo-4-androstene-17β-carboxylic acid, 14.0 g of 2,2'-pyridyl disulfide and 16.7 g of triphenylphosphine were dissolved in 100 ml of dry toluene, and the resulting solution was stirred at room temperature for 24 hours in a stream of nitrogen. At the end of this time, the reaction mixture was subjected, without further treatment, to silica gel column chromatography, using a 1:1 by volume mixture of hexane and ethyl acetate as the eluent, to give 12.0 g of the title compound as white crystals.

Nuclear Magnetic Resonance Spectrum (CDCl$_3$), δ ppm:

0.80 (3H, singlet);

0.95–2.12 (13H, multiplet);

1.19 (3H, singlet);

2.20–2.49 (6H, multiplet);

2.74 (1H, triplet, J=9.3 Hz);

5.74 (1H, singlet);

7.27–7.31 (1H, multiplet)

7.59–7.63 (1H, multiplet);

7.70–7.77 (1H, multiplet);

8.61–8.64 (1H, multiplet).

Infrared Absorption Spectrum (KBr), $v_{max}$ cm$^{-1}$: 2967, 2936, 1691, 1664, 1568, 1563, 1418.

2(b) N-[1-(4-Methoxyphenyl)-1-methylethyl]-3-oxo-4-androstene-17β-carboxamide 610 mg of S-2-pyridyl 3-oxo-4-androstene-17β-thiocarboxylate [prepared as described in step (a) above] were dissolved in 1 ml of dry methylene chloride, and 630 mg of 1-(4-methoxyphenyl)-1-methylethylamine (prepared as described in Preparation 10a) were added to the resulting solution. The mixture was then stirred at room temperature for 3 days. At the end of this time, the reaction mixture was subjected, without further treatment, to silica gel column chromatography using a gradient elution method, with mixtures of methylene chloride and acetone in ratios ranging from 3:2 to 1:1 by volume as the eluent, and the product was recrystallized from diisopropyl ether, to give 670 mg of the title compound as white crystals.

Nuclear Magnetic Resonance Spectrum (CDCl$_3$), δ ppm:

0.71 (3H, singlet);

0.91–1.90 (12H, multiplet);

1.19 (3H, singlet);

1.70 (3H, singlet);

1.71 (3H, singlet);

1.99–2.46 (8H, multiplet);

3.79 (3H, singlet);

5.47 (1H, singlet);

5.73 (1H, singlet);

6.86 (2H, doublet, J=8.8 Hz);

7.33 (2H, doublet, J=8.8 Hz).

Infrared Absorption Spectrum (KBr), $v_{max}$ cm$^{-1}$: 3353, 2966, 2941, 1661, 1614, 1513, 1454.

2(c) N-[1-(4-Methoxyphenyl)-1-methylethyl]-3-cyanoandrosta-3,5-diene-17β-carboxamide 660 mg of N-[1-(4-methoxyphenyl)-1-methylethyl]-3-oxo-4-androstene-17β-carboxamide [prepared as described in step (b) above] were dissolved in 5 ml of dry tetrahydrofuran, and 0.30 ml of diethyl cyanophosphate and 67 mg of lithium cyanide were added to the resulting solution. The mixture was then stirred at room temperature for 30 minutes. At the end of this time, the solvent was removed from the reaction mixture by distillation under reduced pressure, and the resulting residue was dissolved in a 1:1 by volume mixture of ethyl acetate and benzene. The resulting solution was then washed with water and with a saturated aqueous solution of sodium chloride, in that order; it was then dried over anhydrous sodium sulfate. The solvent was then removed by distillation under reduced pressure. The resulting residue was dissolved in 5 ml of dry toluene, and the solution thus obtained was stirred at room temperature for 4 hours, whilst a boron trifluoride—diethyl ether complex was added in an amount of 20 μl every 30 minutes. At the end of this time, a saturated aqueous solution of sodium hydrogencarbonate was added to the reaction mixture, and the resulting mixture was extracted with a 1:1 by volume mixture of ethyl acetate and benzene. The extract was washed with water and with a saturated aqueous solution of sodium chloride, in that order, and dried over anhydrous sodium sulfate. The solvent was then removed from the mixture by evaporation under reduced pressure. The residue was subjected to silica gel column chromatography using a gradient elution method, with mixtures of hexane and ethyl acetate in ratios ranging from 3:1 to 3:2 by volume as the eluent, and the product was crystallized from diisopropyl ether, to give 300 mg of the title compound as white crystals.

Nuclear Magnetic Resonance Spectrum (CDCl$_3$), δ ppm:

0.70 (3H, singlet);

0.93 (3H, singlet);

0.97–1.92 (10H, multiplet);

1.70 (3H, singlet);

1.71 (3H, singlet);

1.99–2.38 (8H, multiplet);

3.79 (3H, singlet);

5.49 (1H, singlet);

5.77 (1H, triplet, J=3.2 Hz);

6.65 (1H, singlet);

6.86 (2H, doublet, J=8.8 Hz);

7.34 (2H, doublet, J=8.8 Hz).

Infrared Absorption Spectrum (KBr), $v_{max}$ cm$^{-1}$: 3399, 2962, 2914, 2199, 1681, 1632, 1615, 1598, 1512, 1455.

2(d) 17β-{N-[1-(4-Methoxyphenyl)-1-methylethyl]carbamoyl}androsta-3,5-diene-3-carboxylic acid 280 mg of N-[1-(4-methoxyphenyl)-1-methylethyl]-3-cyanoandrosta-3,5-diene-17β-carboxanide [prepared as described in step (c) above] were suspended in 15 ml of ethylene glycol, and a solution of 2.2 g of potassium hydroxide in 5 ml of water was added to the resulting suspension. The mixture was then heated under reflux for 24 hours in a nitrogen stream. At the end of this time, the reaction mixture was cooled to room temperature and made acidic by the addition of 10% w/v aqueous hydrochloric acid, and then the mixture was extracted with methylene chloride. The extract was washed with water and with a saturated aqueous solution of sodium chloride, in that order, after which it was dried over anhydrous sodium sulfate. The solvent was then removed from the mixture by evaporation under reduced pressure. The residue was recrystallized from a mixture of acetone and diethyl ether, and the resulting crystals were collected by filtration. The mother liquor was purified by silica gel column chromatography using a gradient elution method, with mixtures of methylene chloride and acetone in ratios ranging from 9:1 to 7:3 by volume as the eluent, to give 268 mg of the title compound as white powdery crystals.

Nuclear Magnetic Resonance Spectrum (CDCl$_3$), δ ppm:
0.71 (3H, singlet);
0.93 (3H, singlet);
1.03–2.60 (18H, multiplet);
1.70 (3H, singlet);
1.72 (3H, singlet);
3.80 (3H, singlet);
5.51 (1H, singlet);
5.85 (1H, triplet, J=2.7 Hz);
6.86 (2H, doublet, J=8.8 Hz);
7.12 (1H, singlet);
7.34 (2H, doublet, J=8.8 Hz).

Infrared Absorption Spectrum (KBr), $v_{max}$ cm$^{-1}$: 3448, 2966, 2940, 1663, 1633, 1612, 1514, 1420.

EXAMPLE 3

17β-[N-(Diphenylamino)carbamoyl]androsta-3,5-diene-3-carboxylic acid (Compound No. 159)

3(a) S-2-Pyridyl 3-cyanoandrosta-3,5-diene-17β-thiocarboxylate 7.0 g of 3-cyanoandrosta-3,5-diene-17β-carboxylic acid [prepared as described in Example 1(b)], 10.2 g of triphenylphosphine and 8.8 g of 2,2'-dipyridyl disulfide were dissolved in 100 ml of dry benzene, and the resulting solution was stirred at room temperature overnight. At the end of this time, the reaction mixture was subjected, without further treatment, to column chromatography through 350 g of silica gel using a gradient elution method, with mixtures of acetone and methylene chloride in ratios ranging from 1:99 to 2:98 by volume as the eluent, to give 6.9 g of the title compound.

Nuclear Magnetic Resonance Spectrum (CDCl$_3$), δ ppm:
0.79 (3H, singlet);
0.94 (3H, singlet);
0.80–2.50 (17H, multiplet);
2.74 (1H, triplet, J=9 Hz);
5.77 (1H, triplet, J=2 Hz);
6.65 (1H, singlet);
7.25–7.31 (1H, multiplet);
7.60–7.64 (1H, multiplet);
7.71–7.78 (1H, multiplet);
8.61–8.64 (1H, multiplet).

Infrared Absorption Spectrum (KBr), $v_{max}$ cm$^{-1}$: 2957, 2946, 2911, 2200, 1708, 1631, 1573, 1454, 1420, 1152, 1039, 768.

3(b) N,N-Diphenyl-3-cyanoandrosta-3,5-diene-17β-carbohydrazide 505 mg of S-2-pyridyl 3-cyanoandrosta-3,5-diene-17β-thiocarboxylate [prepared as described in step (a) above] were dissolved in 7 ml of pyridine, and 330 mg of 1,1-diphenylhydrazine hydrochloride were added to the resulting solution. The mixture was then stirred at room temperature overnight. At the end of this time, the solvent was removed from the reaction mixture by distillation under reduced pressure, and the residue was subjected to silica gel column chromatography using a gradient elution method, with mixtures of methylene chloride and acetone in ratios ranging from 99:3 to 9:1 by volume as the eluent, and the product was crystallized from diisopropyl ether, to give 500 mg of the title compound as white crystals.

Nuclear Magnetic Resonance Spectrum (CDCl$_3$), δ ppm:
0.74 (3H, singlet);
0.94 (3H, singlet);
1.03–1.95 (12H, multiplet);
2.04–2.38 (6H, multiplet);
5.77 (1H, triplet, J=2.9 Hz);
6.65 (1H, singlet);
6.98–7.33 (10H, multiplet);
7.43 (1H, singlet).

Infrared Absorption Spectrum (KBr), $v_{max}$ cm$^{-1}$: 3230, 2943, 2909, 2208, 1667, 1634, 1591, 1496.

3(c) 17β-[N-(Diphenylamino)carbamoyl]androsta-3,5-diene-3-carboxylic acid

A procedure similar to that described in Example 1(d) was repeated, except that N,N-diphenyl-3-cyanoandrosta-3,5-diene-17β-carbohydrazide [prepared as described in step (b) above] was employed as a starting material, in a relative amount similar to that used in that Example, to give the title compound in a yield of 80%.

Nuclear Magnetic Resonance Spectrum (CDCl$_3$), δ ppm:
0.74 (3H, singlet);
0.93 (3H, singlet);
1.02–2.58 (33H, multiplet);
5.86 (1H, triplet, J=2.7 Hz);
6.98–7.36 (11H, multiplet);
7.44 (1H, singlet).

Infrared Absorption Spectrum (KBr), $v_{max}$ cm$^{-1}$: 3265, 2940, 1677, 1633, 1591, 1495.

EXAMPLE 4

17β-[N-(1-Methyl-1-phenylethyl)carbamoyl] androsta-3,5-diene-3-carboxylic acid (Compound No. 66)

4(a) N-(1-Methyl-1-phenylethyl)-3-cyanoandrosta-3,5-diene-17β-carboxamide

A procedure similar to that described in Example 3(b) was repeated, except that S-2-pyridyl 3-cyanoandrosta-3,5-diene-17β-thiocarboxylate [prepared as described in Example 3(a)] and 1-methyl-1-phenylethylamine were used as starting materials, in relative proportions similar to those used in that Example, to give the title compound in a yield of 75%.

Nuclear Magnetic Resonance Spectrum (CDCl$_3$), δ ppm:
0.71 (3H, singlet);
0.94 (3H, singlet);
0.98–1.92 (12H, multiplet);
1.71 (3H, singlet);
1.73 (3H, singlet);
2.02–2.40 (6H, multiplet);
5.53 (1H, singlet);
5.77 (1H, triplet, J=3.4 Hz);
6.65 (1H, singlet);
7.19–7.44 (5H, multiplet).

Infrared Absorption Spectrum (KBr), $v_{max}$ cm$^{-1}$: 3445, 2964, 2896, 2861, 2202, 1685, 1640, 1603, 1495.

4(b) 17β-[N-(1-Methyl-1-phenylethyl)carbamoyl]androsta-3,5-diene-3-carboxylic acid A procedure similar to that described in Example 1(d) was repeated, except that N-(1-methyl-1-phenylethyl)-3-cyanoandrosta-3,5-diene-17β-carboxamide [prepared as described in step (a) above] was employed as a starting material, in a relative amount similar to that used in that Example, to give the title compound in a yield of 82%.

Nuclear Magnetic Resonance Spectrum (CDCl$_3$), δ ppm:

0.72 (3H, singlet);

0.93 (3H, singlet);

1.01–2.57 (18H, multiplet);

1.71 (3H, singlet);

1.74 (3H, singlet);

5.54 (1H, singlet);

5.87 (1H, broad singlet);

7.14 (1H, singlet);

7.20–7.44 (5H, multiplet).

Infrared Absorption Spectrum (KBr), $v_{max}$ cm$^{-1}$: 3440, 2940, 1680, 1667, 1632, 1608, 1495.

EXAMPLE 5

17β{N-[1-Methyl-1-(3-thienyl)ethyl]carbamoyl}androsta-3,5-diene-3-carboxylic acid (Compound No. 191)

Procedures similar to those described in Examples 4(a) and 4(b) were repeated, except that S-2-pyridyl 3-cyanoandrosta-3,5-diene-17β-thiocarboxylate [prepared as described in Example 3(a)] and 1-methyl-1-(3-thienyl)ethylamine (prepared as described in Preparation 11b) were employed as starting materials, in relative proportions similar to those used in that Example, to give the title compound in a yield of 55%.

Nuclear Magnetic Resonance Spectrum (CDCl$_3$), δ ppm:

0.71 (3H, singlet);

0.93 (3H, singlet);

1.70 (3H, singlet);

1.73 (3H, singlet);

5.53 (1H, singlet);

5.85 (1H, broad singlet);

6.9–7.0 (2H, multiplet)

7.14 (1H, singlet);

7.28 (1H, multiplet).

EXAMPLE 6

17β-[N-(1,2-Diphenylethyl)carbamoyl]androsta-3,5-diene-3-carboxylic acid (Compound No. 1)

6(a) N-(1,2-Diphenylethyl)-3-cyanoandrosta-3,5-diene-17β-carboxamide

A procedure similar to that described in Example 3(b) was repeated, except that S-2-pyridyl 3-cyanoandrosta-3,5-diene-17β-thiocarboxylate [prepared as described in Example 3(a)] and 1,2-diphenylethylamine were employed as starting materials, in relative proportions similar to those used In that Example, to give the title compound in a quantitative yield.

Infrared Absorption Spectrum (KBr), $v_{max}$ cm$^{-1}$: 3416, 2965, 2948, 2913, 2204, 1658, 1636, 1603, 1495, 1454, 1234, 699.

6(b) 17β-[N-(1,2-Diphenylethyl)carbamoyl]androsta-3,5-diene-3-carboxylic acid

Following a procedure similar to that described in Example 1(d), but using 630 mg of N-(1,2-diphenylethyl)-3-cyanoandrosta-3,5-diene-17β-carboxamide [prepared as described in step (a) above], the title compound was obtained in a yield of 41%.

Nuclear Magnetic Resonance Spectrum (CDCl$_3$), δ ppm:

0.50 & 0.54 (together 3H, each singlet);

0.88 & 0.90 (together 3H, each singlet);

0.93–2.55 (18H, multiplet);

2.99–3.21 (2H, multiplet);

5.24–5.39 (1H, multiplet);

5.50 & 5.60 (together 1H, each doublet, J=7.0 Hz);

5.84 (1H, singlet);

7.04–7.35 (11H, multiplet).

Infrared Absorption Spectrum (Kr), $v_{max}$ cm$^{-1}$: 3029, 2940, 1671, 1633, 1610, 1496, 1278, 1188, 698.

EXAMPLE 7

17β-{N-[1-(3,4-Dimethoxyphenyl)-1-methylethyl]carbamoyl}androsta-3,5-diene-3-carboxylic acid (Compound No. 192)

7(a) N-[1-(3,4-Dimethoxyphenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(3,4-dimethoxyphenyl)-1-methylethylamine (prepared as described in Preparation 10e) as starting materials, in relative proportions similar to those used in that Example, the title compound was obtained in a yield of 60%.

Infrared Absorption Spectrum (KBr), $v_{max}$ cm$^{-1}$: 3374, 2965, 2938, 2203, 1676, 1634, 1604, 1518, 1453, 1261, 1145, 1029.

7(b) 17β-{N-[1-(3,4-Dimethoxyphenyl)-1-methylethyl]carbamoyl}androsta-3,5-diene-3-carboxylic acid Following a procedure similar to that described in Example 1(d), but using N-[1-(3,4-dimethoxyphenyl)-1-methylethyl]-3-cyanoandrosta-3,5-diene-17β-carboxamide [prepared as described in step (a) above] as a starting material, in a relative amount similar to that used in that Example, the title compound was obtained in a yield of 58%.

Nuclear Magnetic Resonance Spectrum (CDCl$_3$), δ ppm:

0.72 (3H, singlet);

0.92 (3H, singlet);

1.03–2.57 (18H, multiplet);

1.71 (3H, singlet);

1.72 (3H, singlet);

3.86 (3H, singlet);

3.88 (3H, singlet);

5.51 (1H, singlet);

5.86 (1H, singlet);

6.81–6.84 (1H, multiplet);

6.95–6.99 (2H, multiplet);

7.14 (1H, singlet).

Infrared Absorption Spectrum (KBr), $v_{max}$ cm$^{-1}$: 3437, 2967, 2939, 1674, 1633, 1610, 1518, 1453, 1262, 1145, 1028, 803, 766, 641.

EXAMPLE 8

17β-{N-[1-(2-Methoxyphenyl)-1-methylethyl]carbamoyl}androsta-3,5-diene-3-carboxylic acid (Compound No. 168)

8(a) N-[1-(2-Methoxyphenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(2-methoxyphenyl)-1-methylethylamine (prepared as described in Preparation 10c) as starting materials, in relative proportions similar to those used in that Example, the title compound was obtained in a yield of 96%.

Infrared Absorption Spectrum (KBr), $v_{max}$ cm$^{-1}$: 3386, 2939, 2203, 1675, 1633, 1602, 1490, 1451, 1380, 1241, 1029, 752

8(b) 17β-{N-[1-Methoxyphenyl)-1-methylethyl]carbamoyl}androsta-3,5-diene-3-carboxylic acid Following a procedure similar to that described in Example 1(d), but using N-[1-(2-methoxyphenyl)-1-methylethyl]-3-cyanoandrosta-3,5-diene-17β-carboxamide [prepared as described in step (a) above] as a starting material, in a relative amount similar to that used in that Example, the title compound was obtained in a yield of 50%.

Nuclear Magnetic Resonance Spectrum (CDCl$_3$), δ ppm:
0.67 (3H, singlet);
0.91 (3H, singlet);
1.00–2.56 (18H, multiplet);
1.77 (3H, singlet);
1.81 (3H, singlet);
3.83 (3H, singlet);
5.86 (1H, singlet);
5.97 (1H, singlet);
6.87–6.97 (2H, multiplet);
7.14 (1H, singlet);
7.19–7.26 (1H, multiplet);
7.38–7.42 (1H, multiplet).

Infrared Absorption Spectrum (KBr), $v_{max}$ cm$^{-1}$: 3450, 2972, 2939, 1670, 1634, 1607, 1490, 1452, 1288, 1241, 1189, 1019, 754, 641.

EXAMPLE 9

17β-{N-[1-(3-Methoxyphenyl)-1-methylethyl]carbamoyl}androsta-3,5-diene-3-carboxylic acid
(Compound No. 166)

9(a) N-[1-(3-Methoxyphenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(3-methoxyphenyl)-1-methylethylamine (prepared as described in Preparation 10b) as starting materials, in relative proportions similar to those used in that Example, the title compound was obtained in a yield of 64%.

Infrared Absorption Spectrum (KBr), $v_{max}$ cm$^{-1}$: 3347, 2966, 2940, 2203, 1675, 1633, 1603, 1584, 1486, 1448, 1266, 1049, 700.

9(b) 17β-{N-[1-(3-Methoxyphenyl)-1-methylethyl]carbamoyl}androsta-3,5-diene-3-carboxylic acid Following a procedure similar to that described in Example 1(d), but using N-[1-(3-methoxyphenyl)-1-methylethyl]-3-cyanoandrosta-3,5-diene-17β-carboxamide [prepared as described in step (a) above] as a starting material, in a relative amount similar to that used in that Example, the title compound was obtained in a yield of 33%.

Nuclear Magnetic Resonance Spectrum (CDCl$_3$), δ ppm:
0.73 (3H, singlet)
0.93 (3H, singlet);
1.04–2.57 (18H, multiplet);
1.70 (3H, singlet);
1.72 (3H, singlet);
3.80 (3H, singlet);
5.54 (1H, singlet);
5.85 (1H, singlet);
6.75–6.79 (1H, multiplet);
6.95–7.02 (2H, multiplet);
7.14 (1H, singlet);
7.23–7.29 (1H, multiplet).

Infrared Absorption Spectrum (KBr), $v_{max}$ cm$^{-1}$: 3438, 2966, 2939, 1666, 1632, 1608, 1583, 1498, 1454, 1428, 1275, 1233, 1188, 1049, 780, 701.

EXAMPLE 10

17β-{N-[1-(3,5-Dimethoxyphenyl)-1-methylethyl]carbamoyl}androsta-3,5-diene-3-carboxylic acid
(Compound No. 149)

10(a) N-[1-(3,5-Dimethoxyphenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(3,5-dimethoxyphenyl)-1-methylethylamine amine (prepared as described in Preparation 10d) as starting materials, in relative proportions similar to those used in that Example, the title compound was obtained in a yield of 83%.

Infrared Absorption Spectrum (KBr), $v_{max}$ cm$^{-1}$: 3358, 2965, 2940, 2202, 1679, 1633, 1598, 1504, 1453, 1421, 1204, 1153, 1052, 696.

10(b) 17β-{N-[1-(3,5-Dimethoxyphenyl)-1-methylethyl]carbamoyl}androsta-3,5-diene-3-carboxylic acid Following a procedure similar to that described in Example 1(d), but using N-[1-(3,5-dimethoxyphenyl)-1-methylethyl]-3-cyanoandrosta-3,5-diene-17β-carboxamide [prepared as described in step (a) above] as a starting material, in a relative amount similar to that used in that Example, the title compound was obtained in a yield of 51%.

Nuclear Magnetic Resonance Spectrum (CDCl$_3$), δ ppm:
0.74 (3H, singlet);
0.93 (3H, singlet);
1.04–2.63 (18H, multiplet);
1.68 (3H, singlet);
1.71 (3H, singlet);
3.79 (6H, singlet);
5.53 (1H, singlet);
5.85 (1H, singlet);
6.34 (1H, triplet, J=2.0 Hz);
6.56 (2H, doublet, J=2.0 Hz);
7.13 (1H, singlet).

Infrared Absorption Spectrum (KBr), $v_{max}$ cm$^{-1}$: 3344, 2965, 2939, 1676, 1634, 1598, 1503, 1456, 1423, 1292, 1204, 1154, 1066, 834, 696, 640.

EXAMPLE 11

17β-{N-[1-(4-Methylphenyl)-1-methylethyl]carbamoyl}androsta-3,5-diene-3-carboxylic acid
(Compound No. 196)

11(a) N-[1-(4-Methylphenyl)-1-methylethyl]-3-cyanoandrosta-3,5-diene-17β-carboxamide Following a procedure similar to that described in Example 3(b), but using S-2-pyridyl 3-cyanoandrosta-3,5- diene-17β-thiocarboxylate [prepared as described in Example 3(a)] and 1-(4-methylphenyl)-1-methylethylamine (prepared as described in Preparation 10h) as starting materials, in relative proportions similar to those used in that Example, the title compound was obtained in a yield of 88%.

Infrared Absorption Spectrum (KBr), $v_{max}$ cm$^{-1}$: 3446, 2963, 2896, 2203, 1685, 1637, 1604, 1495, 1382, 1257, 810, 541.

11(b) 17β-{N-[1-(4-Methylphenyl)-1-methylethyl]carbamoyl}androsta-3,5-diene-3-carboxylic acid Following a procedure similar to that described in Example 1(d), but using N-[1-(4-methylphenyl)-1-methylethyl]-3-cyanoandrosta-3,5-diene-17β-carboxamide [prepared as described in step (a) above] as a starting material, in a relative amount similar to that used in that Example, the title compound was obtained in a yield of 47%.

Nuclear Magnetic Resonance Spectrum (CDCl$_3$), δ ppm:

0.72 (3H, singlet);

0.92 (3H, singlet);

0.99–2.56 (18H, multiplet);

1.70 (3H, singlet);

1.72 (3H, singlet);

2.32 (3H, singlet);

5.52 (1H, singlet);

5.86 (1H, singlet);

7.14 (2H, doublet, J=7.8 Hz);

7.15 (1H, singlet);

7.28 (2H, doublet, J=7.8 Hz).

Infrared Absorption Spectrum (KBr), $v_{max}$ cm$^{-1}$: 3437, 2968, 2940, 1666, 1633, 1610, 1494, 1452, 1420, 1277, 1188, 815, 640, 552.

EXAMPLE 12

17β-[N-(1-Ethyl-1-phenylpropyl)carbamoyl]androsta-3,5-diene-3-carboxylic acid (Compound No. 195)

12(a) N-(1-Ethyl-1-phenylpropyl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 1-ethyl-1-phenylpropylamine as starting materials, in relative proportions similar to those used in that Example, the title compound was obtained in a yield of 79%.

Infrared Absorption Spectrum (KBr), $v_{max}$ cm$^{-1}$: 3358, 2965, 2937, 2203, 1678, 1634, 1603, 1510, 1495, 1446, 1380, 1235, 757, 698.

12(b) 17β-[N-(1-Ethyl-1-phenylpropyl)carbamoyl]androsta-3,5-diene-3-carboxylic acid Following a procedure similar to that described in Example 1(d), but using N-(1-ethyl-1-phenylpropyl)-3-cyanoandrosta-3,5-diene-17β-carboxamide [prepared as described in step (a) above] as a starting material, in a relative amount similar to that used in that Example, the title compound was obtained in a yield of 37%.

Nuclear Magnetic Resonance Spectrum (CDCl$_3$), δ ppm:

0.72 (6H, triplet, J=7.6 Hz);

0.77 (3H, singlet);

0.93 (3H, singlet);

1.03–2.57 (22H, multiplet);

5.42 (1H, singlet);

5.88 (1H, singlet);

7.14 (1H, singlet);

7.19–7.37 (5H, multiplet).

Infrared Absorption Spectrum (KBr), $v_{max}$ cm$^{-1}$: 3441, 2968, 2939, 1675, 1633, 1608, 1495, 1446, 1421, 1378, 1279, 1188, 757, 698, 640.

EXAMPLE 13

17β-{N-[1-(4-Ethoxyphenyl)-1-methylethyl]carbamoyl}androsta-3,5-diene-3-carboxylic acid (Compound No. 194)

13(a) N-[1-(4-Ethoxyphenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(4-ethoxyphenyl)-1-methylethylamine (prepared as described in Preparation 10g) as starting materials, in relative proportions similar to those used in that Example, the title compound was obtained in a yield of 91%.

Infrared Absorption Spectrum (KBr), $v_{max}$ cm$^{-1}$: 3361, 2969, 2940, 2203, 1678, 1633, 1609, 1512, 1453, 1243, 1181, 1048, 833.

13(b) 17β-{N-[1-(4-Ethoxyphenyl)-1-methylethyl]carbamoyl}androsta-3,5-diene-3-carboxylic acid Following a procedure similar to that described in Example 1(d), but using N-[1-(4-ethoxyphenyl)-1-methylethyl]-3-cyanoandrosta-3,5-diene-17β-carboxamide [prepared as described in step (a) above] as a starting material, in a relative amount similar to that used in that Example, the title compound was obtained in a yield of 50%.

Nuclear Magnetic Resonance Spectrum (CDCl$_3$), δ ppm:

0.71 (3H, singlet);

0.92 (3H, singlet);

1.05–2.50 (18H, multiplet);

1.40 (3H, triplet, J=6.8 Hz);

1.70 (3H, singlet);

1.72 (3H, singlet);

4.00 (2H, quartet, J=6.8 Hz);

5.49 (1H, singlet);

5.86 (1H, singlet);

6.84 (2H, doublet, J=7.0 Hz);

7.14 (1H, singlet);

7.32 (2H, doublet, J=7.0 Hz).

Infrared Absorption Spectrum (KBr), $v_{max}$ cm$^{-1}$: 2968, 2938, 1682, 1631, 1609, 1512, 1280, 1244, 1183, 1047, 926, 824, 639.

EXAMPLE 14

17β-{N-[1-Methyl-1-(2-thienyl)ethyl]carbamoyl}androsta-3,5-diene-3-carboxylic acid (Compound No. 67)

14(a) N-[1-Methyl-1-(2-thienyl)ethyl]-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 1-methyl-1-(2-thienyl)ethylamine (prepared as described in Preparation 11a) as starting materials, in relative proportions similar to those used in that Example, the title compound was obtained in a yield of 88%.

Infrared Absorption Spectrum (KBr), $v_{max}$ cm$^{-1}$: 3350, 2966, 2941, 2203, 1679, 1634, 1603, 1500, 1452, 1382, 1246, 695.

14(b) 17β-{N-[1-Methyl-1-(2-thienyl)ethyl]carbamoyl}androsta-3,5-diene-3-carboxylic acid Following a procedure similar to that described in Example 1(d), but using N-[1-methyl-1-(2-thienyl)ethyl]-3-cyanoandrosta-3,5-diene-17β-carboxamide [prepared as described in step (a) above] as a starting material, in a relative amount similar to that used in that Example, the title compound was obtained in a yield of 57%.

Nuclear Magnetic Resonance Spectrum (CDCl$_3$), δ ppm:

0.72 (3H, singlet);

0.92 (3H, singlet);

0.95–2.57 (18H, multiplet);

1.82 (3H, singlet);

1.83 (3H, singlet);

5.54 (1H, singlet);

5.85 (1H, singlet);

6.95 (1H, doublet of doublets, J=5.0 & 3.0 Hz);

7.10 (1H, doublet of doublets, J=3.0 & 1.0 Hz);

7.15 (1H, singlet);

7.19 (1H, doublet of doublets, J=5.0 & 1.0 Hz).

Infrared Absorption Spectrum (KBr), ν$_{max}$ cm$^{-1}$: 3400, 2967, 2940, 1673, 1633, 1609, 1490, 1419, 1279, 1188, 704.

EXAMPLE 15

17β[N-(4-Hydroxybenzhydryl)carbamoyl]androsta-3,5-diene-3-carboxylic acid (Compound No. 127)

15(a) N-(4-Hydroxybenzhydryl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 4-hydroxybenzhydrylamine (prepared as described in Preparation 13) as starting materials, in relative proportions similar to those used in that Example, the title compound was obtained in a yield of 83%.

Infrared Absorption Spectrum (KBr), ν$_{max}$ cm$^{-1}$: 3327, 2966, 2942, 2910, 2204, 1640, 1614, 1601, 1514, 1495, 1232, 1171, 699.

15(b) 17β-[N-(4-Hydroxybenzhydryl)carbamoyl]androsta-3,5-diene-3-carboxylic acid Following a procedure similar to that described in Example 1(d), but using N-(4-hydroxybenzhydryl)-3-cyanoandrosta-3,5-diene-17β-carboxamide [prepared as described in step (a) above] as a starting material, in a relative amount similar to that used in that Example, the title compound was obtained in a yield of 34%.

Nuclear Magnetic Resonance Spectrum (CDCl$_3$), δ ppm:

0.71 (3H, singlet);

0.91 (3H, singlet);

1.06–2.64 (19H, multiplet);

5.87 (1H, singlet);

5.87 & 5.97 (together 1H, each doublet, J=7.0 Hz);

6.72–6.76 (2H, multiplet);

7.03–7.37 (8H, multiplet).

Infrared Absorption Spectrum (KBr), ν$_{max}$ cm$^{-1}$: 3310, 2966, 2940, 1675, 1636, 1614, 1514, 1495, 1271, 1232, 1186, 1172, 699.

EXAMPLE 16

17β-[N-(4,4'-Difluorobenzhydryl)carbamoyl]androsta-3,5-diene-3-carboxylic acid (Compound No. 12)

16(a) N-(4,4'-Difluorobenzhydryl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 4,4'-di-fluorobenzhydrylamine (prepared as described in Preparation 12) as starting materials, in relative proportions similar to those used in that Example, the title compound was obtained in a yield of 91%.

Infrared Absorption Spectrum (KBr), ν$_{max}$ cm$^{-1}$: 3346, 2967, 2948, 2912, 2205, 1661, 1636, 1604, 1508, 148, 1229, 1158, 833, 552.

16(b) 17β-[N-(4,4'-Difluorobenzhydryl)carbamoyl]androsta-3,5-diene-3-carboxylic acid Following a procedure similar to that described in Example 1(d), but using N-(4,4'-difluorobenzhydryl)-3-cyanoandrosta-3,5-diene-17β-carboxamide [prepared as described in step (a) above] as a starting material, in a relative amount similar to that used in that Example, the title compound was obtained in a yield of 34%.

Nuclear Magnetic Resonance Spectrum (CDCl$_3$), δ ppm:

0.70 (3H, singlet);

0.92 (3H, singlet);

0.96–2.56 (18H, multiplet);

5.78 (1H, doublet, J=7.8 Hz);

5.86 (1H, singlet);

6.25 (1H, doublet, J=7.8 Hz);

7.08 (4H, multiplet);

7.13–7.23 (5H, multiplet).

Infrared Absorption Spectrum (KBr), ν$_{max}$ cm$^{-1}$: 2942, 2910, 1669, 1634, 1607, 1508, 1419, 1279, 1228, 1189, 1158, 833, 552.

EXAMPLE 17

17β-[N-(4,4'-Dimethoxybenzhydryl)carbamoyl]androsta-3,5-diene-3-carboxylic acid (Compound No. 14)

17(a) N-(4, 4'-Dimethoxybenzhydryl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 4,4'-dimethoxybenzhydrylamine (prepared as described in Preparation 14) as starling materials, in relative proportions similar to those used in that Example, the title compound was obtained in a yield of 79%.

Infrared Absorption Spectrum (KBr), ν$_{max}$ cm$^{-1}$: 3425, 2945, 2908, 2205, 1657, 1637, 1607, 1511, 1488, 1248, 1176, 1036, 835, 567.

17(b) 17β-[N-(4,4'-Dimethoxybenzhydryl)carbamoyl]androsta-3,5-diene-3-carboxylic acid Following a procedure similar to that described in Example 1(d), but using N-(4,4'-dimethoxybenzhydryl)-3-cyanoandrosta-3,5-diene-17β-carboxamide [prepared as described in step (a) above] as a starting material, in a relative amount similar to that used in that Example, the title compound was obtained in a yield of 52%.

Nuclear Magnetic Resonance Spectrum (CDCl$_3$), δ ppm:

0.71 (3H, singlet);

0.91 (3H, singlet);

1.02-2.49 (18H, multiplet);
3.79 (6H, singlet);
5.81 (1H, doublet, J=7.8 Hz);
5.86 (1H, singlet);
6.19 (1H, doublet, J=7.8 Hz);
6.82-6.89 (4H, multiplet);
7.12-7.17 (5H, multiplet).

Infrared Absorption Spectrum (KBr), $v_{max}$ cm$^{-1}$: 2940, 2910, 1666, 1635, 1610, 1511, 1248, 1175, 1035, 829, 640, 565.

EXAMPLE 18

17β-{N-[1-(4-N,N-Dimethylaminophenyl)-1-methylethyl]carbamoyl}androsta-3,5-diene-3-carboxylic acid (Compound No. 190)

18(a) N-[1-(4-N,N-Dimethylaminophenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(4-N,N-dimethylaminophenyl)-1-methylethylamine (prepared as described in Preparation 10i) as starting materials, in relative proportions similar to those used in that Example, the title compound was obtained in a yield of 83%.

Infrared Absorption Spectrum (KBr), $v_{max}$ cm$^{-1}$: 3351, 2965, 2939, 2202, 1677, 1632, 1614, 1522, 1493, 1446, 1359, 1200, 815.

18(b) 17β-{N-[1-(4-N,N-Dimethylaminophenyl)-1-methylethyl]carbamoyl}androsta-3,5-diene-3-carboxylic acid Following a procedure similar to that described in Example 1(d), but using N-[1-(4-N,N-dimethylaminophenyl)-1-methylethyl]-3-cyanoandrosta-3,5-diene-17β-carboxamide [prepared as described in step (a) above] as a starting material, in a relative amount similar to that used in that Example, the title compound was obtained in a yield of 35%.

Nuclear Magnetic Resonance Spectrum (CDCl$_3$), δ ppm:
0.73 (3H, singlet);
0.93 (3H, singlet);
0.99-2.57 (18H, multiplet);
1.71 (3H, singlet);
1.73 (3H, singlet);
2.95 (6H, singlet);
5.48 (1H, singlet);
5.86 (1H, singlet);
6.65-6.85 (2H, broad singlet);
7.14 (1H, singlet);
7.25-7.37 (2H, multiplet).

Infrared Absorption Spectrum (KBr), $v_{max}$ cm$^{-1}$: 2967, 2939, 2915, 1680, 1664, 1631, 1613, 1522, 1498, 1420, 1359, 1276, 949, 817, 640.

EXAMPLE 19

17β-{N-[1-(4-Fluorophenyl)-1-methylethyl]carbamoyl}androsta-3,5-diene-3-carboxylic acid (Compound No. 78)

19(a) N-[1-(4-Fluorophenyl)-1-methylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and 1-(4-fluorophenyl)-1-methylethylamine (prepared as described in Preparation 10f) as starting materials, in relative proportions similar to those used in that Example, the title compound was obtained in a yield of 82%.

Infrared Absorption Spectrum (KBr), $v_{max}$ cm$^{-1}$: 3439, 2966, 2946, 2204, 1673, 1634, 1601, 1512, 1494, 1232, 1164, 836.

19(b) 17β-{N-[1-(4-Fluorophenyl)-1-methylethyl]carbamoyl}androsta-3,5-diene-3-carboxylic acid Following a procedure similar to that described in Example 1(d), but using N-[1-(4-fluorophenyl)-1-methylethyl]-3-cyanoandrosta-3,5-diene-17β-carboxamide [prepared as described in step (a) above] as a starting material, in a relative amount similar to that used in that Example, the title compound was obtained in a yield of 55%.

Nuclear Magnetic Resonance Spectrum (CDCl$_3$), δ ppm:
0.69 (3H, singlet);
0.93 (3H, singlet);
1.00-2.57 (18H, multiplet);
1.68 (3H, singlet);
1.70 (3H, singlet);
5.53 (1H, singlet);
5.86 (1H, singlet);
7.00 (2H, triplet, J=8.8 Hz);
7.13 (1H, singlet);
7.37 (2H, doublet of doublets, J=8.8 & 5.4 Hz).

Infrared Absorption Spectrum (KBr), $v_{max}$ cm$^{-1}$: 3440, 2966, 2939, 1675, 1633, 1609, 1510, 1420, 1276, 1231, 832, 551.

EXAMPLE 20

17β-[N-(4-Chlorobenzhydryl)carbamoyl]androsta-3,5-diene-3-carboxylic acid (Compound No. 27)

20(a) N-(4-Chlorobenzhydryl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 4-chlorobenzhydrylamine as starting materials, in relative proportions similar to those used in that Example, the title compound was obtained in a yield of 70%.

Infrared Absorption Spectrum (KBr), $v_{max}$ cm$^{-1}$: 3349, 2965, 2945, 2205, 1661, 1637, 1603, 1490, 1453, 1090, 1014, 754.

20(b) 17β-[N-(4-Chlorobenzhydryl)carbamoyl]androsta-3,5-diene-3-carboxylic acid

Following a procedure similar to that described in Example 1(d), but using N-(4-chlorobenzhydryl)-3-cyanoandrosta-3,5-diene-17β-carboxamide [prepared as described in step (a) above] as a starting material, in a relative amount similar to that used in that Example, the title compound was obtained in a yield of 38%.

Nuclear Magnetic Resonance Spectrum (CDCl$_3$), δ ppm:
0.70 (3H, singlet);
0.91 & 0.92 (together 3H, each singlet);
1.00-2.56 (18H, multiplet);
5.82-5.87 (2H, multiplet);
6.25 & 6.26 (together 1H, each doublet, J=7.8 Hz);
7.13-7.38 (10H, multiplet).

Infrared Absorption Spectrum (KBr), $v_{max}$ cm$^{-1}$: 2941, 2910, 1674, 1635, 1613, 1490, 1279, 1209, 1188, 1090, 1014, 700.

EXAMPLE 21

17β-[N-(4-Methoxybenzhydryl)carbamoyl]androsta-3,5-diene-3-carboxylic acid (Compound No. 28)

21(a) N-(4-Methoxybenzhydryl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 4-methoxybenzhydrylamine (prepared as described in Preparation 15) as starting materials, in relative proportions similar to those used in that Example, the title compound was obtained in a yield of 82%.

Infrared Absorption Spectrum (KBr), $v_{max}$ cm$^{-1}$: 3344, 2964, 2945, 2910, 2205, 1661, 1636, 1607, 1511, 1493, 1249, 1177, 1033, 700.

21(b) 17β-[N-(4-Methoxybenzhydryl)carbamoyl]androsta-3,5-diene-3-carboxylic acid Following a procedure similar to that described in Example 1(d), but using N-(4-methoxybenzhydryl)-3-cyanoandrosta-3,5-diene-17β-carboxamide [prepared as described in step (a) above] as a starting material, in a relative amount similar to that used in that Example, the title compound was obtained in a yield of 37%.

Nuclear Magnetic Resonance Spectrum (CDCl$_3$), δ ppm:
0.71 (3H, singlet);
0.91 (3H, singlet);
1.00–2.56 (18H, multiplet);
3.79 & 3.80 (together 3H, each singlet);
5.85 (1H, doublet, J 7.8 Hz);
5.86 (1H, singlet);
6.24 (1H, doublet, J 7.8 Hz);
6.84–6.90 (2H, multiplet);
7.10–7.37 (8H, multiplet).

Infrared Absorption Spectrum (KBr), $v_{max}$ cm$^{-1}$: 2939, 2910, 1672, 1635, 1612, 1511, 1495, 1454, 1248, 1177, 1033, 699, 640.

EXAMPLE 22

17β-[N-(1,1-Dimethyl-2-phenylethyl)carbamoyl]androsta-3,5-diene-3-carboxylic acid (Compound No. 76)

22(a) N-(1,1-Dimethyl-2-phenylethyl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and 1,1-dimethyl-2-phenylethylamine as starting materials, in relative proportions similar to those used in that Example, the title compound was obtained in a yield of 82%.

Infrared Absorption Spectrum (KBr), $v_{max}$ cm$^{-1}$: 3436, 2965, 2938, 2916, 2205, 1678, 1633, 1604, 1501, 1451, 1385, 1233, 922, 729, 705.

22(b) 17β-[N-(1,1-Dimethyl-2-phenylethyl)carbamoyl]androsta-3,5-diene-3-carboxylic acid Following a procedure similar to that described in Example 1(d), but using N-(1,1-dimethyl-2-phenylethyl)-3-cyanoandrosta-3,5-diene-17β-carboxamide [prepared as described in step (a) above] as a starting material, in a relative amount similar to that used in that Example, the title compound was obtained in a yield of 45%.

Nuclear Magnetic Resonance Spectrum (CDCl$_3$), δ ppm:
0.73 (3H, singlet);
0.91 (3H, singlet);
0.96–2.56 (18H, multiplet);
1.27 (3H, singlet);
1.44 (3H, singlet);
2.82 (1H, doublet, J=13.2 Hz);
3.21 (1H, doublet, J=13.2 Hz);
4.99 (1H, singlet);
5.85 (1H, singlet);
7.14 (1H, singlet);
7.16–7.32 (5H, multiplet).

Infrared Absorption Spectrum (KBr), $v_{max}$ cm$^{-1}$: 2963, 2939, 2913, 1681, 1661, 1633, 1610, 1502, 1419, 1276, 1189, 924, 701.

EXAMPLE 23

17β-[N-(α,α-Dimethylfurfuryl)carbamoyl]androsta-3,5-diene-3-carboxylic acid (Compound No. 178)

23(a) N-(α,α-Dimethylfurfuryl)-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and α,α-dimethylfurfurylamine (prepared as described in Preparation 11c) as starting materials, in relative proportions similar to those used in that Example, the title compound was obtained in a yield of 71%.

Infrared Absorption Spectrum (KBr), $v_{max}$ cm$^{-1}$: 2968, 2945, 2911, 2201, 1707, 1631, 1603, 1573, 1449, 1420, 1038, 767.

23(b) 17β-[N-(α,α-Dimethylfurfuryl)carbamoyl]androsta-3,5-diene-3-carboxylic acid Following a procedure similar to that described in Example 1(d), but using N-(α,α-dimethylfurfuryl)-3-cyanoandrosta-3,5-diene-17β-carboxamide [prepared as described in step (a) above] as a starting material, in a relative amount similar to that used in that Example, the title compound was obtained in a yield of 27%.

Nuclear Magnetic Resonance Spectrum (CDCl$_3$), δ ppm:
0.67 (3H, singlet);
0.92 (3H, singlet);
0.99–2.57 (18H, multiplet);
1.70 (3H, singlet);
1.72 (3H, singlet);
5.52 (1H, singlet);
5.86 (1H, singlet);
6.19–6.21 (1H, multiplet);
6.30–6.32 (1H, multiplet);
7.14 (1H, singlet);
7.31–7.33 (1H, multiplet).

Infrared Absorption Spectrum (KBr), $v_{max}$ cm$^{-1}$: 2969, 2940, 1678, 1633, 1609, 1494, 1419, 1271, 1189, 735.

EXAMPLE 24

17β-{N-[(1S)-2-(4-Methylphenyl)-1-phenylethyl]carbamoyl}androsta-3,5-diene-3-carboxylic acid (Compound No. 22)

24(a) N-[(1S)-2-(4-Methylphenyl)-1-phenylethyl]-3-cyanoandrosta-3,5-diene-17β-carboxamide Following a procedure similar to that described in Example 3(b), but using S-2-pyridyl 3-cyanoandrosta-3,5-diene-17β-thiocarboxylate [prepared as described in Example 3(a)] and (S)-2-(4-methylphenyl)-1-phenylethylamine as starting materials, in relative proportions similar to those used in that Example, the title compound was obtained in a yield of 77%.

Infrared Absorption Spectrum (KBr), $v_{max}$ cm$^{-1}$: 3413, 2963, 2943, 2202, 1657, 1634, 1604, 1515, 1495, 1455, 1212, 703, 554

24(b) 17β-{N-[(1S)-2-(4-Methylphenyl)-1-phenylethyl] carbamoyl}androsta-3,5-diene-3-carboxylic acid Following a procedure similar to that described in Example 1(d), but using N-[(1S)-2-(4-methylphenyl)-1-phenylethyl]-3-cyanoandrosta-3,5-diene-17β-carboxamide [prepared as described in step (a) above] as a starting material, in a relative amount similar to that used in that Example, the title compound was obtained in a yield of 50%.

Nuclear Magnetic Resonance Spectrum (CDCl$_3$), δ ppm:
0.54 (3H, singlet);
0.89 (3H, singlet);
0.91-2.55 (18H, multiplet);
2.29 (3H, singlet);
2.98 3.12 (2H, multiplet),
5.24 (1H, quartet, J=7.3 Hz);
5.59 (1H, doublet, J=7.3 Hz);
5.85 (1H, singlet);
6.94 (2H, doublet, J=8.0 Hz);
7.04 (2H, doublet, J=8.0 Hz);
7.13 (1H, singlet);
7.20-7.34 (5H, multiplet).

Infrared Absorption Spectrum (KBr), $v_{max}$ cm$^{-1}$: 2942, 2913, 1669, 1635, 1516, 1500, 1421, 1276, 1189, 700.

EXAMPLE 25

17β-(N,N-Dibenzylcarbamoyl)androsta-3,5-diene-3-carboxylic acid (Compound No. 4)

25(a) N,N-Dibenzyl-3-cyanoandrosta-3,5-diene-17β-carboxamide

Following a procedure similar to that described in Example 3(b), but using S-2-pyridyl 3-cyanoandrosta-3,5-diene-17β-thiocarboxylate [prepared as described in Example 3(a)] and N,N-dibenzylamine as starting materials, in relative proportions similar to those used in that Example, the title compound was obtained in a yield of 80%.

Infrared Absorption Spectrum (KBr), $v_{max}$ cm$^{-1}$: 2943, 2929, 2904, 2205, 1641, 1604, 1495, 1467, 1426, 1206, 955, 734, 696.

25(b) 17β-(N,N-Dibenzylcarbamoyl)androsta-3,5-diene-3-carboxylic acid

Following a procedure similar to that described in Example 1(d), but using N,N-dibenzyl-3-cyanoandrosta-3,5-diene-17β-carboxamide [prepared as described in step (a) above] as a starting material, in a relative amount similar to that used in that Example, the title compound was obtained in a yield of 33%.

Nuclear Magnetic Resonance Spectrum (CDCl$_3$), δ ppm:
0.92 (6H, singlet);
0.97-2.55 (17H, multiplet);
2.76 (1H, triplet, J=8.8 Hz);
3.75 (1H, doublet, J=14.6 Hz);
4.17 (1H, doublet, J=17.1 Hz);
4.95 (1H, doublet, J=17.1 Hz)
5.48 (1H, doublet, J=14.6 Hz);
5.85 (1H, singlet);
7.10-7.40 (11H, multiplet).

Infrared Pbsorption Spectrum (KBr), $v_{max}$ cm$^{-1}$: 3029, 2943, 2911, 1706, 1673, 1631, 1422, 1280, 1206, 1190, 701.

EXAMPLE 26

Pivaloyloxymethyl 17β-{N-[1-(4-methoxyphenyl)-1-methylethyl]carbamoyl}androsta-3,5-diene-3-carboxylate (Compound No. 145)

1 ml of pivaloyloxymethyl iodide was added, whilst ice-cooling, to 15 ml of a dimethylacetamide solution containing 196 mg of sodium 17β-{N-[1(4-methoxyphenyl)-1-methylethyl]carbamoyl}androsta-3,5-diene-3-carboxylate (prepared by reacting the compound obtained as described in Example 2 with sodium hydroxide in a conventional salification process). The resulting solution was then stirred for 1 hour, whilst ice-cooling, after which it was diluted with ethyl acetate, washed with water, and dried over anhydrous sodium sulfate. The solvent was then removed by evaporation under reduced pressure. The resulting residue was subjected to silica gel column chromatography using a gradient elution method, with solutions of from 1 to 3% by volume of acetone in methylene chloride as the eluent, to give 157 mg of the title compound.

Nuclear Magnetic Resonance Spectrum (CDCl$_3$), δ ppm:
0.71 (3H, singlet);
0.93 (3H, singlet);
1.15 (9H, singlet);
1.71 (3H, singlet);
1.72 (3H, singlet);
3.81 (3H, singlet);
5.51 (1H, singlet);
5.7-6.1 (3H, multiplet);
6.87 (2H, doublet, J=8.8 Hz);
7.12 (1H, singlet);
7.34 (2H, doublet, J=8.8 Hz).

EXAMPLE 27

Methyl 17β-[N-(diphenylmethyl)carbamoyl] androsta-3,5-diene-3-carboxylate 2 ml of methanol, 0.13 ml of triethylamine, and 110 mg of bis(triphenylphosphine)-palladium (II) acetate were added to 8 ml of a dimethylformamide solution containing 300 mg of 17β-(N-diphenylmethylcarbamoyl)androsta-3,5-diene-3-trifluoromethanesulfonate (prepared as described in Preparation 5). The reaction mixture was then stirred at room temperature under a stream of carbon monoxide for 4 hours, after which it was diluted with diethyl ether, washed with water, with an aqueous solution of sodium hydrogencarbonate and with a saturated aqueous solution of sodium chloride, in that order, and dried over anhydrous magnesium sulfate. It was then concentrated by evaporation under reduced pressure. The resulting residue was subjected to column chromatography using 20 g of silica gel and using a gradient elution method, with mixtures of acetone and methylene chloride in ratios ranging from 1:99 to 3:97 by volume as the eluent, to give 214 mg of the title compound.

Nuclear Magnetic Resonance Spectrum (CDCl$_3$), δ ppm:
0.71 (3H, singlet);
0.90 (3H, singlet);
0.81-2.56 (18H, multiplet);
3.74 (3H, singlet);
5.79 (1H, singlet);
5.91 (1H, doublet, J=7.9 Hz);
6.29 (1H, doublet, J=7.9 Hz);
7.03 (1H, singlet);

EXAMPLE 28

17β[N-(Diphenylmethyl)carbamoyl]androsta-3,5-diene-3-carboxylic acid (Compound No. 2)

10 ml of water and 1 g of potassium hydroxide were added to a solution of 25 ml of methanol containing 214 mg of methyl 17β-(N-diphenylmethylcarbamoyl)-androsta-3,5-diene-3-carboxylate (prepared as described in Example 27). The reaction mixture was then heated under reflux for 4 hours. At the end of this time, methanol from the reaction mixture was removed by distillation under reduced pressure. The mixture was then made acidic by the addition of 1N aqueous hydrochloric acid and extracted with methylene chloride three times. The combined organic extracts were washed with water and with a saturated aqueous solution of sodium chloride, in that order, dried over anhydrous magnesium sulfate, and concentrated by evaporation under reduced pressure. The resulting residue was subjected to column chromatography using 20 g of silica gel and using a gradient elution method, with mixtures of acetone and methylene chloride in ratios ranging from 2:98 to 50:50 by volume as the eluent, to give 110 mg of the title compound.

The Nuclear Magnetic Resonance Spectrum and Infrared Absorption Spectrum data are identical with those of the compound obtained as described in Example 1(d).

EXAMPLE 29

17β-[N-(Diphenylmethyl)carbamoyl]androsta-3,5-diene-3-carboxylic acid (Compound No. 2)

1 ml of triethylamine, 0.5 ml of formic acid, and 110 mg of bis(triphenylphosphine)-palladium (II) acetate were added to 10 ml of a dimethylformamide solution containing 300 mg of 17β-(N-diphenylmethylcarbamoyl)androsta-3,5-diene-3-trifluoromethanesulfonate (prepared as described in Preparation 5). The reaction mixture was then stirred at room temperature under a stream of carbon monoxide for 4 hours. At the end of this time, 30 ml of water were added to the reaction mixture, which was then stirred at room temperature for 1 hour, and made acidic by the addition of 1N aqueous hydrochloric acid. It was then extracted with methylene chloride three times. The combined organic extracts were washed with water and with a saturated aqueous solution of sodium chloride, in that order, dried over anhydrous magnesium sulfate, and concentrated by evaporation under reduced pressure. The resulting residue was subjected to column chromatography using 20 g of silica gel and using a gradient elution method, with mixtures of acetone and methylene chloride in ratios ranging from 2:98 to 50:50 by volume as the eluent, to give 161 mg of the title compound.

The Nuclear Magnetic Resonance Spectrum and Infrared Absorption Spectrum data are identical with those of the compound obtained as described in Example 1(d).

EXAMPLE 30

17β-{N-[1-(2-Methoxyphenyl)-1-methylethyl]carbamoyl}androsta-3,5-diene-3-carboxylic acid (Compound No. 168)

Following a procedure similar to that described in Preparation 7, but using N-[1-(2-methoxyphenyl)-1-methylethyl]-3-formylandrosta-3,5-diene-17β-carboxamide (prepared as described in Preparation 8) as a starting material, in a relative amount similar to that used in that Preparation, the title compound was obtained in a yield of 37%.

The Nuclear Magnetic Resonance Spectrum and Infrared Absorption Spectrum data are identical with those of the compound obtained as described in Example 8.

EXAMPLE 31

17β-{N-[1-(3-Methoxyphenyl)-1-methylethyl]carbamoyl}androsta-3,5-diene-3-carboxylic acid (Compound No. 166)

Following a procedure similar to that described in Preparation 7, but using N-[1-(3-methoxyphenyl)-1-methylethyl]-3-formylandrosta-3,5-diene-17β-carboxamide (prepared as described in Preparation 9) as a starting material, in a relative amount similar to that used in that Preparation, the title compound was obtained in a yield of 54%.

The Nuclear Magnetic Resonance Spectrum and Infrared Absorption Spectrum data are identical with those of the compound obtained as described in Example 9.

PREPARATION 1

N-t-Butyl-3-oxo-4-androstene-17β-carboxamide

Following a procedure similar to that described in Example 2(b), but using 9.77 g of S-2-pyridyl 3-oxo-4-androstene-17β-thiocarboxylate [prepared as described in Example 2(a)] and 14 ml of t-butylamine, 8.9 g of the title compound were obtained.

Nuclear Magnetic Resonance Spectrum (CDCl$_3$), δ ppm:
0.74 (3H, singlet);
1.21 (3H, singlet);
1.37 (9H, singlet);
5.11 (1H, broad singlet);
5.74 (1H, singlet).

Infrared Absorption Spectrum (KBr), $v_{max}$ cm$^{-1}$: 3450, 2965, 1674, 1501.

PREPARATION 2

N-t-Butyl-3-cyanoandrosta-3,5-diene-17β-carboxamide

Following a procedure similar to that described in Example 2(c), but using 100 mg of N-t-butyl-3-oxo-4-androstene-17β-carboxamide (prepared as described in Preparation 1), 0.2 ml of diethyl cyanophosphate and 200 mg of a boron trifluoride-diethyl ether complex, 86 mg of the title compound were obtained as a crystalline substance, melting at 198° to 200° C.

Nuclear Magnetic Resonance Spectrum (CDCl$_3$), δ ppm:
0.74 (3H, singlet);
0.96 (3H, singlet);
1.38 (9H, singlet);
5.08 (1H, broad singlet);
5.79 (1H, broad singlet);
6.55 (1H, singlet). Infrared Absorption Spectrum (KBr), $v_{max}$ cm$^{-1}$: 3421, 2967, 2206, 1669, 1499.

PREPARATION 3

17β-(N-t-Butylcarbamoyl)androsta-3,5-diene-3-carboxylic acid

Following a procedure similar to that described in Example 2(d), but using 250 mg of N-t-butyl-3-cyanoandrosta-3,5-diene-17β-carboxamide (prepared as described in Preparation 2), 225 mg of the title compound were obtained.

The Nuclear Magnetic Resonance Spectrum and Infrared Absorption Spectrum data are identical with those of the compound obtained as described in Preparation 7.

PREPARATION 4

17β-(N-Diphenylmethylcarbamoyl)androsta-4-ene-3-one

Following a procedure similar to that described in Example 2(b), but using a-2-pyridyl 3-oxo-4-androstene-17β-thiocarboxylate [prepared as described in Example 2(a)] and benzhydrylamine as starting materials, in relative proportions similar to those used in that Example, the title compound was obtained in a yield of 85%.

Nuclear Magnetic Resonance Spectrum (CDCl$_3$), δ ppm:
0.73 (3H, singlet);
0.90–2.53 (20H, multiplet);
1.19 (3H, singlet);
5.74 (1H, singlet);
5.92 (1H, doublet, J=7.9 Hz);
6.30 (1H, doublet, J=7.9 Hz);
7.22–7.34 (10H, multiplet).

PREPARATION 5

17β-(N-Diphenylmethylcarbamoyl)androsta-3,5-diene-3-trifluoromethanesulfonate 0.6 g of 2,6-di-t-butyl-4-methylpyridine was added to 40 ml of a dry methylene chloride solution containing 1.0 g of 17β-(N-diphenylmethylcarbamoyl)androsta-4-ene-3-one (prepared as described in Preparation 4), and then 0.45 ml of trifluoromethanesulfonic anhydride was added gradually at 0° C. under a stream of nitrogen. The reaction mixture was then stirred for 30 minutes at 0° C., after which it was diluted with diethyl ether, washed with an aqueous solution of sodium hydrogencarbonate and with a saturated aqueous solution of sodium chloride, in that order, dried over anhydrous magnesium sulfate, and concentrated by evaporation under reduced pressure. The resulting residue was subjected to column chromatography using 55 g of silica gel and using a gradient elution method, with mixtures of acetone and methylene chloride in ratios ranging from 1:99 to 3:97 by volume as the eluent, to give 1.1 g of the title compound.

Nuclear Magnetic Resonance Spectrum (CDCl$_3$), δ ppm:
0.71 (3H, singlet);
0.96 (3H, singlet);
0.86–2.58 (18H, multiplet);
5.57 (1H, doublet, J=3.3 Hz);
5.90 (1H, doublet, J=7.9 Hz);
5.98 (1H:, singlet);
6.29 (1H, doublet, J=7.9 Hz);
7.22–7.36 (10H, multiplet)

PREPARATION 6

N-t-Butyl-3-formylandrosta-3,5-diene-17β-carboxamide 2 ml of a 1M solution of diisobutyl aluminum hydride in toluene were added at 0° C. to 10 ml of a dry solution of toluene containing 380 mg of N-t-butyl-3-cyanoandrosta-3,5-diene-17β-carboxamide (prepared as described in Preparation 2). The reaction mixture was then stirred at 0° C. for 30 minutes, after which 30 ml of an aqueous solution of 1.5 g of tartaric acid were added to the mixture. The reaction mixture was then stirred at room temperature for 2 hours, and then extracted with methylene chloride three times. The combined organic extracts were washed with water and with a saturated aqueous solution of sodium chloride, in that order. They were then dried over anhydrous magnesium sulfate, and concentrated by evaporation under reduced pressure. The resulting residue was subjected to column chromatography using 50 g of silica gel and using a gradient elution method, with mixtures of acetone and methylene chloride in ratios ranging from 1:99 to 4:96 by volume as the eluent, to give 325 mg of the title compound.

Nuclear Magnetic Resonance Spectrum (CDCl$_3$), δ ppm:
0.73 (3H, singlet);
0.92 (3H, singlet);
1.05–2.60 (18H, multiplet);
1.36 (9H, singlet);
5.09 (1H, broad singlet);
5.98 (1H, triplet, J=3.0 Hz);
6.78 (1H, doublet, J=2.0 Hz);
9.47 (1H, singlet).

Infrared Absorption Spectrum (KBr), $v_{max}$ cm$^{-1}$: 2964, 2943, 2905, 1671, 1631, 1501, 1451, 1385, 1252, 1220, 1171, 716, 646.

PREPARATION 7

17β-(N-t-Butylcarbamoyl)androsta-3,5-diene-3-carboxylic acid 600 mg of sodium phosphate dihydrate and 1.2 g of sodium chlorite were added, in that order, at room temperature to a mixture of 7.5 ml of t-butanol, 2.0 ml of water and 1 ml of 2-methyl-2-butene containing 400 mg of N-t-butyl-3-formylandrosta-3,5-diene-17β-carboxamide (prepared as described in Preparation 6). The reaction mixture was then stirred for 15 minutes. At the end of this time, the reaction mixture was quenched by pouring it into a ice-cooled aqueous solution of sodium thiosulfate; it was then made acidic by the addition of 1N aqueous hydrochloric acid, and extracted with ethyl acetate three times. The combined organic extracts were washed with water and with a saturated aqueous solution of sodium chloride, dried over anhydrous magnesium sulfate, and concentrated by evaporation under reduced pressure. The resulting residue was crystallized by the addition of diethyl ether, to give 225 mg of the title compound.

Nuclear Magnetic Resonance Spectrum (CDCl$_3$), δ ppm:
0.73 (3H, singlet);
0.92 (3H, singlet);
1.05–2.55 (18H, multiplet);
1.35 (9H, singlet);
5.09 (1H, broad singlet);
5.86 (1H, singlet);
7.14 (1H, singlet).

Infrared Absorption Spectrum (KBr), $v_{max}$ cm$^{-1}$: 2964, 2939, 2910, 1671, 1633, 1612, 1505, 1450, 1420, 1364, 1278, 1223, 1190, 926, 640.

PREPARATION 8

N-[1-(2-Methoxyphenyl)-1-methylethyl]-3-formylandrosta-3,5-diene-17β-carboxamide Following a procedure similar to that described in Preparation 6, but using N-[1-(2-methoxyphenyl)-1-methylethyl]-3-cyanoandrosta-3,5-diene-17β-carboxamide [prepared as described in Example 8(a)] as a starting material, in a relative amount similar to that used in that Preparation, the title compound was obtained in a yield of 74%.

Nuclear Magnetic Resonance Spectrum (CDCl₃), δ ppm:
0.67 (3H, singlet);
0.92 (3H, singlet);
1.04–2.54 (18H, multiplet);
1.77 (3H, singlet);
1.81 (3H, singlet);
3.83 (3H, singlet);
5.94 (1H, singlet);
5.98 (1H, triplet, J=3.0 Hz);
6.78 (1H, singlet);
6.88–6.97 (2H, multiplet);
7.21–7.26 (1H, multiplet);
7.40 (1H, doublet of doublets, J=8.0 & 1.0 Hz);
9.47 (1H, singlet).

PREPARATION 9

N-[1-(3-Methoxyphenyl)-1-methylethyl]-3-formylandrosta-3,5-diene-17β-carboxamide Following a procedure similar to that described in Preparation 6, but using N-[1-(3-methoxyphenyl)-1-methylethyl]-3-cyanoandrosta-3,5-diene-17β-carboxamide [prepared as described in Example 9(a)] as a starting material, in a relative amount similar to that used in that Preparation, the title compound was obtained in a yield of 95%.

Nuclear Magnetic Resonance Spectrum (CDCl₃) δ ppm:
0.73 (3H, singlet);
0.93 (3H, singlet);
1.00–2.56 (18H, multiplet);
1.70 (3H, singlet);
1.72 (3H, singlet);
3.80 (3H, singlet);
5.53 (1H, singlet);
5.97 (1H, singlet);
6.75–6.84 (2H, multiplet);
6.96–7.01 (2H, multiplet);
7.22–7.28 (1H, multiplet);
9.47 (1H, singlet)

PREPARATION 10a 1-(4-Methoxyphenyl)-1-methylethylamine
10(a) (i) 1-(4-Methoxyphenyl)-1-methylethyl azide A solution containing 25 g of methyl 4-methoxybenzoate in 100 ml of dry tetrahydrofuran was added dropwise, whilst ice-cooling, to 300 ml of a 1N solution of methyl magnesium bromide in tetrahydrofuran. The reaction mixture was then stirred at room temperature for 30 minutes. At the end of this time, an aqueous solution of ammonium chloride was added to the reaction mixture, which was then stirred for 10 minutes, and extracted three times with diethyl ether. The organic extract was washed with water and with a saturated aqueous solution of sodium chloride, in that order, after which it was dried over anhydrous magnesium sulfate, and concentrated by evaporation under reduced pressure. The resulting residue was dissolved in a mixture of 200 ml of chloroform and 100 ml of acetone, 20 g of sodium azide were added to this solution, and then 60 ml of trifluoroacetic acid and 100 ml of chloroform were added dropwise, whilst ice-cooling and stirring, to the mixture. The mixture was stirred at room temperature for 2 hours, after which it was allowed to stand overnight at room temperature. Water was then added to the mixture, and the mixture was neutralized by the addition of potassium carbonate. It was then extracted three times with methylene chloride. The combined organic extracts were washed with water and with a saturated aqueous solution of sodium chloride, in that order, dried over anhydrous magnesium sulfate, and concentrated by evaporation under reduced pressure. The resulting residue was subjected to column chromatography using 300 g of silica gel and using a gradient elution method, with mixtures of diethyl ether and hexane in ratios ranging from 1:99 to 4:96 by volume as the eluant, to give 21.0 g (yield 73.8%) of the title compound.

Nuclear Magnetic Resonance Spectrum (CDCl₃), δ ppm:
1.61 (6H, singlet);
3.81 (3H, singlet);
6.89 (2H, doublet, J=9 Hz);
7.36 (2H, doublet, J=9 Hz).

10(a) (ii) 1-(4-Methoxyphenyl)-1-methylethylamine 1.58 g of platinum oxide were added to a solution of 21.0 g of 1-(4-methoxyphenyl)-1-methylethyl azide [prepared as described in step (a) above] in 100 ml of methanol. The reaction mixture was then stirred for 5 hours under a stream of hydrogen. At the end of this time, the mixture was filtered, diluted with methylene chloride, and washed with an aqueous solution of sodium hydrogencarbonate, with water and with a saturated aqueous solution of sodium chloride, in that order. It was then dried over anhydrous magnesium sulfate, and concentrated by evaporation under reduced pressure, to give 17.2 g (yield 95%) of the title compound.

Nuclear Magnetic Resonance Spectrum (CDCl₃), δ ppm:
1.49 (6H, singlet);
1.89 (2H, singlet);
3.80 (3H, singlet);
6.86 (2H, doublet, J=9 Hz);
7.43 (2H, doublet, J=9 Hz). Infrared Absorption Spectrum (KBr), $v_{max}$ cm⁻¹: 2963, 2936, 1611, 1513, 1298, 1248, 1183, 1035, 831.

PREPARATION 10b 1-(3-Methoxyphenyl)-1-methylethylamine

Following a procedure similar to that described in Preparation 10a, but using methyl 3-methoxybenzoate as a starting material, in a relative amount similar to that used in that Preparation, the title compound was obtained in a yield of 31%.

Nuclear Magnetic Resonance Spectrum (CDCl₃), δ ppm:
1.49 (6H, singlet)
1.31 (2H, broad singlet);
3.82 (3H, singlet);
6.74–6.79 (1H, multiplet);
7.06–7.10 (2H, multiplet);
7.22–7.29 (1H, multiplet).

Infrared Absorption Spectrum (liquid film), $v_{max}$ cm⁻¹: 2964, 1602, 1582, 1487, 1430, 1289, 1250, 1038, 872, 782, 702.

PREPARATION 10c 1-(2-Methoxyphenyl)-1-methylethylamine

Following a procedure similar to that described in Preparation 10a, but using methyl 2-methoxybenzoate as a starting material, in a relative amount similar to that used in that Preparation, the title compound was obtained in a yield of 81%.

Nuclear Magnetic Resonance Spectrum (CDCl$_3$), δ ppm:
1.53 (6H, singlet);
2.06 (2H, broad singlet);
3.88 (3H, singlet);
6.89–6.93 (2H, multiplet);
7.19–7.24 (1H, multiplet);
7.32–7.35 (1H, multiplet).

Infrared Absorption Spectrum (lipid film), $v_{max}$ cm$^{-1}$: 2965, 1597, 1531, 1489, 1464, 1430, 1236, 1028, 754.

PREPARATION 10d 1-(3,5-Dimethoxyphenyl)-1-methylethylamine

Following a procedure similar to that described in Preparation 10a, but using methyl 3,5-dimethoxybenzoate as a starting material, in a relative amount similar to that used in that Preparation, the title compound was obtained in a yield of 75%.

Nuclear Magnetic Resonance Spectrum (CDCl$_3$), δ ppm:
1.48 (6H, singlet);
1.81 (2H, broad singlet);
3.80 (6H, singlet);
6.34 (1H, triplet, J=2 Hz);
6.66 (2H, doublet, J=2 Hz).

Infrared Absorption Spectrum (liquid film), $v_{max}$ cm$^{-1}$: 2694, 1596, 1457, 1423, 1204, 1154, 1053, 854, 699.

PREPARATION 10e 1-(3,4-Dimethoxyphenyl)-1-methylethylamine

Following a procedure similar to that described in Preparation 10a, but using methyl 3,4-dimethoxybenzoate, in a relative amount similar to that used in that Preparation, the title compound was obtained in a yield of 61%.

Nuclear Magnetic Resonance Spectrum (CDCl$_3$), δ ppm:
1.49 (6H, singlet);
1.73 (2H, broad singlet);
3.87 (3H, singlet);
3.91 (3H, singlet);
6.82 (1H, doublet, J=8 Hz);
7.01 (1H, doublet of doublets, J=2 & 8 Hz);
7.10 (1H, doublet, J=2 Hz).

Infrared Absorption Spectrum (liquid film), $v_{max}$ cm$^{-1}$: 2963, 1604, 1519, 1510, 1258, 1147, 1028, 766, 649.

PREPARATION 10f 1-(4-Fluorophenyl)-1-methylethylamine

Following a procedure similar to that described in Preparation 10a, but using methyl 4-fluorobenzoate as a starting material, in a relative amount similar to that used in that Preparation, the title compound was obtained in a yield of 20%.

Nuclear Magnetic Resonance Spectrum (CDCl$_3$), δ ppm:
1.48 (6H, singlet);
1.63 (2H, broad singlet);
6.96–7.03 (2H, multiplet);
7.44–7.50 (2H, multiplet).

Infrared Absorption Spectrum (liquid film), $v_{max}$ cm$^{-1}$: 2967, 1601, 1509, 1228, 1162, 835, 809, 551.

PREPARATION 10g 1-(4-Ethoxyphenyl)-1-methylethylamine

Following a procedure similar to that described in Preparation 10a, but using methyl 4-ethoxybenzoate as a starting material, in a relative amount similar to that used in that Preparation, the title compound was obtained in a yield of 60%.

Nuclear Magnetic Resonance Spectrum (CDCl$_3$), δ ppm:
1.40 (3H, triplet, J=7 Hz);
1.48 (6H, singlet);
1.68 (2H, broad singlet);
4.02 (2H, quartet, J=7 Hz);
6.82–6.88 (2H, multiplet);
7.37–7.43 (2H, multiplet).

Infrared Absorption Spectrum (liquid film), $v_{max}$ cm$^{-1}$: 2977, 1609, 1512, 1245, 1183, 1048, 834, 560.

PREPARATION 10h 1-(4-Methylphenyl)-1-methylethylamine

Following a procedure similar to that described in Preparation 10a, but using methyl 4-methylbenzoate as a starting material, in a relative amount similar to that used in that Preparation, the title compound was obtained in a yield of 34%.

Nuclear Magnetic Resonance Spectrum (CDCl$_3$), δ ppm:
1.48 (6H, singlet);
1.62 (2H, broad singlet);
2.33 (3H, singlet);
7.14 (2H, doublet, J=9 Hz);
7.39 (2H, doublet, J=9 Hz).

Infrared Absorption Spectrum (liquid film), $v_{max}$ cm$^{-1}$: 2965, 1587, 1514, 1360, 1189, 1115, 1020, 817, 722, 552.

PREPARATION 10i 1-(4-N,N-Dimethylaminophenyl-1-methylethylamine

Following a procedure similar to that described in Preparation 10a, but using methyl 4-N,N-dimethylaminobenzoate as a starting material, in a relatives amount similar to that used in that Preparation, the title compound was obtained in a yield of 48%.

Nuclear Magnetic Resonance Spectrum (CDCl$_3$), δ ppm:
1.48 (6H, singlet);
1.70 (2H, broad singlet);
2.95 (6H, singlet);
6.65–6.80 (2H, multiplet);
7.30 (2H, doublet, J=9 Hz)

Infrared Absorption Spectrum (liquid film), $v_{max}$ cm$^{-1}$: 2960, 1615, 1525, 815.

PREPARATION 11a

1-Methyl-1-(2-thienyl)ethylamine

11(a) (i) Methyl 2-methyl-2-(2-thienyl)propionate 9.2 g of sodium hydride (as a 55% w/w dispersion in mineral oil) were washed with hexane and mixed with 140 ml of a dry dimethylformamide. 30 ml of a solution of 15 g of methyl 2-thiophene acetate in dimethylformamide were then added dropwise, whilst ice-cooling, to this mixture. The resulting mixture was stirred at room temperature for 30 minutes, and cooled. 18 ml of methyl iodide were gradually added dropwise, and the mixture was stirred at room temperature overnight. It was then poured into ice-water and extracted three times with diethyl ether. The combined organic extracts were washed with water and with a saturated aqueous solution of sodium chloride, in that order, dried over anhydrous magnesium sulfate, and concentrated by evaporation under reduced pressure, to give 17.5 g of the title compound. Nuclear Magnetic Resonance Spectrum (CDCl$_3$), δ ppm:

3.68 (3H, singlet);
6.93–6.95 (2H, multiplet);
7.18–7.21 (1H, multiplet).

11(a) (ii) 2-Methyl-2-(2-thienyl)propionic acid

A solution containing 17.5 g of methyl 2-methyl-2-(2-thienyl)propionate [prepared as described in step (i) above], 12.6 g of potassium hydroxide, 72 ml of water, and 168 ml of 1,4-dioxane was heated under reflux for 2 hours. At the end of this time, it was diluted with ice-water, and extracted twice with diethyl ether. The aqueous layer was adjusted to a weakly acidic pH, extracted three times with diethyl ether, washed with water and with a saturated aqueous solution of sodium chloride, in that order, dried over anhydrous magnesium sulfate, and concentrated by evaporation under reduced pressure to give 15.8 g of the title compound.

Nuclear Magnetic Resonance Spectrum (CDCl$_3$), δ ppm:
1.68 (6H, singlet);
6.93–7.02 (2H, multiplet);
7.19–7.23 (1H, multiplet).

ii(a) (iii) 2-Methyl-2-(2-thienyl)propionylazide 10.6 ml of ethyl chlorocarbonate were gradually added, keeping the temperature below 0° C., to a solution of 15.8 g of 2-methyl-2-(2-thienyl)propionic acid [prepared as described in step (ii) above] and 15.6 ml of triethylamine in 210 ml of acetone. The reaction mixture was stirred at 0° C. for 2 hours, after which 110 ml of an aqueous solution containing 10.3 g of sodium azide were added to the mixture at 0° C. The reaction mixture was then stirred at 0° 0C. for 2 hours, diluted with water, and extracted three times with diethyl ether. The combined organic extracts were washed with 1N aqueous hydrochloric acid, with an aqueous solution of sodium hydrogencarbonate, and with a saturated solution of sodium chloride, in that order, after which it was dried over anhydrous magnesium sulfate, and concentrated by evaporation under reduced pressure to give 18.5 g of the title compound.

Nuclear Magnetic Resonance Spectrum (CDCl$_3$), δ ppm:
1.66 (6H, singlet);
6.91–7.00 (2H, multiplet);
7.18–7.25 (1H, multiplet).

11(a) (iv) 1-Methyl-1-(2-thienyl)ethylamine

A solution of 370 ml of dry benzene and 18.5 g of 2-methyl-2-(2-thienyl)propionylazide [prepared as described in step (iii) above] was heated under reflux for 4 hours. At the end of this time, the solvent was removed from the reaction mixture to a final volume of 270 ml by evaporation under reduced pressure. 97 ml of concentrated aqueous hydrochloric acid were then added to the remaining solution, whilst ice-cooling, and the reaction mixture was stirred at room temperature for 5 hours. At the end of this time, it was diluted with water, and extracted twice with diethyl ether. The remaining aqueous layer was adjusted to a basic pH value by the addition of an aqueous solution of potassium hydroxide. It was then extracted three times with diethyl ether, washed with a saturated aqueous solution of sodium chloride, dried over anhydrous magnesium sulfate, and concentrated by evaporation under reduced pressure to give 8.4 g of the title compound.

Nuclear Magnetic Resonance Spectrum (CDCl$_3$), δ ppm:
1.57 (6H, singlet);
1.76 (2H, broad singlet);
6.89–6.94 (2H, multiplet);
7.13–7.16 (1H, multiplet).

Infrared Absorption Spectrum (liquid film) $v_{max}$ cm$^{-1}$: 2966, 1589, 1465, 1362, 1241, 852, 826, 697.

PREPARATION 11b

1-Methyl-1-(3-thienyl)ethylamine

Following a procedure similar to that described in Preparation 11a, but using methyl 3-thienylacetate as a starting material, in a relative amount similar to that used in that Preparation, the title compound was obtained in a yield of 32%.

Nuclear Magnetic Resonance Spectrum (CDCl$_3$), δ ppm:
1.48 (6H, singlet);
1.61 (2H, singlet);
7.09–7.14 (1H, multiplet);
7.25–7.29 (2H, multiplet).

Infrared Absorption Spectrum (CDCl$_3$), $v_{max}$ cm$^{-1}$: 3350, 3260, 2940, 1580.

PREPARATION 11c

α,α-Dimethylfurfurylamine

Following a procedure similar to that described in Preparation 11a, but using ethyl 1-(2-furyl)propionate as a starting material, in a relative amount similar to that used in that Preparation, the title compound was obtained in a yield of 40%.

Nuclear Magnetic Resonance Spectrum (CDCl$_3$), δ ppm:
1.46 (6H, singlet);
1.66 (2H, singlet);
6.05–6.07 (1H, multiplet);
6.26–6.29 (1H, multiplet);
7.31–7.33 (1H, multiplet).

Infrared Absorption Spectrum (CHCl$_3$) $v_{max}$ cm$^{-1}$: 3300, 2960, 1710, 1590.

PREPARATION 12

4,4'-Difluorobenzhydrylamine 57.04 g of ammonium acetate and 12.69 g of sodium cyanoborohydride were added to a solution of 15.68 g of 4-fluorobenzophenone oxime in 315 ml of methanol. The mixture was stirred at room temperature, and then 135 ml of a 17–19% by volume aqueous solution of titanium trichloride were added dropwise over a period of 4 hours and 50 minutes. The reaction mixture was stirring for 1.5 hours, diluted with water and extracted with methylene chloride. The aqueous extract was adjusted to a basic pH value by the addition of an aqueous solution of sodium hydroxide and extracted with methylene chloride. At this point, the precipitate was removed by filtration using a Celite (trade mark) filter aid. The filtrate was dried over anhydrous magnesium sulfate and concentrated by evaporation under reduced pressure. The resulting residue was subjected to silica gel column chromatography using a gradient elution method, with solutions of acetone in methylene chloride in proportions ranging from 2–5% by volume as the eluent, to give 11.66 g (yield 79%) of the title compound.

Nuclear Magnetic Resonance Spectrum (CDCl$_3$), δ ppm:

5.11 (1H, singlet);

6.92 (4H, multiplet);

7.25 (4H, multiplet).

Infrared Absorption Spectrum (liquid film) ν$_{max}$ cm$^{-1}$: 1602, 1506, 1223, 1155.

Mass Spectrum (m/z): 219 (M$^+$), 203, 201, 138, 123.

PREPARATION 13

4-Hydroxybenzhydrylamine

A procedure similar to that described in Preparation 12 was repeated, but using 86 ml of a methanolic solution containing 4.28 g of 4-hydroxybenzophenone oxime, 17.03 g of ammonium acetate, 3.79 g of sodium cyanoborohydride, and 40.1 ml of a 17–19% by volume aqueous solution of titanium trichloride, and using a dilute aqueous solution of sodium hydrogencarbonate instead of the aqueous solution of sodium hydroxide, and using ethyl acetate as the extracting solvent. The residue obtained was subjected to silica gel column chromatography and eluted with a 80% by volume solution of ethyl acetate in hexane, with ethyl acetate itself and with a 3% by volume solution of methanol in ethyl acetate, to give 2.74 g of the title compound as crystals, melting at 113°–115° C. (after recrystallization from methylene chloride).

Nuclear Magnetic Resonance Spectrum (hexadeuterated dimethyl sulfoxide), δ ppm:

5.0 (1H, singlet);

6.68 (2H, doublet, J=9 Hz);

7.1–7.5 (7H, multiplet).

Infrared Absorption Spectrum (Nujol-trade mark), ν$_{max}$ cm$^{-1}$: 3336, 2923, 1609, 1591, 1576, 1248.

Elemental analysis: Calculated for C$_{13}$H$_{13}$NO: C, 78.36%; H, 6.58%; N,7.03%. Found: C, 77.97%; H, 6.6%; N,6.93%.

PREPARATION 14

4,4'-Dimethoxybenzhydrylamine

Following a procedure similar to that described in Preparation 12, but using 10.7 g of 4,4'-dimethoxybenzophenone oxime, 33.9 g of ammonium acetate, 7.46 g of sodium cyanoborohydride, and 79 ml of a 17–19% by volume aqueous solution of titanium trichloride, 8.18 g of the title compound were obtained, as an oily substance.

Nuclear Magnetic Resonance Spectrum (CDCl$_3$), δ ppm:

3.78 (6H, singlet);

5.09 (1H, singlet);

6.85 (4H, doublet, J=9 Hz);

7.26 (4H, doublet, J=9 Hz).

Infrared Absorption Spectrum (liquid film), ν$_{max}$ cm$^{-1}$: 2953, 2834, 1608, 1583, 1508, 1246.

Mass Spectrum (m/z): 243 (M$^+$), 242, 227

PREPARATION 15

4-Methoxybenzhydrylamine

Following a procedure similar to that described in Preparation 12, but using 9.4 g of 4-methoxybenzophenone oxime, 33.9 g of ammonium acetate, 7.46 g of sodium cyanoborohydride, and 79 ml of a 17–19% by volume aqueous solution of titanium trichloride, 6.78 g of the title compound were obtained as an oily substance.

Nuclear Magnetic Resonance Spectrum (CDCl$_3$), δ ppm:

3.76 (3H, singlet);

5.10 (1H, singlet);

6.84 (2H, doublet, J=9 Hz);

7.1–7.5 (7H, multiplet).

Infrared Absorption Spectrum (liquid film), ν$_{max}$ cm$^{-1}$: 3025, 2834, 1609, 1584, 1509, 1247.

Mass Spectrum (m/z): 213 (M$^+$), 197, 182, 136

PREPARATION 16a

N-(Diphenylmethyl)-3-cyanoandrosta-3,5-diene-17β-carboxamide 0.106 ml of benzhydrylamine were added to a solution of 100 mg of 3-cyanoandrosta-3,5-diene-17β-carboxylic acid [prepared as described in Example 1(b)], a catalytic amount of 4-dimethylaminopyridine and 0.131 ml of triethylamine in 4 ml of methylene chloride. 88.0 mg of tosyl chloride were then divided into three portions and added to this reaction mixture at 30 minute intervals at room temperature, whilst stirring. One hour after finishing the addition of the tosyl chloride, the reaction mixture was diluted with methylene chloride, and washed with 1N aqueous hydrochloric acid, with water, with an aqueous solution of sodium hydrogencarbonate, and with a saturated aqueous solution of sodium chloride, in that order. It was then dried over anhydrous magnesium sulfate, and concentrated by evaporation under reduced pressure. The resulting residue was crystallized from acetone, to give 138 mg (yield 92%) of the title compound.

The Nuclear Magnetic Resonance Spectrum and Infrared Absorption Spectrum data are identical with those of the compound obtained as described in Example 1(c).

PREPARATION 16b

N-t-Butyl-3-cyanoandrosta-3,5-diene-17β-carboxamide

Following a procedure similar to that described in Preparation 16a, but using 3-cyanoandrosta-3,5-diene-17β-carboxylic acid [prepared as described in Example 1(b)] and t-butylamine as starting materials, in relative proportions similar to those used in that Preparation, the title compound was obtained in a yield of 81%.

The Nuclear Magnetic Resonance Spectrum and Infrared Absorption Spectrum data are identical with those of the compound obtained as described in Preparation 2.

PREPARATION 16c

N-[1-(3,5-Dimethoxyphenyl)-1-methylethyl]-3-cyanoandrosta-3,5-diene-17β-carboxamide Following a procedure similar to that described in Preparation 16a, but using 3-cyanoandrosta-3,5-diene-17β-carboxylic acid [prepared as described in Example 1(b)] and 1-(3,5-dimethoxyphenyl)-1-methylethylamine as starting materials, in relative proportions similar to those used in that Preparation, the title compound was obtained in a yield of 98%.

The Nuclear Magnetic Resonance Spectrum and Infrared Absorption Spectrum data are identical with those of the compound obtained as described in Example 10(a).

PREPARATION 16d

N-[1-(4-Methoxyphenyl)-1-methylethyl]-3-cyanoandrosta-3,5-diene-17β-carboxamide Following a procedure similar to that described in Preparation 16a, but using 3-cyanoandrosta-3,5-diene-17β- carboxylic acid [prepared as described in Example 1(b)] and 1-(4-methoxyphenyl)-1-methylethylamine as starting materials, in relative proportions similar to those used in that Preparation, the title compound was obtained in a yield of 93%.

The Nuclear Magnetic Resonance Spectrum and Infrared Absorption Spectrum data are identical with those of the compound obtained as described in Example 2(c).

PREPARATION 16e

N-[1-Methyl-1-phenylethyl]-3-cyanoandrosta-3,5-diene-17β-carboxamide

Following a procedure similar to that described in Preparation 16a, but using 3-cyanoandrosta-3,5-diene-17β-carboxylic acid [prepared as described in Example 1(b)] and 1-methyl-1-phenylethylamine as starting materials, in relative proportions similar to those used in that Preparation, the title compound was obtained in a yield of 74%.

The Nuclear Magnetic Resonance Spectrum and Infrared Absorption Spectrum data are identical with those of the compound obtained as described in Example 4(a).

PREPARATION 16f

N-[1-(3,5-Dimethoxyphenyl)-1-methylethyl]-3-cyanoandrosta-3,5-diene-17β-carboxamide Vilsmeier reagent was prepared from 1.7 ml of dimethylformamide, 1.8 ml of phosphorus oxychloride, and 5 ml of methylene chloride. 0.23 ml of this Vilsmeier reagent was then added to a solution of 100 mg of 3-cyanoandrosta-3,5-diene-17β-carboxylic acid [prepared as described in Example 1(b)] in 2 ml of methylene chloride. The reaction mixture was then stirred at room temperature for 40 minutes, after which a solution of 1-(3,5-dimethoxyphenyl)-1-methylethylamine [prepared as described in Preparation 10(d)] and 70 μl of triethylamine in 2 ml of methylene chloride were added. The reaction mixture was then diluted with ethyl acetate, washed with dilute aqueous hydrochloric acid, with an aqueous solution of sodium chloride, with a 5% w/v aqueous solution of sodium hydrogencarbonate, and with a saturated aqueous solution of sodium chloride, in that order. It was then dried over anhydrous magnesium sulfate, and concentrated by evaporation under reduced pressure. The resulting residue was subjected to silica gel column chromatography and using a gradient elution method, with solutions of from 1 to 4% by volume of acetone in methylene chloride as the eluent, to give 76 mg (yield 50%) of the title compound.

The Nuclear Magnetic Resonance Spectrum and Infrared Absorption Spectrum data are identical with those of the compound obtained as described in Example 10(a).

PREPARATION 17

N-(Diphenylmethyl)androsta-4-ene-3-one-17β-carboxamide 0.108 ml of benzhydrylamine was added to a solution of 100 mg of androsta-4-ene-3-one-17β-carboxylic acid, a catalytic amount of 4-dimethylaminopyridine and 0.132 ml of triethylamine in 4 ml of methylene chloride. 0.037 ml of methanesulfonyl chloride was divided into three portions and added to this reaction mixture at intervals of 30 minutes at room temperature, whilst stirring. One hour after finishing the addition of methanesulfonyl chloride, the reaction mixture was diluted with methylene chloride, washed with 1N aqueous hydrochloric acid, with water, with an aqueous solution of sodium hydrogencarbonate and with a saturated aqueous solution of sodium chloride, in that order. It was then dried over anhydrous magnesium sulfate, and concentrated by evaporation under reduced pressure. The resulting residue was crystallized from acetone to give 113.2 mg (yield 74%) of the title compound.

Nuclear Magnetic Resonance Spectrum (CDCl₃), δ ppm:
0.72 (3H, singlet);
0.77–2.44 (20H, multiplet);
1.18 (3H, singlet);
5.73 (1H, singlet);
5.88 (1H, doublet, J=8 Hz);
6.28 (1H, doublet, J=8 Hz);
7.2;–7.36 (10H, multiplet).

Infrared Absorption Spectrum (KBr), $v_{max}$ cm⁻¹: 2941, 2875, 1665, 1616, 1518, 1495, 1449, 1230, 699.

PREPARATION 18

N-(Diphenylmethyl)androsta-4-ene-3-one-17β-carboxamide 0.108 ml of benzhydrylamine was added to a solution of 100 mg of androsta-4-ene-3-one-17β-carboxylic acid, a catalytic amount of 4-dimethylaminopyridine and 0.132 ml of triethylamine in 4 ml of methylene chloride. 0.050 ml of trifluoromethanesulfonyl chloride was divided into three portions and added to this reaction mixture at intervals of 30 minutes at room temperature, whilst stirring. One hour after finishing the addition of trifluoromethanesulfonyl chloride, the reaction mixture was diluted with methylene chloride, washed with 1N aqueous hydrochloric acid, with water, with an aqueous solution of sodium hydrogencarbonate and with a saturated aqueous solution of sodium chloride, in that order. It was then dried over anhydrous magnesium sulfate, and concentrated by evaporation under reduced pressure. The resulting residue was crystallized from acetone to give 135.2 mg (yield 89%) of the title compound, having the same properties as the product of Preparation 17.

PREPARATION 19

N-(Diphenylmethyl)androsta-4-ene-3-one-17β-carboxamide 0.108 ml of benzhydrylamine was added to a solution of 100 mg of androsta-4-ene-3-one-17β-carboxylic acid, a catalytic amount of 4-dimethylaminopyridine and 0.132 ml of triethylamine in 4 ml of methylene chloride. 0.060 ml of benzenesulfonyl chloride was divided into three portions and added to this reaction mixture at intervals of 30 minutes at room temperature, whilst stirring. One hour after finishing the addition of benzenesulfonyl chloride, the reaction mixture was diluted with methylene chloride, washed with 1N aqueous hydrochloric acid, with water, with an aqueous solution of sodium hydrogencarbonate and with a saturated aqueous solution of sodium chloride, in that order. It was then dried over anhydrous magnesium sulfate, and concentrated under reduced pressure. The resulting residue was crystallized from acetone to give 130.1 mg (yield 85%) of the title compound, having the same properties as the product of Preparation 17.

We claim:

1. A method for the treatment of disorders arising from high levels of 5α-reductase in a mammal, which may be human, which method comprises administering to said mammal an effective amount of an active compound, wherein said active compound is selected from the group consisting of compounds of formula (I) and pharmaceutically acceptable salts and esters thereof:

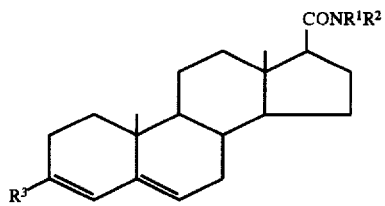

wherein:

$R^1$ represents: a hydrogen atom; an alkyl group having from 1 to 6 carbon atoms; or a substituted alkyl group having from 1 to 6 carbon atoms and having at least one substituent selected from the group consisting of aryl groups as defined below and aromatic heterocyclic groups as defined below;

$R^2$ represents:

(a) a substituted alkyl group having from 1 to 6 carbon atoms and having at least one substituent selected from the group consisting of aryl groups as defined below and aromatic heterocyclic groups as defined below, and said alkyl group further optionally having a single hydroxy or carboxy substituent; or (b) a diarylamino group in which the two aryl parts are the same or different and each is as defined below;

$R^3$ represents a carboxy group or a group of formula —$CONHSO_2R^4$ wherein $R^4$ represents an alkyl group having from 1 to 6 carbon atoms;

said aryl groups are carbocyclic aromatic groups having from 6 to 14 ring carbon atoms and which are unsubstituted or are substituted by at least one substituent selected from the group consisting of substituents A, defined below;

said aromatic heterocyclic groups have 5 or 6 ring atoms of which from 1 to 3 are hetero-atoms selected from the group consisting of nitrogen, oxygen and sulfur heteroatoms and the remainder are carbon atoms, said group being unsubstituted or being substituted by at least one substituent selected from the group consisting of substituents B, defined below;

said substituents A are selected from the group consisting of: alkyl groups having from 1 to 6 carbon atoms; alkoxy groups having from 1 to 6 carbon atoms; alkoxycarbonyl groups having from 2 to 7 carbon atoms; hydroxy groups; halogen atoms; amino groups; alkylamino groups having from 1 to 6 carbon atoms; dialkylamino groups in which each alkyl part has from 1 to 6 carbon atoms; aliphatic acylamino groups having from 1 to 6 carbon atoms; aromatic acylamino groups in which the aromatic part is a carbocyclic aryl group which has from 6 to 10 ring carbon atoms and which is unsubstituted or is substituted by at least one substituent selected from the group consisting or substituents C, defined below; cyano groups; nitro groups; and carboxy groups;

said substituents B are selected from the group consisting of: alkyl groups having from 1 to 6 carbon atoms; alkoxy groups having from 1 to 6 carbon atoms; hydroxy groups; halogen atoms; carbocyclic aryl groups which have from 6 to 10 ring carbon atoms and which are unsubstituted or are substituted by at least one substituent selected from the group consisting of substituents C, defined below; amino groups; alkylamino groups having from 1 to 6 carbon atoms; dialkylamino groups in which each alkyl part has from 1 to 6 carbon atoms; aliphatic acylamino groups having from 1 to 6 carbon atoms; aromatic acylamino groups in which the aromatic part is a carbocyclic aryl group which has from 6 to 10 ring carbon atoms and which is unsubstituted or is substituted by at least one substituent selected from the group consisting of substituents C, defined below; nitro groups; and carboxy groups;

said substituents C are selected from the group consisting of: alkyl groups having from 1 to 6 carbon atoms; alkoxy groups having from 1 to 6 carbon atoms; hydroxy groups; halogen atoms; amino groups; alkylamino groups having from 1 to 6 carbon atoms; dialkylamino groups in which each alkyl part has from 1 to 6 carbon atoms; aliphatic acylamino groups having from 1 to 6 carbon atoms; cyano groups; nitro groups; and carboxy groups.

2. The method of claim 1, wherein:

$R^1$ represents:
a hydrogen atom;
an isopropyl group;
a benzyl group;
a substituted benzyl group having on the aromatic ring at least one substituent selected from the group consisting of methyl, ethyl, methoxy, ethoxy, hydroxy, ethoxycarbonyl, methoxycarbonyl, amino, methylamino, ethylamino, dimethylamino, diethylamino, formamido and acetamido groups and fluorine, chlorine and bromine atoms; or
a thienylmethyl group;

$R^2$ represents:

(a) a substituted alkyl group having from 1 to 4 carbon atoms and having 1 or 2 substituents selected from the group consisting of:
phenyl groups;
substituted phenyl groups having at least one substituent selected from the group consisting of methyl, ethyl, methoxy, ethoxy, hydroxy, methoxycarbonyl, ethoxycarbonyl, amino, methylamino, ethylamino, dimethylamino, diethylamino, formamido and acetamido groups and fluorine, chlorine and bromine atoms;
furyl groups;
methyl-substituted furyl groups
thienyl groups; and
methyl-substituted thienyl groups;

(b) a diphenylamino group; or (c) a substituted diphenylamino group having at least one substituent selected from the group consisting of methyl, ethyl, methoxy, ethoxy, hydroxy, methoxycarbonyl, ethoxycarbonyl, amino, methylamino, ethylamino, dimethylamino, diethylamino, formamido and acetamido groups and fluorine, chlorine and bromine atoms; and $R^3$ represents:
a carboxy group;
an alkoxycarbonyl group having from 2 to 5 carbon atoms;
a benzyloxycarbonyl group;
an alkanoyloxyalkoxycarbonyl group in which the alkanoyl part has from 1 to 5 carbon atoms and the alkoxy part has 1 or 2 carbon atoms;
a cycloalkanecarbonyloxyalkoxycarbonyl group in which the cycloalkane part has from 5 to 7 carbon atoms and the alkoxy part has 1 or 2 carbon atoms;

a methoxycarbonyl or ethoxycarbonyl group which is substituted by an alkoxycarbonyloxy group having from 2 to 5 carbon atoms;
a cycloalkyloxycarbonyloxyalkoxycarbonyl group in which the cycloalkyl part has from 5 to 7 carbon atoms and the alkoxy part has 1 or 2 carbon atoms;
a (5-phenyl-, 5-methyl- or 5-ethyl-2-oxo-1,3-dioxolen-4-yl)methoxycarbonyl group;
a phthalidyloxycarbonyl group; or
a group of formula —CONHSO$_2$R$^4$, wherein R$^4$ represents a methyl group or an ethyl group.

3. The method of claim 1, wherein:
R$^1$ and R$^2$ are independently selected from the group consisting of benzyl groups and substituted benzyl groups on the aromatic ring having at least one substituent selected from the group consisting of methyl, methoxy, hydroxy and acetamido groups and fluorine and chlorine atoms; and
R$^3$ represents a carboxy group, a methoxycarbonyl group, an ethoxycarbonyl group, a pivaloyloxymethoxycarbonyl group, an ethoxycarbonyloxymethoxycarbonyl group, a 1-(ethoxycarbonyloxy)ethoxycarbonyl group, an isopropoxycarbonyloxymethoxycarbonyl group, a 1-(isopropoxycarbonyloxy)ethoxycarbonyl group, a (5-methyl-2-oxo-1,3-dioxolen-4-yl)methoxycarbonyl group, a phthalidyloxycarbonyl group or a group of formula —CONHSO$_2$R$^4$, wherein R$^4$ represents a methyl group.

4. The method of claim 1, wherein:
R$^1$ represents a hydrogen atom;
R$^2$ represents:
(a) a substituted alkyl group having from 1 to 4 carbon atoms and having 1 or 2 substituents selected from the group consisting of:
phenyl groups;
substituted phenyl groups having at least one substituent selected from the group consisting of methyl, methoxy, hydroxy, dimethylamino groups, acetamido groups, fluorine atoms, chlorine atoms;
furyl groups and thienyl groups;
(b) a diphenylamino group; or
(c) a substituted diphenylamino group having at least one substituent selected from the group consisting of methyl, methoxy, hydroxy, dimethylamino and acetamido and fluorine and chlorine atoms; and
R$^3$ represents a carboxy group, a methoxycarbonyl group, an ethoxycarbonyl group, a pivaloyloxymethoxycarbonyl group, an ethoxycarbonyloxymethoxycarbonyl group, a 1-(ethoxycarbonyloxy)ethoxycarbonyl group, an isopropoxycarbonyloxymethoxycarbonyl group, a 1-(isopropoxycarbonyloxy)ethoxycarbonyl group, a (5-methyl-2-oxo-1,3-dioxolen-4-yl)methoxycarbonyl group, a phthalidyloxycarbonyl group or a group of formula —CONHSO$_2$R$^4$, wherein R$^4$ represents a methyl group.

5. The method of claim 1, wherein:
R$^1$ represents a hydrogen atom;
R$^2$ represents an alkyl group having from 1 to 3 carbon atoms and substituted with 1 or 2 substituents selected from the group consisting of:
phenyl groups;
substituted phenyl groups having at least one substituent selected from the group consisting of methyl, methoxy and hydroxy groups and fluorine and chlorine atoms;
furyl groups and thienyl groups; and
R$^3$ represents a carboxy group, a methoxycarbonyl group or an ethoxycarbonyl group.

6. The method of claim 1, wherein said active compound is selected from the group consisting of:

17-[N-(1,2-Diphenylethyl)carbamaoyl]androsta-3,5-diene-3-carboxylic acid;
17-[N-(Diphenylmethyl)carbamoyl]androsta-3,5-diene-3-carboxylic acid;
17-[N-(4,4'-Dimethoxybenzhydryl)carbamoyl]androsta-3,5-diene-3-carboxylic acid;
17-[N-(1-Methyl-1-phenylethyl)carbamoyl]androsta-3,5-diene-3-carboxylic acid;
17-{N-[1-Methyl-1-1-(2-thienyl)ethyl]carbamoyl}androsta-3,5-diene-3-carboxylic acid;
17-{N-[1-(4-Fluorophenyl)-1-methylethyl]carbamoyl}androsta-3,5-diene-3-carboxylic acid;
17β-[N-(4-Hydroxybenzhydryl)carbamoyl]androsta-3,5-diene-3-carboxylic acid;
17-{N-[1-(3,5-Dimethoxyphenyl)-1-methylethyl]carbamoyl}androsta-3,5-diene-3-carboxylic acid;
17-[N-(Diphenylamino)carbamoyl]androsta-3,5-diene-3-carboxylic acid;
17-{N-[1-(3-Methoxyphenyl)-1-methylethyl]carbamoyl}androsta-3,5-diene-3-carboxylic acid;
17-{N-[1-(2-Methoxyphenyl)-1-methylethyl]carbamoyl}androsta-3,5-diene-3-carboxylic acid;
17-[N-(α,α-Dimethylfurfuryl)carbamoyl]androsta-3,5-diene-3-carboxylic acid;
17-{N-[1-(4-N,N-Dimethylaminophenyl)-1-methylethyl]carbamoyl}androsta-3,5-diene-3-carboxylic acid;
17-{N-[1-(3,4-Dimethoxyphenyl)-1-methylethyl]carbamoyl}androsta-3,5-diene-3-carboxylic acid;
17-{N-[1-(4-Ethoxyphenyl)-1-methylethyl]carbamoyl}androsta-3,5-diene-3-carboxylic acid; and
17-{N-[1-Methyl-1-(3,4,5-trimethoxyphenyl)ethyl]carbamoyl}androsta-3,5-diene-3-carboxylic acid;
and pharmaceutically acceptable salts and esters thereof.

7. The method of claim 1, wherein said active compound is selected from the group consisting of 17-[N-(1,2-diphenylethyl)carbamoyl]androsta-3,5-diene-3-carboxylic acid and pharmaceutically acceptable salts and esters thereof.

8. The method of claim 1, wherein said active compound is selected from the group consisting of 17-[N-(diphenylmethyl)carbamoyl]-androsta-3,5-diene-3-carboxylic acid and pharmaceutically acceptable salts and esters thereof.

9. The method of claim 1, wherein said active compound is selected from the group consisting of 17-[N-(4,4'-dimethoxybenzhydryl)carbamoyl]androsta-3,5-diene-3-carboxylic acid and pharmaceutically acceptable salts and esters thereof.

10. The method of claim 1, wherein said active compound is selected from the group consisting of 17-[N-(1-methyl-1-phenylethyl)carbamoyl]androsta-3,5-diene-3-carboxylic acid and pharmaceutically acceptable salts and esters thereon.

11. The method of claim 1, wherein said active compound is selected from the group consisting of 17-{N-[1-methyl-1-(2-thienyl)ethyl]carbamoyl}androsta-3,5-diene-3-carboxylic acid and pharmaceutically acceptable salts and esters thereof.

12. The method of claim 1, wherein said active compound is selected from the group consisting of 17-{N-[1-(4-fluorophenyl)-1-methylethyl]carbamoyl}androsta-3,5- diene-3-carboxylic acid and pharmaceutically acceptable salts and esters thereof.

13. The method of claim 1, wherein said active compound is selected from the group consisting of 17β-[N-(4-hydroxybenzhydryl) carbamoyl]androsta-3,5-diene-3-carboxylic acid and pharmaceutically acceptable salts and esters thereof.

14. The method of claim 1, wherein said active compound is selected from the group consisting of 17-{N-[1-(3,5-dimethoxyphenyl)-1-methylethyl]carbamoyl}androsta-3,5-diene-3-carboxylic acid and pharmaceutically acceptable salts and esters thereof.

15. The method of claim 1, wherein said active compound is selected from the group consisting of 17-[N-(diphenylamino)carbamoyl]androsta-3,5-diene-3-carboxylic acid and pharmaceutically acceptable salts and esters thereof.

16. The method of claim 1, wherein said active compound is selected from the group consisting of 17-{N-[1-(3-methoxyphenyl)-1-methylethyl]carbamoyl}androsta-3,5-diene-3-carboxylic acid and pharmaceutically acceptable salts and esters thereof.

17. The method of claim 1, wherein said active compound is selected from the group consisting of 17-{N-[1-(2-methoxyphenyl)-1-methylethyl]carbamoyl}androsta-3,5-diene-3-carboxylic acid and pharmaceutically acceptable salts and esters thereof.

18. The method of claim 1, wherein said active compound is selected from the group consisting of 17-[N-(α,α-dimethylfurfuryl) carbamoyl]androsta-3,5-diene-3-carboxylic acid and pharmaceutically acceptable salts and esters thereof.

19. The method of claim 1, wherein said active compound is selected from the group consisting of 17-{N-[1-(4-N,N-dimethylaminophenyl)-1-methylethyl]carbamoyl}androsta-3,5-diene-3-carboxylic acid and pharmaceutically acceptable salts and esters thereof.

20. The method of claim 1, wherein said active compound is selected from the group consisting of 17-{N-[1-(3,4-dimethoxyphenyl)-1-methylethyl]carbamoyl}androsta-3,5-diene-3-carboxylic acid and pharmaceutically acceptable salts and esters thereof.

21. The method of claim 1, wherein said active compound is selected from the group consisting of 17-{N-[1-(4-ethoxyphenyl)-1-methylethyl]carbamoyl}androsta-3,5-diene-3-carboxylic acid and pharmaceutically acceptable salts and esters thereof.

22. The method of claim 1, wherein said active compound is selected from the group consisting of 17-{N-[1-methyl-1-(3,4,5-trimethoxyphenyl)ethyl]carbamoyl}androsta-3,5-diene-3-carboxylic acid and pharmaceutically acceptable salts and esters thereof.

* * * * *